US011248016B2

(12) United States Patent
Bottley et al.

(10) Patent No.: US 11,248,016 B2
(45) Date of Patent: Feb. 15, 2022

(54) GLYCOLIPIDS AND PHARMACEUTICAL COMPOSITIONS THEREOF FOR USE IN THERAPY

(71) Applicant: THE UNIVERSITY OF NOTTINGHAM, Nottinghamshire (GB)

(72) Inventors: Andrew Bottley, Nottinghamshire (GB); Christopher Hayes, Nottinghamshire (GB); Graham Seymour, Nottinghamshire (GB); Anna Grabowska, Nottinghamshire (GB); Philip Clarke, Nottinghamshire (GB)

(73) Assignee: THE UNIVERSITY OF NOTTINGHAM, Nottinghamshire (GB)

(*) Notice: Subject to any disclaimer, the term of this patent is extended or adjusted under 35 U.S.C. 154(b) by 0 days.

(21) Appl. No.: 16/522,216

(22) Filed: Jul. 25, 2019

(65) Prior Publication Data
US 2019/0382433 A1 Dec. 19, 2019

Related U.S. Application Data

(63) Continuation of application No. 15/301,264, filed as application No. PCT/GB2015/051068 on Apr. 7, 2015.

(30) Foreign Application Priority Data

Apr. 4, 2014 (GB) ..................................... 1406172

(51) Int. Cl.
C07H 15/06 (2006.01)
A61K 45/06 (2006.01)
A61K 31/7032 (2006.01)
A61K 33/243 (2019.01)
A23L 33/00 (2016.01)
A23L 33/16 (2016.01)

(52) U.S. Cl.
CPC .............. *C07H 15/06* (2013.01); *A23L 33/16* (2016.08); *A23L 33/30* (2016.08); *A61K 31/7032* (2013.01); *A61K 33/243* (2019.01); *A61K 45/06* (2013.01); *A23V 2002/00* (2013.01)

(58) Field of Classification Search
CPC .. C07H 15/06; C07D 309/02; A61K 31/7032; A61K 33/243; A61K 45/06; A61P 35/00; A61P 31/12; A61P 25/28; A61P 25/16; A61P 25/00; A61P 21/00; A23L 33/30; A23L 33/16
See application file for complete search history.

(56) References Cited

U.S. PATENT DOCUMENTS

| 5,268,180 A | 12/1993 | Morancais et al. |
| 10,428,102 B2 | 10/2019 | Bottley et al. |
| 2008/0152737 A1 | 6/2008 | Shyur et al. |
| 2017/0027532 A1 | 9/2017 | Bottley et al. |

FOREIGN PATENT DOCUMENTS

| WO | 2010048955 A1 | 5/2010 |
| WO | 2013/152299 A2 | 10/2013 |

OTHER PUBLICATIONS

Carpenter et al., Green Chemistry, 2010, 12, p. 2012-2018. (Year: 2010).*
Schwendener et al. (Weissig, V., ed., Methods of Molecular Biology: Liposomes: Methods and Protocols vol. 1: Pharmaceutical Nanocarriers, 2010, Humana Press, p. 129-138. (Year: 2010).*
FDA Guidance for Industry on Container Closure Systems for Packaging Human Drugs and Biologies, May 1999, 56 pages. (Year: 1999).*
Hou et al., "A Galactolipid Possesses Novel Cancer Chemopreventive Effects by Suppressing Inflammatory Mediators and Mouse B16 Melanoma," Cancer Research, Jul. 15, 2007; vol. 67, issue 14, pp. 6907-6915.
Stadler et al., "Stereoselectivity of Microbial Lipases: The Substitution at Position sn-2 of Triacylglycerol Analogs Influences the Stereoselectivity of Different Microbial Lipases," European Journal of Biochemistry, Jan. 15, 1995; vol. 227, issue 1-2, pp. 335-343.
Cateni, et al., "Chemoenzymatic synthesis and antimicrobial activity evaluation of monoglycosyl diglycerides," Bioorganic & Medicinal Chemistry, Pergamon, GB, vol. 15, No. 2, Dec. 12, 2006 (Dec. 12, 2006), pp. 815-826, XP005882801, ISSN: 0968-0896, DOI: 10.1016/J.BMC.2006.10.045, Scheme 2; Table 1.
Database CA [Online], Chemical Abstracts Service, Columbus, Ohio, US; 2006, Ono, Tomohiro: "Interleukin 4 formation inhibitors and their use as antiallergy, anti-inflammatory, medical, food, and cosmetic compositions", XP002740407, retrieved from STN Database accession No. 2006:440290 abstract & JP 2006 117582 A (Fancl Corporation, Japan), May 11, 2006 (May 11, 2006).
Database CA [Online] Chemical Abstracts Service, Columbus, Ohio, US; 1995, Morimoto, Akashi et al., "Anti-Tumour-Promoting Glyceroglycolipids From Thegreen Alga, *Chlorella vulgaris**", XP002740409, retrieved from STN Database accession No. 1995:931034 abstract & Morimot, Akashi et al: Anti-Tumour-Promoting Glyceroglycolipids From Thegreen Alga, *Chlorella vulgaris*, Phytochemistry, vol. 40, No. 5, Nov. 1995 (Nov. 1995), pp. 1433-1437 . . . .

(Continued)

*Primary Examiner* — Jonathan S Lau
(74) *Attorney, Agent, or Firm* — Melissa Hunter-Ensor; Scott Goncher; Greenberg Traurig, LLP

(57) ABSTRACT

The invention may provide, in part, compounds for use as antiproliferative, chemotherapeutic, antiviral, cell sensitising or adjuvant agents, and pharmaceutical compositions including the compounds. The compounds may be for use in treating diseases and disorders related to cell proliferation such as cancer, or in treating diseases and disorder which are linked to aberrant control of protein synthesis, such as cancer, viral infection, muscle wasting, autistic spectrum disorders, Alzheimer's disease, Huntingdon's disease and Parkinson's disease.

6 Claims, 20 Drawing Sheets

(56) References Cited

OTHER PUBLICATIONS

Database CA; Chemical Abstracts Sevice, Colubus, Ohio, US, 2009, Amico, Vincenzo, et al., "Bioassay-Guided Isolation of Antiproliferative Compounds from Grape (*Vitis vinifera*) Stems," XP002740408, retrieved from STN Database accession No. 2009: 160275, abstract & Amico, Vincenzo et al: Bioassay-Guided Isolation of Antiproliferative Compounds from Grape (*Vitis vinifera*) Stems, Natural Product Communications, vol. 4, No. 1, (2009) pp. 27-34.
Database CA [Online] Chemical Abstracts Service, Columbus, Ohio, US; 2002, Wang, Rong, et al., Possible Antibumor Promoters in *Spinacia oleracea* (Spinach) and Comparison of their Contents among Cultivars, XP002740406, retrieved from STN Database accession No. 2002:201598 abstract & Wang Rong, et al.: "Possible Antibumor Promoters in *Spinacia oleracea* (Spinach) and Comparison of their Contents among Cultivars," Bioscience, Biotechnology, and Biochemistry, vol. 66, No. 2, 2002, pp. 248-254 . . . .
Hou et al.. Cancer Res., 2007, 67(14), pp. 6907-6915.
Janwitayanuchit, W. et al., "Synthesis and anti-herpes simplex viral activity of monoglycosyl diglycerides," Phytochemistry, Pergamon Press, GB., vol. 64, No. 7, Dec. 1, 2003, pp. 1253-1264, XP004470666, ISSN: 0031-9422, DOI: 10.1016/J. Phytochem. Sep. 8, 2003, Scheme 1: Table 4.
Jayaprakasam Bolleddula, et al., "Tumor cell proliferation and cyclooxygenase enzyme inhibitory compounds in Amaranthus tricolor," Journal of Agricultural and Food Chemistry, American Chemical Society, US, vol. 52, No. 23, Nov. 17, 2004 (Nov. 17, 2004), pp. 6939-6943, XP002427570, ISSN: 0021-8561, DOI: 10.1021/JF048836Z, figures 1,3.
Koneni V. Sashidhara et al., "Galactolipids fromas a new class of antifilarial agents against human lymphatic filarial parasite," European Journal of Medicinal Chemistry, Editions Scientifique Elsevier, Paris, FR, vol. 50, Jan. 29, 2012 (Jan. 29, 2012), pp. 230-235, XP28471841, ISSN: 0223-5234, DOI: 10.1016/J.EJMECH. 2012. 01.057 [retrieved on Feb. 3, 2012], Fig. 1; Table 4.
Matsui, Y et al., "Structure and activity relationship of monogalactosyl diacylglycerols, which selectively inhibited in vitro mammalian replicative DNA polymerase activity in human cancer cell growth," Cancer Letters, New York, NY, US., vol. 283, No. 1., Sep. 28, 2009, pp. 101-107, XP026337097; ISSN: 0304-3835, DOI: 10.1016/J. CANLET. 2009.03.029 [retrieved on Apr. 18, 2009] Fig.1; Table 2.
Murakami A, et al., "Glycerglycolipids from Citrus hystrix, a traditional herb in Thailand, potently inhibit the tumor-poromoting activity of 12-0-tetradecanoylphorbol 13-acetate in mouse skin," Journal of Agricultural and Food Chemistry, American Chemical Society, US, vol. 43, No. 10, Jan. 1, 1995 (Jan. 1, 1995), pp. 2779-2783, XP002100385, ISSN: 0021-8561, DOI: 10.1021/ JF00058A043, Fig. 1, 2; Tab. 3.
Bates et al., "An Approach to Pseudomonic Acids from Acetylenic Precursors: Synthesis of 2-(Hydroxymethyl)-3-butyn-1-ol," The Journal of Organic Chemistry, 1986, vol. 51, No. 14, pp. 2637-2641.

Second Office Action issued in corresponding Chinese Patent Application No. 201580030017.4, dated Jun. 2, 2020 (7 pages).
M Aoyagi, et al, "Human cytomegalovirus UL69 protein facilitates translation by associating with the mRNA cap-binding complex and excluding 4EBP1" PNAS 107 (2010): 2640-2645.
P Bitterman, et al, "Attacking a Nexus of the Oncogenic Circuitry by Reversing Aberrant eIF4F-Mediated Translation" Mol. Can. Ther. 11 (2012): 1051-1061.
S Blagden, et al, "The biological and therapeutic relevance of mRNA translation in cancer" Nature 8 (2011): 280-291.
M Bordelau, et al, "RNA-Mediated Sequestration of the RNA Helicase eIF4A by Pateamine A Inhibits Translation Initiation" Chemistry & Biology 13 (2006): 1287-1295.
A Bottley, et al, "eIF4A Inhibition Allows Translational Regulation of mRNAs Encoding Proteins Involved in Alzheimer's Disease" PLoS One 5 (2010): e13030.
L Boussemart, et al, "eIF4F is a nexus of resistance to anti-BRAF and anti-MEK cancer therapies" Nature 105 (2014): 105 (doi:10,1038/ nautre13572).
R Cencic, et al, "Blocking eIF4E-EIF4G Interaction as a Strategy to Impair Coronavirus Replication" J Virol. 85 (2011): 6381-6389.
K Daughenbaugh, et al, "The genome-linked protein VPg of the Norwalk virus binds EIF3, suggesting its role in translation initiation complex recruitment" EMBO 22 (2013): 2852-2859.
K Daughenbaugh, et al, "VPg of murine norovirus binds translation initiation factors in infected cells" Virology Journal 3 (2006): 33 (http://www.virologyj.com/content/3/1/33).
S de Breyne, et al, "In vitro studies reveal that different modes of initiation on HIV-1 mRNA have different levels of requirement for eukaryotic initiation factor 4F" FEBS Journal 279 (2012): 3098-3111.
C Gkogkas, et al, "Autism-related deficits via dysregulated eIF4E-dependent translational control" Nature 493 (2013): 371-377.
N Locker, et al, "A conserved structure within the HIV gag open reading frame that controls translation initiation directly recruits the 40S subunit and EIF3" Nucleic Acids Research 39 (2011): 2367-2377.
J Rocha-Pereira, et al, "Targeting Norovirus: Strategies for the Discovery of new antiviral Drugs." InTech 7 (2012): 121-150.
H Saffran, et al, "Evidence for Translational Regulation by the Herpes Simplex Virus Virion Host Shutoff Protein" J Virol 84 (2010): 6041-6049.
Y Svitkin, et al, "The requirement for eukaryotic initiation factor 4A (eIF4A) in translation is in direct proportion to the degree of mRNA 5' secondary structure" RNA 7 (2001): 382-394.
D Walsh, "Manipulation of the host translation initiation complex eIF4F by DNA viruses" Biochem. Soc. Trans. 38 (2010): 1511-1516 (doi:10.1042/BST0381511).
A Wolfe, et al, "RNA G-quadruplexes cause eIF4A-dependent oncogene translation in cancer" Nature 4 (2014): 65-70 (doi:10,1038/ nature13485).
E Yángüez, et al, "Functional impairment of EIF4A and EIF4G factors correlates with inhibition of influenza virus mRNA translation" Virology 413 (2011): 93-102.

\* cited by examiner

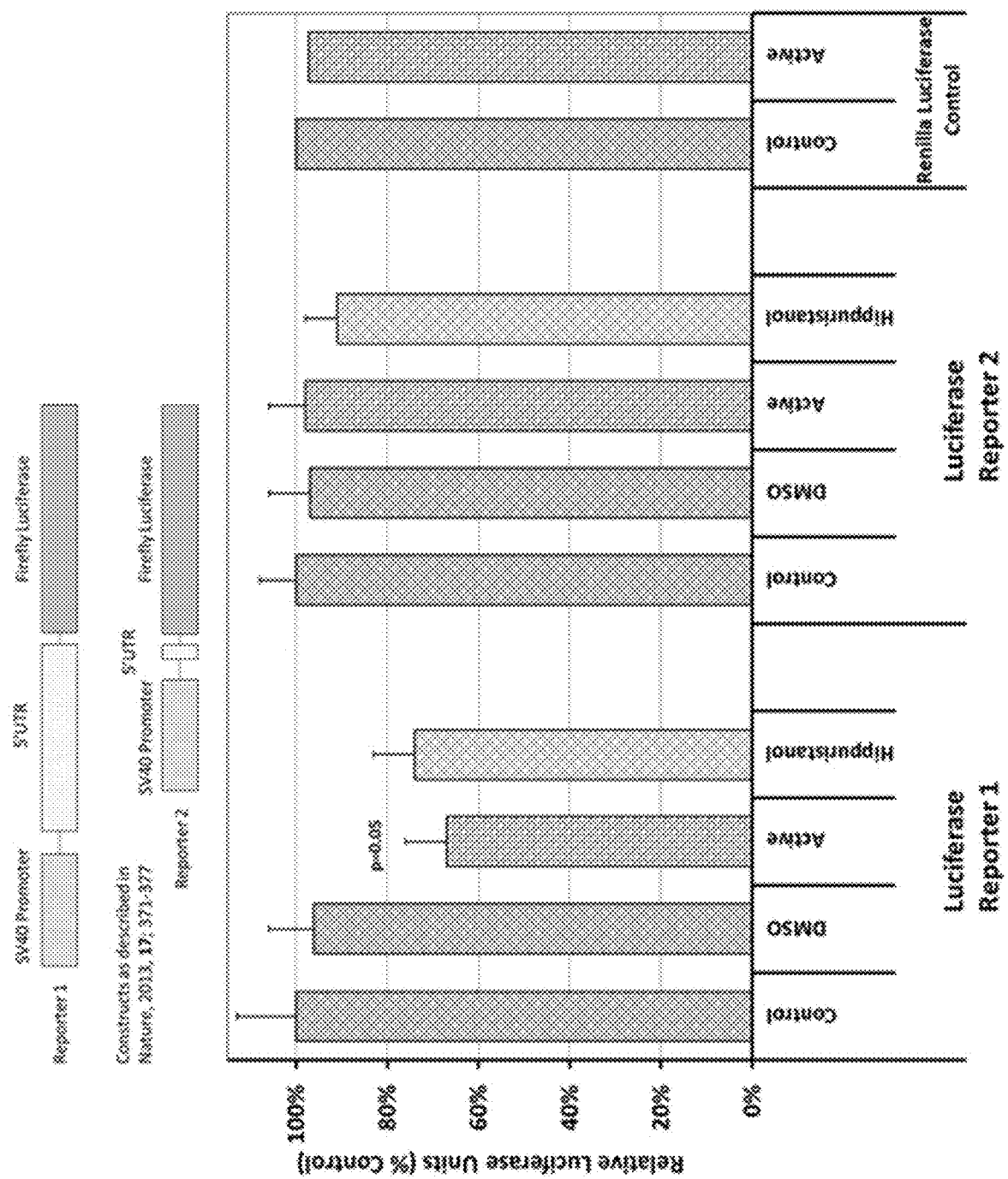

Figure 10
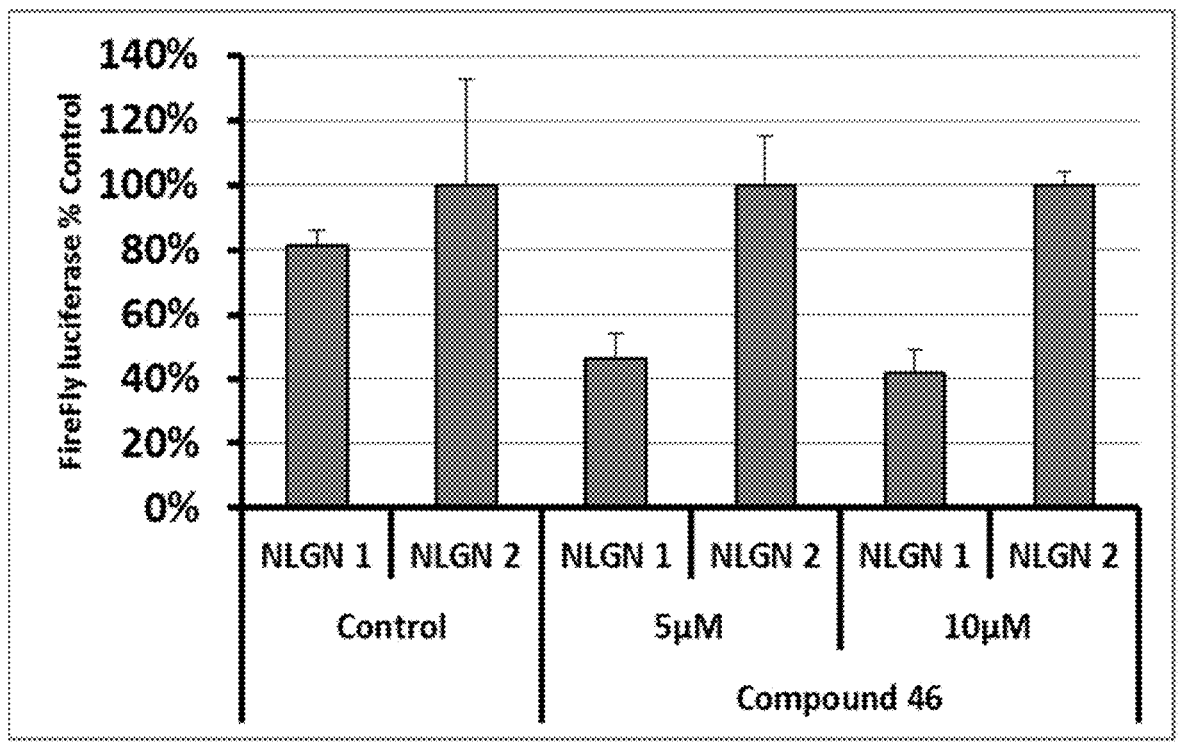
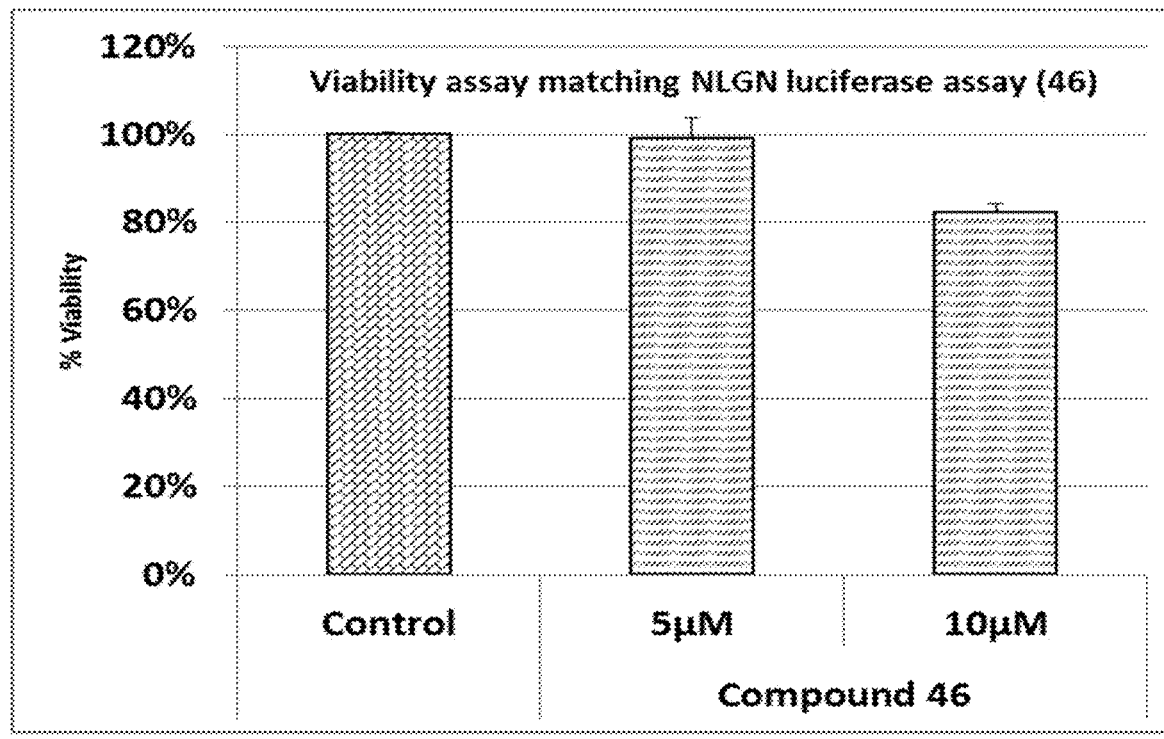

Figure 15
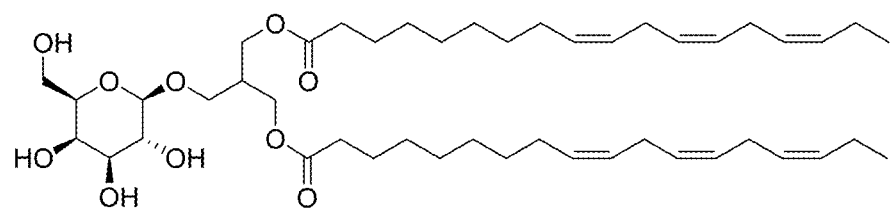
Compound 46
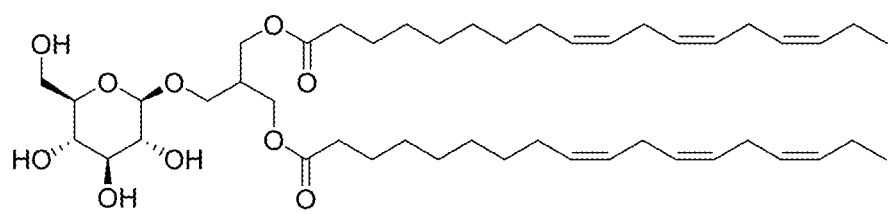
Compound 99
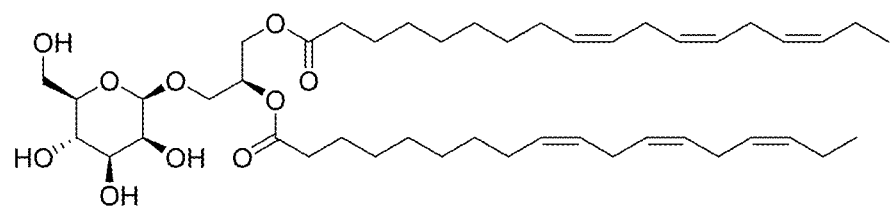
Compound 123

Figure 16

| | | Cell viability after treatment (% control) | | | 20μM active assayed for |
|---|---|---|---|---|---|
| | Compound identifier | 20μM | 40μM | 80μM | Additive or synergistic effects in combination with chemotherapeutic |
| | | | | | (2μM Cisplatin) |
| | 99 | 1% | 0% | 1% | Yes |
| | 218 | 1% | 0% | 0% | Yes |
| | 139 | 3% | 0% | 0% | Yes |
| | 184 | 3% | 1% | 1% | Yes |
| | 123 | 5% | 0% | 0% | Yes |
| | 180 | 6% | 0% | 1% | Yes |
| | 124 | 11% | 0% | 0% | Yes |
| | 159 | 17% | 0% | 0% | |

Figure 16 continued

| Structure | # | | | | Active |
|---|---|---|---|---|---|
| (glycolipid structure) | 38* | 21% | 3% | 4% | Yes |
| (glycolipid structure) | 215 | 37% | 7% | 5% | |
| (glycolipid structure) | 146 | 38% | 21% | 7% | |
| (glycolipid structure) | 122 | 40% | 0% | 0% | Yes |
| (glycolipid structure) | 119 | 49% | 20% | 4% | Yes |
| (glycolipid structure) | 62 | 54% | 30% | 4% | Yes |
| (glycolipid structure) | 120 | 54% | 16% | 4% | Yes |
| (glycolipid structure) | 46 | 70% | 18% | 4% | Yes |

Figure 17

| | Compound identifier | 20μM | 40μM | 80μM | Additive or synergistic effects in combination with chemotherapeutic | |
|---|---|---|---|---|---|---|
| | | | | | (2μM Cisplatin) | Rank Synergy |
| | 61 | 95% | 104% | 105% | Yes | 1st |
| | 57 | 77% | 76% | 75% | Yes | 2nd |
| | 60 | 86% | 93% | 102% | Yes | 3rd |
| | 56 | 78% | 76% | 59% | Yes | 4th |
| | 154 | 86% | 51% | 10% | Yes | 5th |
| | 58 | 90% | 72% | 51% | Yes | 6th |

GLYCOLIPIDS AND PHARMACEUTICAL COMPOSITIONS THEREOF FOR USE IN THERAPY

CROSS REFERENCE TO RELATED APPLICATIONS

This application claims the benefit and is a continuation of U.S. application Ser. No. 15/301,264, filed Sep. 30, 2016, which is a US National Phase application under 35 U.S.C. 371 of International Application No. PCT/GB2015/051068, filed Apr. 7, 2015, designating the U.S. and published in English, which claims the benefit of priority of GB Application No. 1406172.5, filed Apr. 4, 2014, the entire contents of which are incorporated herein by reference in their entirety.

BACKGROUND

The present invention relates to compounds for use as one or more of an antiproliferative agent, a chemotherapeutic agent, an adjuvant, and antiviral agent and a cell sensitising agent. Preferably the compounds are inhibitors of protein translation.

The disruption of one or more steps in the control of protein synthesis has been associated with alterations in the cell cycle and/or regulation of cell growth. Evidence supports the concept that some translation factors are proto-oncogenes and proteins involved in translation pathways can act as key regulators of malignant progression (Hershey et al, 2000 Translational Control and Cancer, Cold Spring Harbor Laboratory Press, Cold Spring Harbor). Cancer cells generally show higher rates of protein synthesis compared to normal cells. Accordingly, deregulation of protein synthesis is emerging as a major contributor to cancer progression. Over expression of certain translation factors can lead to malignant transformation and many of the components of the translation pathways are over-expressed in cancer. A number of clinically relevant in-vivo experiments have demonstrated that inhibition of translation may be relevant for the treatment of a range of cancer types e.g. adult T-cell leukaemia, lung, breast and cervical cancer. The requirement for elevated levels of protein synthesis is a common feature of cancer cell growth; therefore it is highly likely that a wider broad spectrum of cancer types will also be amenable to treatment with this class of inhibitor.

Inhibitors of translation have shown remarkable promise for use as an adjuvant therapy in combination with chemotherapeutics such as Doxorubicin™. Rapidly proliferating tumour types such as MCF-7 breast cancer cells require relatively more protein synthesis than slower growing cancer cells such as A549 lung carcinoma cells. These slow-growing cancer cell types have relatively higher patient mortality rates five years after diagnosis due to chemoresistance to common in clinic chemotherapeutics agents such as Cisplatin™. Research has shown that cell types such as A549 lung carcinoma or SKOV3 ovarian cancer cells derive resistance to platinum based therapies through the aberrant translation of specific proteins e.g. LARP1. Experimental evidence also suggests that endogenous inhibitors of protein synthesis such as programme cell death 4 (PDCD4) modulate sensitivity to Cisplatin™ and that the levels of these endogenous inhibitors significantly correlate with disease-free survival of ovarian cancer patients.

Therapeutic modulation of protein translation by inhibition of the eIF4A RNA helicase' is a proven target for the treatment for a broad range of cancer types. Regulation of protein synthesis at the level of translation initiation (eIF4F complex containing eIF4A) is particularly important in cancer cell growth because they are metabolically highly active. This rapid growth places a heavy demand on the protein synthesis machinery. Additionally cancer cells often produce proteins that provide resistance to commonly used chemotherapeutic drugs and this resistance is determined by selective translation of key proteins i.e. dependant on eIF4A. De novo or acquired resistance to platinum chemotherapy is the leading cause of death in some cancers e.g. Ovarian, and high impact research identifies that this chemo-resistance is due to the aberrant translation of key proteins (e.g. Boussemart et al 2014, Nature, ahead of print doi:10.1038/nature13572; Wolf et al. 2014 *Nature*, ahead of print doi: 10.1038/nature13485); also see reviews by Blagden and Willis, 2011 Nature Oncology Reviews, 8:280-291; Bitterman and Polunovsky 2012, *Molecular Cancer Theraputics*, 11: 1051-1061).

The therapeutic modulation of mRNA translation; inhibition of eIF4A is therefore an excellent and well published intervention point for the treatment of a range of different cancer types; enabling a selective treatment targeted to the biology of the cancer cell. Initiation of translation is a point of convergence for multiple aberrant signalling cascades, and represents a logical approach for targeting chemotherapy-resistant cancer cells (cancer types include but are not limited to ovarian, lung, breast, leukaemia, pancreatic, kidney).

There is now compelling evidence that aberrant control of protein synthesis is linked to the progression of a range of other conditions and illnesses. Chronic conditions such as muscle wasting, autistic spectrum disorders, Alzheimer's disease, Huntingdon's disease and Parkinson's disease all share similar patterns of deregulation of protein synthesis and a number of research studies conclude that pharmacological agents targeting the protein synthesis machinery are one potential route to treatment for such conditions. Further experimental evidence also indicates that inhibitors of translation or compounds which act to modify or alter protein synthesis present an attractive opportunity as broad acting antivirals e.g. hippuristanol has been shown to effectively disrupt the control of HIV virus translation. Indications from studies using inhibitors of protein synthesis such as hippuristanol, suggest this to be a relatively non-toxic treatment option.

Herpes simplex virus HSV-1 has been shown to stimulate eIF4E phosphorylation and eIF4F complex formation in resting primary human cells. It is also known that the VHS protein (virion host shut-off), an HSV viral endonuclease, selectively associates with eIF4A and eIF4H during the viral life cycle. In addition to degrading host mRNAs, VHS is thought to play a role in regulating the temporal pattern of viral mRNA expression, through enhancement of viral RNA translation. VHS associates with eIF4A/eIF4H and, despite its endonuclease activity, this association with eIF4A has been shown to enhance translation from viral IRES (internal ribosome entry site) elements and sequences within HSV-1 5'-UTRs (Saffran et al, 2010. *J. Virol.* 84, 6041-6049; Reviewed by Walsh, D. (2010). *Biochem. Soc. Trans.* 38, 1511-1516.).

With regard to the human immunodeficiency virus (HIV), the relative expression of the two isoforms p55 and p40 of HIV-1 Gag proteins is highly dependent on the correct functioning of the translation initiation complex. The highly structured 5'-UTR of the viral p55 gene has been shown to tightly control of expression through a requirement of the eIF4F complex, especially the RNA helicase eIF4A (de Breyne et al, 2012. *FEBS J.* 279, 3098-3111). Additional research performed using the known inhibitor of eIF4A hippuristanol has evaluated the requirement for eIF4A in the correct translation of HIV proteins. Increasing amounts of hippuristanol inhibits the translation of the three Gag isoforms in a similar dose-response manner thus confirming a functional requirement for eIF4A in the HIV life-cycle (Locker et al, 2010. *Nucleic Acids Res.* 39, 2367-2377). Recent work by Plank et al, (2014. Vol. 2, Iss. 1) confirmed that Hippuristanol treatment of HeLa cells transfected with HIV-1 leader constructs inhibited IRES activity, with IC50 values in a drug-gable range (163 to 296 nM). Taken together, these results confirm that eIF4A is important in the HIV life cycle and that eIF4A presents an attractive new therapeutic target for this virus.

Inhibitors of eIF4A have been shown to have value in the prevention of influenza viral replication (e.g. WO 2013152299 A2) Recent research has demonstrated the functional impairment of eIF4A correlates with inhibition of influenza virus mRNA translation and protein synthesis, and that this helicase is essential for viral translation (data obtained from both in in vivo and in vitro analysis) (Yangiez et al, 2011. *Virology.* 413, 93-102). Viral mRNAs have been shown not to contain cis-acting signals that may mediate eIF4A independent translation and it is also known that trans-acting viral proteins cannot replace the function of mammalian eIF4A. Therefore inhibition of eIF4A is an attractive target to prevent the propagation and replication of the influenza virus in infected cells.

Coronaviruses (e.g. Human Coronaviruses) are recognized to cause up to a third of common colds and are also the cause of severe viral infections such as SARS. Coronavirus replication involves the generation of mRNAs with capped 5'UTRs. Coronavirus 5'UTRs e.g. those identified from SARS isolates, are relatively well conserved and the full sequence forms a complex secondary structure containing four stem-loop domains. As 5'UTR secondary structure directly correlates with the requirement for eIF4A, it is not surprising that eIF4A is considered a therapeutic target for coronavirus infection.

The translation of most of the coronaviral mRNAs is thought to be cap dependent and requires a functional translation initiation complex eukaryotic initiation factor 4F (eIF4F) (Cencic et al, 2011. *J Virol.* 85,6381-6389). Inhibition of translation with the eIF4A inhibitors hippuristanol or silvestrol caused a 10- to 100-fold reduction in infectious coronavirus virus titers released from infected cells (Cencic et al, 2011. *J Virol.* 85,6381-6389). This virus has been proven to be dependent on eIF4A and a significant reduction in viral progeny has been observed upon the inhibition of eIF4A (Cencic et al, 2011. *J Virol.* 85,6381-6389).

Rhinoviruses are the most common viral infective agents in humans and are the major cause of the common cold. Internal ribosomal entry site elements of poliovirus (PV), human rhinovirus (HRV) and encephalomyocarditis virus (EMCV) foot-and-mouth disease virus (FMDV) groups are all inhibited by disruptive mutations to the eIF4A protein (Svitkin et al, 2001. *RNA.* 7, 382-394). These viruses are therefore dependant on eIF4A activity.

HCMV (human cytomegalovirus) is a herpes virus that can have serious and life threatening consequences for immunocompromised patients. As HCMV infection progresses, the abundance of core eIF4F components (eIF4A is part of the eIF4F complex) greatly increases (Walsh et al, 2005. *J. Virol.* 79, 8057-8064). In addition, HCMV UL69, homologous with the HSV-1 ICP27 protein, associates with eIF4A (Aoyagi et al, 2010. *Proc. Natl. Acad. Sci. U.S.A.* 107, 2640-2645). Pateamine A, a known inhibitor of eIF4a inhibits the replication of HCMV (see patent WO 2013152299 A2). Disrupting eIF4A activity presents a therapeutic target as an antiviral for HCMV.

There is good evidence that the initiation of translation of norovirus proteins is dependent on the interaction of the VPg with the translation initiation complex (Daughenbaugh et al, 2003. *EMBO J.* 11, 2852-2859; Daughenbaughet et al, 2006. *Virol J.* 23, 3-33). Panteamine A, a proven inhibitor of eIF4A, has the potential to interfer with VPg/eIF4F complex, since it disrupts the helicase/NTPase activity of eIF4A, dysregulating its function within the eIF4F complex (Bordeleau et al, 2006. *Chem Biol.* 13, 1287-1295). Virologists suggest that inhibitors of eIF4A could therefore be exploited as antivirals for norovirus due to this dependency (See Rocha-Pereira and Nascimento, 2012 Targeting Norovirus: Strategies for the Discovery of New Antiviral Drugs, Antiviral Drugs—Aspects of Clinical Use and Recent Advances, Dr. Patrick Arbuthnot (Ed.), ISBN: 978-953-51-0256-4, InTech).

Recent high impact research into the cause of ASD has identified that dysregulation of protein synthesis in neuronal cells at the point of translation initiation is a primary driver of ASD symptoms (Gkogkas et al, 2013 *Nature,* 2013, 493:371-377; Santini et al, *Nature,* 2013, 493:411-415).

Work by the Sonenberg lab (Gkogkas et al, 2013. *Nature,* 493, 371-377) demonstrated a direct link between ASD and the relative translation of two neuroligins; these are proteins which mediate new connections between neuronal cells and regulate the composition of neurotransmitter receptors. This new research identifies that the ratio of the synthesis of these two proteins is selectively determined by the activity of the translation initiation complex and that dysregulation of synthesis drives or promotes the symptoms of ASD. Importantly it is the relative synthesis of neuroligin 1 (NLGN1) protein that is incorrectly regulated; therefore selective control of NLGN1 has been demonstrated to be a viable treatment option for ASD.

In the Gkogkas et al (2013. *Nature,* 493, 371-377) model therapeutic intervention to regulate NLGN1 is mediated via inhibition of eIF4E, a key protein in the translation initiation complex. However, the helicase eIF4A represents an additional and more selective new target for the control of NLGN1 synthesis; a target to elevate the symptoms of ASD. The eIF4A helicase functions to unwind long, complex and structured 5'UTRs; this is required before protein synthesis can begin. Inhibiting eIF4A selectively reduces the synthesis of proteins with greater 5'UTR secondary structure or longer length, while not inhibiting those with short 5'UTRs or unstructured UTRs. Treating cells with the coral derived inhibitor of eIF4A, hippuristanol, results selective inhibition determined by features present within the 5'UTR (e.g. Bottley et al, 2010 PLOS One, 5(9): e13030).

Although the need for chemical modifiers of translation has been well established, most current small molecule inhibitors, such as hippuristanol, are sourced from rare marine corals or sponges and prove difficult to synthesise in any meaningful quantity. Such molecules have however been successfully used to provide in-vivo evidence that this class of inhibitor is a likely successful strategy option for use in the clinic, however these molecules are source limited and as such not an available option for clinical use.

SUMMARY

An aim of the present invention is to provide novel inhibitors of protein translation, such as inhibitors of eukaryotic ribosome activity, which could be used as antiproliferative agents, chemotherapeutic agents, antivirals, cell sensitising agents and/or adjuvants. An inhibitor of eukaryotic ribosome activity may selectively inhibit eIF4A-dependent or independent translation initiation.

The invention may provide, in part, compounds for use as antiproliferative, chemotherapeutic, antiviral, cell sensitising or adjuvant agents, and pharmaceutical compositions including the compounds. The compounds may be for use in treating diseases and disorders related to cell proliferation such as cancer, or in treating diseases and disorders which are linked to aberrant control of protein synthesis, such as cancer, viral infection, muscle wasting, autistic spectrum disorders, Alzheimer's disease, Huntingdon's disease and Parkinson's disease.

According to a first aspect the invention provides a compound of Formula I:

R1-L1-C(A)(A')—CH$_2$-L2-R2    (I)

or a pharmaceutically acceptable salt thereof,
wherein:
R1 is selected from a carbohydrate group or derivative thereof, hydrogen, a C1-C24 alkyl or a C1-C24 derivative of an alkyl group, a C2-C24 alkenyl or a C2-C24 derivative of an alkenyl group, and a C2-C24 alkynyl group or a C2-C24 derivative of an alkynyl group;
L1 is a linking group;
L2 is a linking group;
R2 is selected from hydrogen, a C1-C24 alkyl or a C1-C24 derivative of an alkyl group, a C2-C24 alkenyl or a C2-C24 derivative of an alkenyl group, and a C2-C24 alkynyl group or a C2-C24 derivative of an alkynyl group;
A is selected from hydrogen and a C1-C6 alkyl group;
A' is selected from hydrogen, a C1-C6 alkyl group, and L3-R3;
wherein
L3 is a linking group; and
R3 is selected from hydrogen, a C1-C24 alkyl or a C1-C24 derivative of an alkyl group, a C2-C24 alkenyl or a C2-C24 derivative of an alkenyl group, and a C2-C24 alkynyl group or a C2-C24 derivative of an alkynyl group;
and wherein if A' is not L3-R3, then R2 is a C10-C24 alkyl or a C10-C24 derivative of an alkyl group, a C10-C24 alkenyl or a C10-C24 derivative of an alkenyl group, or a C10-C24 alkynyl group or a C10-C24 derivative of an alkynyl group
and wherein if A' is L3-R3, then one or both of R2 and R3 are a C10-C24 alkyl or a C10-C24 derivative of an alkyl group, a C10-C24 alkenyl or a C10-C24 derivative of an alkenyl group, or a C10-C24 alkynyl group or a C10-C24 derivative of an alkynyl group.

In one embodiment, the compound of Formula I is not:

In general, in the embodiments where A' is L3-R3, it may be preferred that the L3 linking group does not connect with the carbon atom to which it is attached by an O group. Thus whilst the L3 group may optionally contain an O group, in one embodiment this is not be the group that directly connects with the carbon atom in Formula I to which the L3 linking group is attached.

For example, it may be preferred that the L3 linking group does not connect with the carbon atom to which it is attached by a heteroatom. Instead, it may be preferred that there is a C—C bond serving to connect the L3 linking group with the carbon atom in Formula I to which it is attached.

DETAILED DESCRIPTION

In one embodiment, L3 is a linking group that is selected from:
(i) a C1-C6 alkylene linking group, e.g. a C1-C5 alkylene linking group, such as methylene or ethylene;
(ii) an ether linking group —(CH$_2$)$_p$O(CH$_2$)$_q$—, where p and q independently represent an integer of from 1 to 3, and p+q equals 4 or less;
(iii) a C2-C4 alkenylene linking group such as ethenylene;
(iv) an ester linking group —(CH$_2$)$_p$C(=O)O(CH$_2$)$_q$—, where p and q each independently represent an integer of from 0 to 3, and p+q equals 4 or less; or an ester linking group —(CH$_2$)$_p$OC(=O)(CH$_2$)$_q$—, where p represents an integer of from 1 to 3, q represents an integer of from 0 to 3 and p+q equals 4 or less; or an amido linking group —(CH$_2$)$_p$C(=O)NRz(CH$_2$)$_q$—, where p and q independently represent an integer of from 0 to 3, and p+q equals 4 or less, and Rz is H or C1-C4 alkyl; or an amido linking group —(CH$_2$)$_p$NRzC(=O)(CH$_2$)$_q$—, where p represents an integer of from 1 to 3, q represents an integer of from 0 to 3 and p+q equals 4 or less and Rz is H or C1-C4 alkyl;
(v) an amine linker of formula —RxN(Rz)Ry-, for example wherein Rx and Ry are C1-C4 alkylene, e.g. C1 or C2 alkylene, and Rz is H or C1-C4 alkyl, e.g. C1 or C2 alkyl;
(vi) a thioether linker —(CH$_2$)$_p$S(CH$_2$)$_q$—, where p represents an integer of from 1 to 3, q represents an integer of from 0 to 3 and p+q equals 4 or less.

In one embodiment, L3 is a linking group that is selected from:
(i) a C1-C4 alkylene linking group such as methylene or ethylene;
(ii) an ether linking group —(CH$_2$)$_p$O(CH$_2$)$_q$—, where p and q independently represent an integer of from 1 to 3, and p+q equals 4 or less;
(iii) a C2-C4 alkenylene linking group such as ethenylene;
(iv) an ester linking group —(CH$_2$)$_p$C(=O)O(CH$_2$)$_q$—, where p and q each independently represent an integer of from 0 to 3, and p+q equals 4 or less; or an ester linking group —(CH$_2$)$_p$OC(=O)(CH$_2$)$_q$—, where p represents an integer of from 1 to 3, q represents an

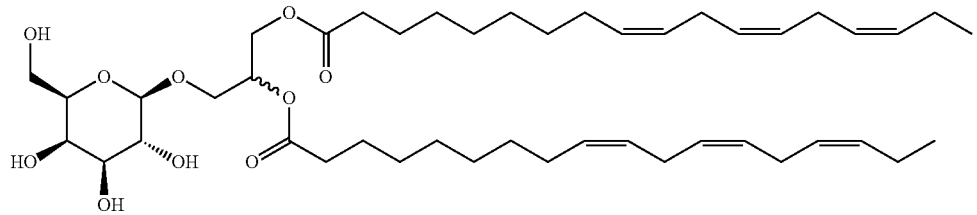 [SMILES: CC/C=C\C/C=C\C/C=C\CCCCCCCC(=O)OCC(CO[C@@H]1O[C@H](CO)[C@H](O)[C@H](O)[C@H]1O)OC(=O)CCCCCCC/C=C\C/C=C\C/C=C\CC]

integer of from 0 to 3 and p+q equals 4 or less; or an amido linking group —(CH$_2$)$_p$C(=O)NRz(CH$_2$)$_q$—, where p and q independently represent an integer of from 0 to 3, and p+q equals 4 or less, and Rz is H or C1-C3 alkyl; or an amido linking group —(CH$_2$)$_p$NRzC(=O)(CH$_2$)$_q$—, where p represents an integer of from 1 to 3, q represents an integer of from 0 to 3 and p+q equals 4 or less and Rz is H or C1-C3 alkyl;

(v) an amine linker of formula —RxN(Rz)Ry-, for example wherein Rx and Ry are C1-C4 alkylene, e.g. C1 or C2 alkylene, and Rz is H or C1-C4 alkyl, e.g. C1 or C2 alkyl;

(vi) a thioether linker —(CH$_2$)$_p$S(CH$_2$)$_q$—, where p and q independently represent an integer of from 1 to 3, and p+q equals 4 or less.

In some embodiments there are no asymmetric carbon atoms (no centres of chirality) present in the compound within the portion —C(A)(A')-CH$_2$-L2-R2. There may, however, be asymmetric carbon atoms (centres of chirality) within the R1-L1- portion of the compound. In particular, there may be asymmetric carbon atoms (centres of chirality) within R1 when this is a carbohydrate group.

In the embodiments where A' is L3-R3, it may be preferred that -L3-R3 is equivalent to —CH$_2$-L2-R2.

In one embodiment, A' is L3-R3, and both of R2 and R3 are a C10-C24 alkyl or a C10-C24 derivative of an alkyl group, a C10-C24 alkenyl or a C10-C24 derivative of an alkenyl group, or a C10-C24 alkynyl group or a C10-C24 derivative of an alkynyl group.

In the embodiments where A' is not L3-R3, it may be preferred that A and A' are the same.

In one embodiment, A' is not L3-R3, and A and A' are both the same C1-C6 alkyl group, e.g. both are methyl, or both are ethyl, or both are n-propyl.

For those compounds where there are no asymmetric carbon atoms (no centres of chirality) present in the compound within the portion —C(A)(A')-CH$_2$-L2-R2, the compound may have improved solubility properties, which in turn can make the compound easier to work with and easier to formulate as a pharmaceutical or neutraceutical composition.

Preferably R1 is not hydrogen. More preferably R1 is a carbohydrate group or derivative thereof. In one embodiment, the R1 comprises a sugar group and the sugar is selected from galactose, glucose and mannose and derivatives thereof.

In one embodiment, the compound does not include a glycoside linkage. This can result in a product that is degraded more slowly as it does not have an anomeric position at which it can be readily cleaved. A product that is more difficult to cleave enzymatically will be more stable. Options for the linking group L1 are set out below and it will be seen that these include linking groups such as alkylene groups which are therefore non-glycosidic.

In the compound of Formula I it is preferred that one or more C=C double bond is contained within the —C(A)(A')-CH$_2$-L2-R2 part of the compound, such as two or more C=C double bonds, or three or more C=C double bonds. There may, for example, be from one to eight C=C double bonds, such as from two to eight C=C double bonds, or from two to six C=C double bonds.

In one embodiment, the R2 group contains one or two or three (or more) C=C double bonds.

In one embodiment, both the A' group and the R2 group contain one or more C=C double bond, e.g. it may be that the A' group and the R2 group both independently contain one or two or three (or more) C=C double bonds.

Preferably the (or each) C=C double bond that is contained within the —C(A)(A')-CH$_2$-L2-R2 part of the compound is located four or more atoms in the chain away from the L1 group, such as five or more atoms in the chain away from the L1 group, e.g. six or more atoms in the chain away from the L1 group or seven or more atoms in the chain away from the L1 group or eight or more atoms in the chain away from the L1 group.

It is preferred that there is one or more C=C double bond that is located more than six atoms but less than 17 atoms in the chain away from the L1 group, such as more than six atoms but less than 16 atoms in the chain away from the L1 group, e.g. more than six atoms but less than 15 atoms (or more than six but less than 14 atoms) in the chain away from the L1 group.

It may be that there are two or more C=C double bonds that are located more than six atoms but less than 17 atoms in the chain away from the L1 group, such as more than six atoms but less than 16 atoms in the chain away from the L1 group, e.g. more than six atoms but less than 15 atoms (or more than six but less than 14 atoms) in the chain away from the L1 group.

It may be that there are two or more C=C double bonds that are located more than 8 atoms but less than 17 atoms in the chain away from the L1 group, such as more than 9 atoms but less than 17 atoms in the chain away from the L1 group, e.g. more than 10 atoms but less than 17 atoms (or more than 11 but less than 17 atoms) in the chain away from the L1 group.

In one embodiment, both the A' group and the R2 group contain one or more C=C double bond that is located more than six atoms but less than 17 atoms in the chain away from the L1 group, e.g. the A' group may contain one or two (or more) C=C double bonds that are located more than six atoms but less than 17 atoms in the chain away from the L1 group and the R2 group may contain one or two (or more) C=C double bonds that are located more than six atoms but less than 17 atoms in the chain away from the L1 group. In one embodiment the A' group may contain one or two (or more) C=C double bonds that are located more than 7 atoms but less than 17 atoms in the chain away from the L1 group and the R2 group may contain one or two (or more) C=C double bonds that are located more than 7 atoms but less than 17 atoms in the chain away from the L1 group. In one embodiment the A' group may contain one or two (or more) C=C double bonds that are located more than 10 atoms but less than 17 atoms in the chain away from the L1 group and the R2 group may contain one or two (or more) C=C double bonds that are located more than 10 atoms but less than 17 atoms in the chain away from the L1 group.

Optionally there may be one or more C=C double bond that is located more than 13 atoms in the chain away from the L1 group, such as more than 14 atoms in the chain away from the L1 group, e.g. more than 15 atoms, or more than 16 atoms, or more than 17 atoms, in the chain away from the L1 group.

It may optionally be that there are two or more C=C double bonds that are located more than 13 atoms in the chain away from the L1 group, such as more than 14 atoms in the chain away from the L1 group, e.g. more than 15 atoms, or more than 16 atoms, or more than 17 atoms, in the chain away from the L1 group.

In one embodiment, both the A' group and the R2 group contain one or more C=C double bond that is located more than 13 atoms (or more than 14 atoms) in the chain away from the L1 group, e.g. the A' group may contain one or two (or more) C=C double bonds that are located more than more than 13 atoms (or more than 14 atoms) in the chain away from the L1 group and the R2 group may contain one or two (or more) C=C double bonds that are located more than 13 atoms (or more than 14 atoms) in the chain away from the L1 group.

In one embodiment, both the A' group and the R2 group contain one or more C=C double bond, e.g. the A' group may contain from one to three (or more) C=C double bonds and the R2 group may contain from one to three (or more) C=C double bonds.

In one embodiment, A is not hydrogen and A' is not hydrogen. This can result in a product that is more hindered and therefore more stable. This is especially the case when L2 is an ester linkage, such that the ester can be seen as one derived from a tertiary alcohol, which can result in a product that is more hindered and more difficult to cleave enzymatically, and therefore more stable.

If A' is not L3-R3, then in one embodiment it can be preferred that R2 is a group that contains one or more C=C double bond, such as two or more C=C double bonds, or three or more C=C double bonds. For example, it may be that R2 is a C10-C24 derivative of an alkyl group, where the alkyl group is substituted with one or more substituent groups and wherein said one or more substituent groups between them comprise one or more C=C double bond, such as two or more C=C double bonds, or three or more C=C double bonds. It might alternatively be that R2 is a C10-C24 alkenyl group, which will of course contain one or more C=C double bond, and may contain two or more C=C double bonds or three or more C=C double bonds. It might alternatively be that R2 is a C10-C24 derivative of an alkenyl group; the alkenyl group will of course contain one or more C=C double bond, and may contain two or more C=C double bonds or three or more C=C double bonds, and the alkenyl group may optionally be substituted with one or more substituent groups wherein said one or more substituent groups between them comprise one or more C=C double bond.

In the embodiment where A' is L3-R3, then preferably one or both of R2 and R3 is a group that contains one or more C=C double bond, such as two or more C=C double bonds or three or more C=C double bonds. R2 and/or R3 could be a C10-C24 derivative of an alkyl group, where the alkyl group is substituted with one or more substituent groups and wherein said one or more substituent groups between them comprise one or more C=C double bond, such as two or more C=C double bonds, or three or more C=C double bonds. R2 and/or R3 could be a C10-C24 alkenyl group, which will of course contain one or more C=C double bond, and may contain two or more C=C double bonds or three or more C=C double bonds. R2 and/or R3 could be a C10-C24 derivative of an alkenyl group; the alkenyl group will of course contain one or more C=C double bond, and may contain two or more C=C double bonds or three or more C=C double bonds, and the alkenyl group may optionally be substituted with one or more substituent groups wherein said one or more substituent groups between them comprise one or more C=C double bond.

It may be that R2 and R3 each contain one or more C=C double bond, such as two or more C=C double bonds or three or more C=C double bonds. R2 and R3 may be the same or may be different—and thus there will not necessarily be an even number of C=C double bonds present.

In some preferred embodiments, two or more (e.g. three or more) of the following apply:
  a) R1 is a carbohydrate group or derivative thereof;
  b) the compound does not include a glycoside linkage;
  c) two or more C=C double bonds are contained within the —C(A)(A')-CH$_2$-L2-R2 part of the compound;
  d) there are no asymmetric carbon atoms present in the compound within the portion —C(A)(A')-CH$_2$-L2-R2.

In some preferred embodiments, two or more (e.g. three or more) of the following apply:
  a) R1 is a carbohydrate group or derivative thereof;
  b) the compound does not include a glycoside linkage;
  c) two or more C=C double bonds are contained within the —C(A)(A')-CH$_2$-L2-R2 part of the compound, and there is one or more C=C double bond that is located more than six atoms but less than 17 atoms in the chain away from the L1 group;
  d) there are no asymmetric carbon atoms present in the compound within the portion —C(A)(A')-CH$_2$-L2-R2.

In some preferred embodiments, two or more (e.g. three or more) of the following apply:
  a) R1 is a carbohydrate group or derivative thereof, wherein R1 comprises a sugar group and the sugar is selected from galactose, glucose and mannose and derivatives thereof;
  b) the compound does not include a glycoside linkage;
  c) two or more C=C double bonds are contained within the —C(A)(A')-CH$_2$-L2-R2 part of the compound, and there is one or more C=C double bond that is located more than six atoms but less than 17 atoms in the chain away from the L1 group;
  d) there are no asymmetric carbon atoms present in the compound within the portion —C(A)(A')-CH$_2$-L2-R2.
  e)

In some preferred embodiments, two or more (e.g. three or more) of the following apply:
  a) R1 is a carbohydrate group or derivative thereof, wherein R1 comprises a sugar group and the sugar is selected from galactose, glucose and mannose and derivatives thereof;
  b) the compound does not include a glycoside linkage;
  c) two or more C=C double bonds are contained within the —C(A)(A')-CH$_2$-L2-R2 part of the compound, and there is one or more C=C double bond that is located more than 8 atoms but less than 17 atoms in the chain away from the L1 group;
  d) there are no asymmetric carbon atoms present in the compound within the portion —C(A)(A')-CH$_2$-L2-R2.

In some preferred embodiments, two or more (e.g. three or more) of the following apply:
  a) R1 is a carbohydrate group or derivative thereof, wherein R1 comprises a sugar group and the sugar is selected from glucose and mannose and derivatives thereof;
  b) the compound does not include a glycoside linkage;
  c) two or more C=C double bonds are contained within the —C(A)(A')-CH$_2$-L2-R2 part of the compound, and there is one or more C=C double bond that is located more than 8 atoms but less than 17 atoms in the chain away from the L1 group;
  d) there are no asymmetric carbon atoms present in the compound within the portion —C(A)(A')-CH$_2$-L2-R2.

In one embodiment, the compound of Formula I may be of Formula Ia

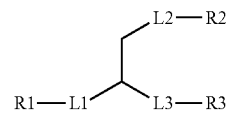

Formula Ia or a pharmaceutically acceptable salt thereof, wherein:
R1 is selected from a carbohydrate group or derivative thereof, hydrogen, a C1-C24 alkyl or a C1-C24 derivative of an alkyl group, a C2-C24 alkenyl or a C2-C24 derivative of an alkenyl group, and a C2-C24 alkynyl group or a C2-C24 derivative of an alkynyl group;
L1 is a linking group;
L2 is a linking group;
R2 is selected from hydrogen, a C1-C24 alkyl or a C1-C24 derivative of an alkyl group, a C2-C24 alkenyl or a C2-C24 derivative of an alkenyl group, and a C2-C24 alkynyl group or a C2-C24 derivative of an alkynyl group;
L3 is a linking group; and
R3 is selected from hydrogen, a C1-C24 alkyl or a C1-C24 derivative of an alkyl group, a C2-C24 alkenyl or a C2-C24 derivative of an alkenyl group, and a C2-C24 alkynyl group or a C2-C24 derivative of an alkynyl group;
and wherein one or both of R2 and R3 are a C10-C24 alkyl or a C10-C24 derivative of an alkyl group, a C10-C24 alkenyl or a C10-C24 derivative of an alkenyl group, or a C10-C24 alkynyl group or a C10-C24 derivative of an alkynyl group.

In one embodiment, the compound of Formula I may be of Formula Ia

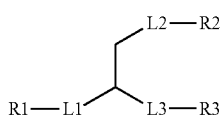

Formula Ia or a pharmaceutically acceptable salt thereof,
wherein:
R1 is selected from a carbohydrate group or derivative thereof, hydrogen, a C1-C24 alkyl or a derivative thereof, a C2-C24 alkenyl or a derivative thereof and a C2-C24 alkynyl group or a derivative thereof;
L1 is a linking group;
L2 is a linking group;
R2 is selected from hydrogen, a C1-C24 alkyl or a derivative thereof, a C2-C24 alkenyl or a derivative thereof, and a C2-C24 alkynyl group or a derivative thereof;
L3 is a linking group; and
R3 is selected from hydrogen, a C1-C24 alkyl or a derivative thereof, a C2-C24 alkenyl or a derivative thereof, and a C2-C24 alkynyl group or a derivative thereof;
and wherein one or both of R2 and R3 are a C10-C24 alkyl, alkenyl or alkynyl group or a derivative thereof.

In one embodiment, the compound of Formula Ia is not:

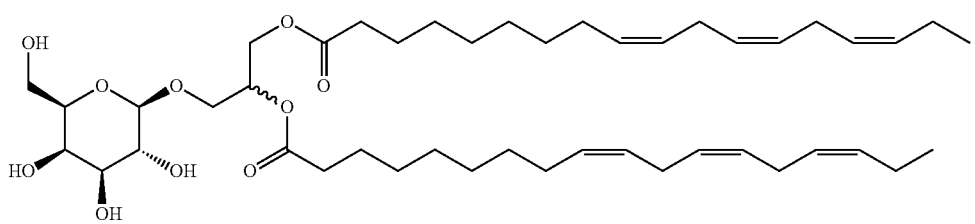 [SMILES: CC/C=C\C/C=C\C/C=C\CCCCCCCC(=O)OCC(CO[C@@H]1O[C@H](CO)[C@H](O)[C@H](O)[C@H]1O)OC(=O)CCCCCCC/C=C\C/C=C\C/C=C\CC]

In general, except where clearly not applicable, the above comments regarding preferred/optional embodiments of Formula I apply equally to Formula Ia.

Preferably, in Formula Ia:
R1 is selected from a carbohydrate group or derivative thereof, a C1-C24 alkyl or a derivative thereof, a C2-C24 alkenyl or a derivative thereof and a C2-C24 alkynyl group or a derivative thereof;
L1 is a linking group;
L2 is a linking group;
R2 is selected from hydrogen, a C1-C24 alkyl or a derivative thereof, a C2-C24 alkenyl or a derivative thereof and a C2-C24 alkynyl group or a derivative thereof;
L3 is a linking group; and
R3 is selected from hydrogen, a C1-C24 alkyl or a derivative thereof, a C2-C24 alkenyl or a derivative thereof and a C2-C24 alkynyl group or a derivative thereof;
and one or both of R2 and R3 are a C10-C24 alkyl, alkenyl or alkynyl group or a derivative thereof.

More preferably in Formula Ia:
R1 is a carbohydrate group or derivative thereof;
L1 is a linking group;
L2 is a linking group;
R2 is selected from hydrogen, a C1-C24 alkyl or a derivative thereof, a C2-C24 alkenyl or a derivative thereof and a C2-C24 alkynyl group or a derivative thereof;
L3 is a linking group; and
R3 is selected from hydrogen, a C1-C24 alkyl or a derivative thereof, a C2-C24 alkenyl or a derivative thereof and a C2-C24 alkynyl group or a derivative thereof;
and one or both of R2 and R3 are a C10-C24 alkyl, alkenyl or alkynyl group or a derivative thereof.

Yet more preferably in Formula Ia:
R1 is a carbohydrate group or derivative thereof;
L1 is a linking group;
L2 is a linking group;
R2 is a C10-C24 alkyl, alkenyl or alkynyl group or a derivative thereof; L3 is a linking group; and
R3 is a C10-C24 alkyl, alkenyl or alkynyl group or a derivative thereof.

In Formula I and Formula Ia, the R1 group is selected from a carbohydrate group or derivative thereof, hydrogen, a C1-C24 alkyl or a derivative thereof, a C2-C24 alkenyl or a derivative thereof and a C2-C24 alkynyl group or a derivative thereof. Preferably the R1 group has at least 3 carbon atoms, or at least 4 carbon atoms, e.g. from 4-24 carbon atoms or from 5-20 carbon atoms or from 6-18 carbon atoms. In one preferred embodiment the R1 group has at least 6 carbon atoms, e.g. from 6-12 carbon atoms.

In Formula I and Formula Ia, in one embodiment, the R1 group is selected from a carbohydrate group or derivative thereof, C10-C24 alkyl, alkenyl or alkynyl group or a derivative thereof.

In Formula I and Formula Ia, in one embodiment, the R1 group is a carbohydrate group or derivative thereof. The skilled person will understand that when the R1 group is a carbohydrate group this may comprise a sugar group or a derivative thereof. This group may be bound to the rest of the molecule via a glycosidic bond.

The carbohydrate group may suitably be an α-glycoside or a β-glycoside. However, it is not essential that the sugar group (or derivative thereof) is bound to the rest of the molecule via a glycosidic bond.

In one embodiment, the compound does not include a glycoside linkage. This can result in a product that is degraded more slowly as it does not have an anomeric position at which it can be readily cleaved. A product that is more difficult to cleave enzymatically will be more stable. Options for the linking group L1 are set out below and it will be seen that these include linking groups such as alkylene groups which are therefore non-glycosidic.

The carbohydrate group may be an L-stereoisomer or a D-stereoisomer.

In Formula I and Formula Ia the carbohydrate group R1 may be unprotected or protected; in other words it may have all of its hydroxyl groups in free form, or some or all of the hydroxyl groups may have been converted to be in protected form. Protecting groups for the hydroxyl groups of a carbohydrate are well known in the art and include, but are not limited to, esters, ethers and silylethers. For example, ether protecting groups may include methyl ether, trityl ether, triphenylmethyl ether, methoxymethyl ether, benzyl ether, p-methoxybenzyl ether and tetrahydropyranyl ether. Silyl ether protecting groups may include ethers based on trimethylsilyl, triethylsilyl, triisopropylsilyl, t-butyldimethylsilyl and t-butyldiphenylsilyl. Ester protecting groups may include trifluoroacetyl ester, acetyl ester, trimethylacetyl ester and benzoyl ester.

It will be appreciated that in some derivatives of a carbohydrate group adjacent hydroxyl groups can be linked via ester linkages, such as O—R—O, where R is alkylene, e.g. C1-C6 alkylene, such as methylene or iso-propylene. In some embodiments there are two pairs of adjacent hydroxyl groups linked in this manner.

Thus one type of derivative of a carbohydrate group that is encompassed by the present invention is one where one or more (e.g. two or more) of the hydroxyl groups are in protected form. It may be that all of the hydroxyl groups are in protected form. Where more than one hydroxyl group is protected, the protecting groups may be the same or may be different. It may be that all of the axially oriented hydroxyl groups are protected and/or it may be that all of the equatorially oriented hydroxyl groups are protected.

In one embodiment the carbohydrate group R1 has one or more of its hydroxyl groups protected by acetyl ester protecting groups and/or benzyl ether protecting groups.

In one embodiment the carbohydrate group R1 has all of its hydroxyl groups protected by acetyl ester protecting groups, benzyl ether protecting groups, or a combination thereof.

In one embodiment the carbohydrate group R1 has all of its hydroxyl groups protected by acetyl ester protecting groups.

Another type of derivative of a carbohydrate group that is encompassed by the present invention is where one or more (e.g. two or more) of the hydroxyl groups have been converted to amido or amino groups. It may be that only one or two of the hydroxyl groups are converted to amido or amino groups. It may be that all of the hydroxyl groups are converted to amido or amino groups.

Where more than one hydroxyl group is converted, the amido or amino groups to which they are each converted may be the same or may be different. Examples of amino and amido groups include, but are not limited to, —NH$_2$, —NHMe, —NMe$_2$, —N(COMe)H, —N(COEt)H, and —N(COMe)Me.

In general, it may be that the derivative of a carbohydrate group is one where one or more (e.g. two or more) of the hydroxyl groups have been converted to a nitrogen containing functional group, such as an azide or an amine or an amide group. Benefits of this derivativisation are that the compound can then be immobilised for conducting protein pull-down experiments.

It could also be that one or more (e.g. two or more) of the hydroxyl groups have been converted to alkyl groups, e.g. C1-C6 alkyl, such as methyl or ethyl groups.

It may, for example, be that the carbohydrate comprises a sugar (e.g. a cyclic sugar) with six carbon atoms and the hydroxyl group that is at the C6 position is modified such that there is no longer a free —OH at that position, e.g. due to the hydroxyl group having been converted to an alkyl group or to a nitrogen containing functional group, such as an azide or an amine or an amide group; this group may, for example, have up to 3 carbon atoms, such as 0, 1 or 2 carbon atoms. In one embodiment the hydroxyl group at C6 has been converted to an azide or an amine group.

In Formula I and Formula Ia the carbohydrate group of R1 may be a monosaccharide or may be a disaccharide. Optionally it may be an oligosaccharide or a polysaccharide. In one preferred embodiment, R1 may suitably be a monosaccharide, but the invention is not limited in this way.

The carbohydrate group is preferably cyclic. However it may optionally be linear. It may have any suitable number of atoms in its ring, for example 3, 4, 5, 6 or 7; preferably 4, 5 or 6. It may have any suitable number of carbons in the sugar group, for example 3, 4, 5, 6 or 7; preferably 4, 5 or 6. In one preferred embodiment R1 is a hexose. In another embodiment it is a pentose or a heptose. In another embodiment it is a tetrose.

The sugar may, for example, be selected from allose, altrose, glucose, mannose, gulose, idose, galactose and talose. However, the invention is not limited to these sugars (and derivatives thereof).

In one embodiment, the sugar is selected from galactose, glucose and mannose and derivatives thereof.

In Formula I and Formula Ia, in some preferred embodiments R1 is a galactoside or a glucoside, or a derivative thereof, in other words the sugar group is galactose or glucose. However, it could be other glycosides, such as a fructoside or a glucuronide, or derivatives thereof.

A galactose sugar group or derivative thereof may be preferred in some embodiments. A glucose sugar group or derivative thereof, or a mannose sugar group or derivative thereof, may be preferred in other embodiments. Increased activity may be seen with these groups. In one embodiment, the carbohydrate comprises a glucose sugar group or derivative thereof.

The R1 group may be an alpha-D-glucosidyl and/or a beta-D-glucosidyl group. It may alternatively be an alpha-L-glucosidyl and/or a beta-L-glucosidyl group. Preferably the glucosidyl group is linked to the rest of the molecule via an —OCH$_2$— group. However, it could be that, for example, the linker is an —O(CH$_2$)$_2$— group or an —O(CH$_2$)$_3$— group or an —O(CHOH)— group or an —O(CHNH$_2$)— group. In addition, alternate linking groups L1 could be used, as discussed further below.

The R1 group may be an alpha-D-galactosidyl and/or a beta-D-galactosidyl group. It may alternatively be an alpha-L-galactosidyl and/or a beta-L-galactosidyl. Preferably the galactosidyl group is linked to the rest of the molecule via an —OCH$_2$— group. However, it could be that, for example, the linker is an —O(CH$_2$)$_2$— group or an —O(CH$_2$)$_3$— group or an —O(CHOH)— group or an —O(CHNH$_2$)— group. In addition, alternate linking groups L1 could be used, as discussed further below.

The R1 group may be an alpha-D-mannosidyl and/or a beta-D-mannosidyl group. It may alternatively be an alpha-L-mannosidyl and/or a beta-L-mannosidyl. Preferably the mannosidyl group is linked to the rest of the molecule via an —OCH$_2$— group. However, it could be that, for example, the linker is an —O(CH$_2$)$_2$— group or an —O(CH$_2$)$_3$— group or an —O(CHOH)— group or an —O(CHNH$_2$)— group. In addition, alternate linking groups L1 could be used, as discussed further below.

In general, in Formula I and Formula Ia, L1 may be any linking group provided that this linking group is divalent. Preferably the L1 linking group has from 1-18 carbon atoms, especially from 1-12 carbon atoms, such as from 1-6 carbon atoms, e.g. 1, 2, 3 or 4 carbon atoms.

Examples of divalent linking groups include alkylene groups, cycloalkyene groups, alkenylene groups, ether groups, imino groups, carbonyl groups (including ester groups and amido groups and phosphate groups), (hetero) arylene groups, amino groups, thioether groups, and divalent residues containing any of these divalent groups bonded to each other in series. The linking group may optionally be substituted, e.g. with one or more hydroxyl, amino and/or carboxyl groups. The linking group may be a glycoside linking group.

In one embodiment, the compound does not include a glycoside linkage. This can result in a product that is degraded more slowly as it does not have an anomeric position at which it can be readily cleaved. A product that is more difficult to cleave enzymatically will be more stable. For example, the linking group may be a C1-18 alkylene group, which may optionally be substituted e.g. with one or more hydroxyl, amino and/or carboxyl groups; especially a C1-12 or C1-6 alkylene group e.g. a C1, 2, 3 or 4 alkylene group.

In one embodiment of Formula I and Formula Ia the linker group contains at least one heteroatom selected from O, P, N and S. In one such embodiment at least one such heteroatom is located in the main chain of the linker, rather than as a branch or substituent group. For example, the linker group may be an ester or an ether or a thioether or an amido or an amino or a phosphate-containing linker group.

Specific examples of linking groups that contain one or more heteroatom, with one or more of the heteroatoms being located in the main chain of the linker, include: —OCH$_2$—, —O(CH$_2$)$_2$—, —O(CH$_2$)$_3$—, —O(CHOH)—, —O(CHOH)CH$_2$—, —O(CHNH$_2$)—, —O(CHNH$_2$) CH$_2$—, —(CH$_2$)COO(CH$_2$)—, —S(CH$_2$)—, —(CH$_2$)S(CH$_2$)—, —O(PO$_2$)O(CH$_2$)—, and —O(PO$_2$)O(CH$_2$)$_2$—.

In one embodiment, in Formula I and Formula Ia, L1 is a linking group that is selected from:
  (i) a C1-C12 alkylene linking group, e.g. a C1-C8 alkylene linking group, such as methylene or ethylene or propylene or butylene or pentylene;
  (ii) an ether linking group, such as —(CH$_2$)$_p$O(CH$_2$)$_q$—, where p and q independently represent an integer of from 0 to 3, e.g. from 1 to 3;
  (iii) a C2-C6 alkenylene linking group, such as ethenylene;
  (iv) a carbonyl-containing linker group, especially an ester linking group, such as —(CH$_2$)$_p$COO(CH$_2$)$_q$—, or —(CH$_2$)$_p$OC(=O)(CH$_2$)$_q$—, where p and q independently represent an integer of from 0 to 3, e.g. from 1 to 3;
  (v) a (hetero)arylene linker, such as —(CH$_2$)$_p$(Ar)(CH$_2$)$_q$—, where p and q independently represent an integer of from 0 to 3, e.g. from 1 to 3, and Ar is a C6-C8 arylene substituent group, such as phenylene, or a 5 to 8 membered ring hetero arylene substituent group, such as furylene, thiophenylene or pyridylene;
  (vi) an amine linker of formula —RxN(Rz)Ry-, for example wherein Rx and Ry are independently C1-C4 alkylene and Rz is H or C1-C4 alkyl, such as —CH$_2$N(CH$_3$)CH$_2$—;
  (vii) a thioether linker, such as —(CH$_2$)$_p$S(CH$_2$)$_q$—, where p and q independently represent an integer of from 0 to 3, e.g. from 1 to 3;
  (viii) a glycoside linker, such as X—R4 group, wherein R4 is a C1-C12 alkyl, cycloalkyl, alkenyl or alkynyl group and X is —O—, —PR$^a$—, —NR$^a$—, —S— or —CR$^a$R$^b$—, wherein R$^a$ and R$^b$ are independently selected from the group consisting of hydrogen and C1-C4 alkyl.

In one embodiment, in Formula I and Formula Ia, L1 is a linking group that is selected from:
  (i) a C1-C6 alkylene linking group, e.g. a C1-C5 alkylene linking group, such as methylene or ethylene;
  (ii) an ether linking group, such as —(CH$_2$)pO(CH$_2$)$_q$—, where p and q independently represent an integer of from 1 to 3, and p+q equals 4 or less;
  (iii) a C2-C4 alkenylene linking group such as ethenylene;
  (iv) an ester linking group —(CH$_2$)$_p$COO(CH$_2$)$_q$—, or —(CH$_2$)$_p$OC(=O)(CH$_2$)$_q$—, where p and q independently represent an integer of from 1 to 3, and p+q equals 4 or less;
  (v) an amine linker of formula —RxN(Rz)Ry-, for example wherein Rx and Ry are C1-C4 alkylene, e.g. C1 or C2 alkylene, and Rz is H or C1-C4 alkyl, e.g. C1 or C2 alkyl;
  (vi) a thioether linker such as —(CH$_2$)$_p$S(CH$_2$)$_q$—, where p and q independently represent an integer of from 1 to 3, and p+q equals 4 or less;
  (vii) a glycoside linker, such as X—R4 group, wherein R4 is a C1-C12 alkyl, cycloalkyl, alkenyl or alkynyl group and X is —O—, —PR$^a$—, —NR$^a$—, —S— or —CR$^a$R$^b$—, wherein R$^a$ and R$^b$ are independently selected from the group consisting of hydrogen and C1-C4 alkyl.

In one embodiment, in Formula I and Formula Ia, L1 is a linking group that is selected from:
  (i) a C1-C4 alkylene linking group such as methylene or ethylene;
  (ii) an ether linking group, such as —(CH$_2$)$_p$O(CH$_2$)$_q$—, where p and q independently represent an integer of from 1 to 3, and p+q equals 4 or less;
  (iii) a C2-C4 alkenylene linking group such as ethenylene;
  (iv) an ester linking group —(CH$_2$)$_p$COO(CH$_2$)$_q$—, or —(CH$_2$)$_p$OC(=O)(CH$_2$)$_q$—, where p and q independently represent an integer of from 1 to 3, and p+q equals 4 or less;
  (v) an amine linker of formula —RxN(Rz)Ry-, for example wherein Rx and Ry are C1-C4 alkylene, e.g. C1 or C2 alkylene, and Rz is H or C1-C4 alkyl, e.g. C1 or C2 alkyl;

(vi) a thioether linker such as —(CH$_2$)$_p$S(CH$_2$)$_q$—, where p and q independently represent an integer of from 1 to 3, and p+q equals 4 or less;

(vii) a glycoside linker, such as X—R4 group, wherein R4 is a C1-C12 alkyl, cycloalkyl, alkenyl or alkynyl group and X is —O—, —PR$^a$—, —NR$^a$—, —S— or —CR$^a$R$^b$—, wherein R$^a$ and R$^b$ are independently selected from the group consisting of hydrogen and C1-C4 alkyl.

In Formula I and Formula Ia, it is preferred that L1 is a linking group that is a C1-C12 alkylene linking group or a glycoside linker, or an ester linking group having from 1-12 carbon atoms; more preferably a C1-C8 alkylene linking group or a glycoside linker having from 1-8 carbon atoms or an ester linking group having from 1-8 carbon atoms; most preferably a C1-C6 alkylene linking group or a glycoside linker having from 1-6 carbon atoms or an ester linking group having from 1-6 carbon atoms; such as a C1-C4 (e.g. C1 or C2) alkylene linking group or a glycoside linker having from 1-4 carbon atoms (e.g. C1 or C2) or an ester linking group having from 1-4 carbon atoms (e.g. C2 or C3).

In some embodiments it is preferred that L1 is a linking group that is a C1-C12 alkylene linking group or a glycoside linker, or an ester linking group, more preferably a C1-C8 alkylene linking group or a glycoside linker.

In one embodiment, in Formula I and Formula Ia, the alkylene linking groups are straight chain. In another embodiment, the linking groups are branched alkylene groups. For example, L1 may represent a linking group that is a C1-C12 straight chain alkylene linking group (such as a C1-C8 or C1-C6 straight chain alkylene linking group) or a C2-C12 branched chain alkylene linking group (such as a C2-C8, or C2-C6, or C3-C6 branched chain alkylene linking group).

Preferably, in Formula I and Formula Ia, L1 represents a linking group that is a C1-C6 alkylene linking group or a glycoside linker, more preferably a C1-C5 alkylene linking group or a glycoside linker. It may therefore be methylene, ethylene, propylene, butylene or pentylene or a glycoside linker. In one embodiment, L1 represents a linking group that is a C1-C4 alkylene linking group, such as methylene, ethylene or propylene, or a glycoside linker.

In Formula I and Formula Ia the L1 linking group may be a glycoside linker, such as X—R4 group, wherein R4 is a C1-C12 (e.g. C1-8 or C1-6 or C1-4) alkyl, a C4-C12 (e.g. C4-8 or C4-6) cycloalkyl, C2-C12 (e.g. C2-8 or C2-6 or C2-4) alkenyl, or C2-C12 (e.g. C2-8 or C2-6 or C2-4) alkynyl group and X is —O—, —O(PO$_2$)O—, —NR$^a$—, —NR$^a$C(=O)—, —PR$^a$—, —S— or —CR$^a$R$^b$-, wherein R$^a$ and R$^b$ are independently selected from the group consisting of hydrogen and C1-C4 alkyl.

Therefore the R1 group may be linked to the rest of the molecule by the group X—R4, wherein X is based on an O, N, S, P or C atom. Thus there may be an O-glycoside bond, a glycosylamine bond, a thioglycoside bond, a P-glycoside bond or a C-glycoside bond. When the group is —NR$^a$—, or —PR$^a$—, R$^a$ is selected from the group consisting of hydrogen and C1-C4 alkyl, e.g. it may be hydrogen or methyl. When the group is —CR$^a$R$^b$—, R$^a$ and R$^b$ are independently selected from the group consisting of hydrogen and C1-C4 alkyl, e.g. each may be hydrogen or methyl.

It may be that the glycoside linker is of formula —X—R4-, wherein R4 is a C1-C4 (e.g. C1, 2 or 3) alkyl, a C4-C8 (e.g. C4, 5 or 6) cycloalkyl, or a C2-C6 (e.g. C2, 3 or 4) alkenyl, and X is —O—, —O(PO$_2$)O—, —NR$^a$—, —S— or —CR$^a$R$^b$—, wherein R$^a$ and R$^b$ are independently selected from the group consisting of hydrogen and C1-C4 alkyl.

In one embodiment the glycoside linker is of formula —X—R4-, wherein R4 is a C1-C4 (e.g. C1, 2 or 3) alkyl, or a C2-C6 (e.g. C2, 3 or 4) alkenyl, and X is —O—, —O(PO$_2$)O—, —NR$^a$—, or —S—, wherein R$^a$ is selected from the group consisting of hydrogen and C1-C4 alkyl.

In one embodiment the sugar group of R1 is linked to the rest of the molecule by an O-glycoside bond. In one such embodiment the sugar group of R1 is linked to the rest of the molecule by an O—(CH$_2$)n group, wherein n is an integer of from 1 to 6. n may be 1, 2, 3, 4, 5 or 6. Preferably n is from 1 to 4, e.g. 1, 2 or 3. In one embodiment n is 1 or 2; preferably n is 1.

In Formula I, R2 is selected from hydrogen, a C1-C24 alkyl or a C1-C24 derivative of an alkyl group, a C2-C24 alkenyl or a C2-C24 derivative of an alkenyl group, and a C2-C24 alkynyl group or a C2-C24 derivative of an alkynyl group.

In Formula Ia, R2 is selected from hydrogen, a C1-C24 alkyl or a derivative thereof, a C2-C24 alkenyl or a derivative thereof and a C2-C24 alkynyl group or a derivative thereof.

Preferably the R2 group includes one or more C=C double bond, for example it may contain two or more C=C double bonds or three or more C=C double bonds. In one embodiment there are from one to eight C=C double bonds in the R2 group, such as from one to six C=C double bonds.

R2 may be selected from hydrogen, a C2-C24 alkyl or a derivative thereof, a C2-C24 alkenyl or a derivative thereof and a C2-C24 alkynyl group or a derivative thereof, or it may be selected from hydrogen, a C6-C24 alkyl or a derivative thereof, a C6-C24 alkenyl or a derivative thereof and a C6-C24 alkynyl group or a derivative thereof.

R2 is preferably a C10-C24 alkyl, alkenyl or alkynyl group, or a derivative thereof. Preferably, R2 is a C10-C20 alkyl, alkenyl or alkynyl group, or derivative thereof, such as a C10-C18 or a C12-C18 alkyl, alkenyl or alkynyl group, or derivative thereof. It may, for example, be a C12-C24 group, a C12-C20 group or a C13-C20 group or a C14-C20 group.

In one embodiment R2 may be a C10-C24 derivative of an alkyl, alkenyl or alkynyl group. Preferably, R2 is a C10-C20 derivative of an alkyl, alkenyl or alkynyl group, such as a C10-C18 or a C12-C18 derivative of an alkyl, alkenyl or alkynyl group. It may, for example, be a C12-C24 group, a C12-C20 group or a C13-C20 group. In such embodiments the alkyl, alkenyl or alkynyl group need not be the sole provider of the carbon atoms to meet the stated range; carbon atoms may also be contributed by the modification of these groups to form the derivative. This applies in the embodiment described below where the derivative of an alkyl, alkenyl or alkynyl group that is encompassed by the present invention is one where one or more (e.g. two or more) of the hydrogen atoms in the hydrocarbon chain are replaced with substituent groups and where these substituent groups include one or more carbon atoms.

In all embodiments where a derivative of an alkyl, alkenyl or alkynyl group is contemplated, one derivative of an alkyl, alkenyl or alkynyl group that is encompassed by the present invention is one where one or more (e.g. two or more) of the carbon atoms in the hydrocarbon chain are replaced with heteroatoms. The heteroatoms may, for example, be selected from O, N, S, SO$_2$, P, B, Si, and combinations thereof. For example, the heteroatoms may be selected from O, N, S, and combinations thereof. In one embodiment from 1 to 5 carbon atoms in the group are replaced with heteroatoms, e.g. 1, 2 or 3 carbon atoms in the group might be replaced with heteroatoms. When more than one carbon atom in the group is replaced, the heteroatoms used may be the same or may be different.

Therefore, for example, the R2 group may include an ether, amine, thioether, sulfone, and/or sulphonamide group in the chain.

Clearly, the number of carbon atoms in the alkyl, alkenyl or alkynyl group of R2 will be reduced in the embodiment where it is a derivative in which one or more of the carbon atoms in the hydrocarbon chain are replaced with heteroatoms. However, the skilled person would readily be able to see how many carbon atoms would have been in the hydrocarbon chain had one or more of these not been replaced with heteroatoms.

In addition, in all embodiments where a derivative of an alkyl, alkenyl or alkynyl group is contemplated, another derivative of an alkyl, alkenyl or alkynyl group that is encompassed by the present invention is one where one or more (e.g. two or more) of the hydrogen atoms in the hydrocarbon chain are replaced with substituent groups. In one embodiment from 1 to 10 hydrogen atoms in the group are substituted, such as from 1 to 6, e.g. 1, 2, 3 or 4 of the hydrogen atoms in the hydrocarbon chain might be replaced with substituent groups. When more than one hydrogen atom in the group is replaced, the substituent groups used may be the same or may be different.

For example, the alkyl, alkenyl or alkynyl group may optionally be substituted with one or more substituent groups independently selected from hydroxyl and amino and carboxyl groups, and aryl or heteroaryl groups (especially unsaturated cyclic and heterocyclic groups with 5 to 10 atoms (e.g. 6 to 10 atoms) in their ring, such as imidazolyl, thiazolyl, thienyl, phenyl, tolyl, xylyl, pyridinyl, pyrimidinyl, pyrazinyl, indolyl or naphthyl groups).

It may be that the alkyl, alkenyl or alkynyl group is optionally substituted with one or more substituent groups independently selected from hydroxyl and amino and carboxyl groups.

It may be that the alkyl, alkenyl or alkynyl group is optionally substituted with one or more substituent groups independently selected from aryl or heteroaryl groups, especially unsaturated cyclic and heterocyclic groups with 5 to 10 atoms (e.g. 6 to 10 atoms) in their ring, such as imidazolyl, thiazolyl, thienyl, phenyl, tolyl, xylyl, pyridinyl, pyrimidinyl, pyrazinyl, indolyl or naphthyl groups. The ring itself may be substituted, e.g. with one or more C1-6 alkyl groups, such as one or two (or more) methyl or ethyl groups, as is the case in tolyl and xylyl. Preferably the total number of carbon atoms in each of the substituent groups is from 5 to 12.

In one embodiment the R2 group is a substituted alkenyl; for example it may be an (alkyl)-CHOH-(alkenyl), (alkyl)-CHNH$_2$-(alkenyl), (alkenyl)-CHOH-(alkenyl), or (alkenyl)-CHNH$_2$-(alkenyl) group.

It may be that the total number of carbon atoms in said substituted alkenyl is from 10-24, such as from 10-20 or 10-18 or 12-18.

In one embodiment the R2 group is a substituted alkyl; for example it may be an alkyl group that is substituted with one or more substituent groups that are independently selected from unsaturated cyclic and heterocyclic groups with 5 to 10 atoms (e.g. 6 to 10 atoms) in their ring. Preferably it is an alkyl group that is substituted with two or more substituent groups that are independently selected from unsaturated cyclic and heterocyclic groups with 5 to 10 atoms (e.g. 6 to 10 atoms) in their ring. In one embodiment the substituent groups are unsaturated cyclic groups with 5 to 10 atoms (e.g. 6 to 10 atoms) in their ring and with a total number of carbon atoms of from 5 to 12, such as phenyl or naphthyl or tolyl or xylyl groups.

In one embodiment there are two substituent groups on the same carbon atom in the alkyl group, and preferably these two substituent groups are the same.

In one embodiment R2 is a C10-C24 derivative of an alkyl group, where the alkyl group is a C1-12 group and this is substituted with one or more C5-12 substituent groups independently selected from aryl or heteroaryl groups, especially unsaturated cyclic and heterocyclic groups with 5 to 10 atoms (e.g. 6 to 10 atoms) in their ring. Thus the total number of carbon atoms in the R2 group is C10-C24, and this is made up of carbon atoms from the alkyl group and carbon atoms from the aryl or heteroaryl substituent groups.

In one embodiment, R2 is a C10-C20 derivative of an alkyl group, such as a C10-C18 or a C12-C18 derivative of an alkyl group. It may, for example, be a C12-C24 group, a C12-C20 group or a C13-C20 group.

It may be that the alkyl group is a C1-8 group and this is substituted with one or more C5-12 substituent groups independently selected from aryl or heteroaryl groups, especially unsaturated cyclic and heterocyclic groups with 5 to 10 atoms (e.g. 6 to 10 atoms) in their ring. Preferably, the alkyl group is a C1-6 group (e.g. C1, C2, C3 or C4) and this is substituted with one or more C5-12 substituent groups independently selected from aryl or heteroaryl groups, especially unsaturated cyclic and heterocyclic groups with 5 to 10 atoms (e.g. 6 to 10 atoms) in their ring.

In one embodiment the substituent groups in the derivative of an alkyl group are selected from unsaturated cyclic groups with 5 to 10 atoms (e.g. 6 to 10 atoms) in their ring, such as phenyl or naphthyl or tolyl or xylyl groups, especially unsaturated cyclic groups with 6 atoms in their ring, such as phenyl or tolyl or xylyl groups.

In Formula I and Formula Ia, in one embodiment the R2 group is unsubstituted.

In Formula I and Formula Ia, it may be that in R2 one or more (e.g. two or more) of the carbon atoms in the hydrocarbon chain are replaced with heteroatoms and one or more (e.g. two or more) of the hydrogen atoms in the hydrocarbon chain are replaced with substituent groups. Thus, for example, the R2 group may include an amide or anhydride group in the chain.

The alkyl, alkenyl or alkynyl group may be straight chain or branched; in one embodiment it is straight chain.

In Formula I and Formula Ia, in one embodiment the R2 group is a C10-C24 alkenyl group or a C12-C24 alkenyl group, such as a C12-C20 alkenyl group or a C14-C20 alkenyl group.

In Formula I and Formula Ia, when the R2 group is an alkenyl group (or derivative thereof) it may be that the C═C double bond(s) are Z-configured (cis) or E-configured (trans). Where there is more than one double bond these may be all are Z-configured, or they may be all E-configured, or there may be combinations of Z-configured and E-configured double bonds. In one embodiment all the C═C double bonds are Z-configured.

Preferably, R2 is a C10-C24 alkenyl and may, e.g., be a straight-chain alkenyl having from 10 to 20 carbon atoms. Preferably, R2 is a C12-C18 alkenyl.

In Formula I and Formula Ia, preferably the R2 alkenyl group has from one to five C═C double bonds, such as from one to four C═C double bonds, e.g. from one to three C═C double bonds, such as two or three C═C double bonds.

In Formula I and Formula Ia preferably the R2 group is an alkenyl group and the (or each) double bond is located at carbon position 5 in the chain or higher, such as position 6 or higher, or position 7 or higher, preferably the (or each) C=C double bond is located at position 8 or higher.

More preferably, R2 is a C14-C18 alkenyl (e.g. a C16 or C17 alkenyl) having one to three C=C double bonds, such as two or three C=C double bonds, for example R2 may be a C17 alkenyl having three C=C double bonds.

In one embodiment of Formula I and Formula Ia the alkenyl is a 8,11,14-heptadecatrienyl. In one embodiment all the double bonds are Z-configured.

In Formula I and Formula Ia, in general, L2 may be any linking group provided that this linking group is divalent. Preferably the L2 linking group has from 1-18 carbon atoms, especially from 1-12 carbon atoms, such as from 1-6 carbon atoms, e.g. 1, 2, 3 or 4 carbon atoms.

Examples of divalent linking groups include alkylene groups, cycloalkyene groups, alkenylene groups, ether groups, imino groups, carbonyl groups (including ester groups and amido groups and phosphate groups), (hetero) arylene groups, amino groups, thioether groups, and divalent residues containing any of these divalent groups bonded to each other in series. The linking group may optionally be substituted, e.g. with one or more hydroxyl, amino and/or carboxyl groups.

In Formula I and Formula Ia, in one embodiment the linker group contains at least one heteroatom selected from O, P, N and S. In one such embodiment at least one such heteroatom is located in the main chain of the linker, rather than as a branch or substituent group. For example, the linker group may be an ester or an ether or a thioether or an amido or an amino or a phosphate-containing linker group.

Specific examples of linking groups that contain one or more heteroatom, with one or more of the heteroatoms being located in the main chain of the linker, include: —OC(=O)—, —OC(=O)CH$_2$—, —NHC(=O)—, —NHC(=O)CH$_2$—, —N(CH$_2$)C(=O)—, —N(CH$_2$)C(=O)CH$_2$—, —OCH$_2$—, —O(CH$_2$)$_2$—, —O(CH$_2$)$_3$—, —O(CHOH)—, —O(CHOH)CH$_2$—, —O(CHNH$_2$)—, —O(CHNH$_2$)CH$_2$—, —(CH$_2$)COO(CH$_2$)—, —S(CH$_2$)—, —(CH$_2$)S(CH$_2$)—, —O(PO$_2$)O(CH$_2$)—, and —O(PO$_2$)O(CH$_2$)$_2$—.

In Formula I and Formula Ia, in one embodiment, L2 is a linking group that is selected from:
(i) a C1-C12 alkylene linking group, e.g. a C1-C8 alkylene linking group, such as methylene or ethylene or propylene or butylene or pentylene;
(ii) an ether linking group, such as —(CH$_2$)$_p$O(CH$_2$)$_q$—, where p and q independently represent an integer of from 0 to 3, e.g. from 1 to 3;
(iii) a C2-C6 alkenylene linking group, such as ethenylene;
(iv) a carbonyl-containing linker group; especially an ester linking group, such as —(CH$_2$)$_p$C(=O)O(CH$_2$)$_q$-, or —(CH$_2$)$_p$OC(=O)(CH$_2$)$_q$—, where p and q independently represent an integer of from 0 to 3, e.g. from 1 to 3, or an amido linking group, such as —(CH$_2$)$_p$NRzC(=O)(CH$_2$)$_q$—, or —(CH$_2$)$_p$C(=O)NRz(CH$_2$)$_q$—, where p and q independently represent an integer of from 0 to 3, e.g. from 1 to 3 and Rz is H or C1-C4 alkyl;
(v) a (hetero)arylene linker, such as —(CH$_2$)$_p$(Ar)(CH$_2$)$_q$—, where p and q independently represent an integer of from 0 to 3, e.g. from 1 to 3, and Ar is a C6-C8 arylene substituent group, such as phenylene, or a 5 to 8 membered ring hetero arylene substituent group, such as furylene, thiophenylene or pyridylene;
(vi) an amine linker of formula —RxN(Rz)Ry-, for example wherein Rx and Ry are independently C1-C4 alkylene and Rz is H or C1-C4 alkyl, such as —CH$_2$N(CH$_3$)CH$_2$—;
(vii) a thioether linker, such as —(CH$_2$)$_p$S(CH$_2$)$_q$—, where p and q independently represent an integer of from 0 to 3, e.g. from 1 to 3;
(viii) a glycoside linker, such as X—R4 group, wherein R4 is a C1-C12 alkyl, cycloalkyl, alkenyl or alkynyl group and X is —O—, —PR$^a$—, —NR$^a$—, —S— or —CR$^a$R$^b$—, wherein R$^a$ and R$^b$ are independently selected from the group consisting of hydrogen and C1-C4 alkyl.

In Formula I and Formula Ia, in one embodiment, L2 is a linking group that is selected from:
(i) a C1-C6 alkylene linking group, e.g. a C1-C5 alkylene linking group, such as methylene or ethylene;
(ii) an ether linking group, such as —(CH$_2$)$_p$O(CH$_2$)$_q$—, where p and q independently represent an integer of from 1 to 3, and p+q equals 4 or less;
(iii) a C2-C4 alkenylene linking group such as ethenylene;
(iv) an ester linking group such as —(CH$_2$)$_p$C(=O)O(CH$_2$)$_q$—, or —(CH$_2$)$_p$OC(=O)(CH$_2$)$_q$—, where p and q each independently represent an integer of from 0 to 3, and p+q equals 4 or less, or an amido linking group, such as —(CH$_2$)$_p$NRzC(=O)(CH$_2$)$_q$—, or —(CH$_2$)$_p$C(=O)NRz(CH$_2$)$_q$—, where p and q independently represent an integer of from 0 to 3, and p+q equals 4 or less, and Rz is H or C1-C4 alkyl;
(v) an amine linker of formula —RxN(Rz)Ry-, for example wherein Rx and Ry are C1-C4 alkylene, e.g. C1 or C2 alkylene, and Rz is H or C1-C4 alkyl, e.g. C1 or C2 alkyl;
(vi) a thioether linker such as —(CH$_2$)$_p$S(CH$_2$)$_q$—, where p and q independently represent an integer of from 1 to 3, and p+q equals 4 or less.

In Formula I and Formula Ia, in one embodiment, L2 is a linking group that is selected from:
(i) a C1-C4 alkylene linking group such as methylene or ethylene;
(ii) an ether linking group, such as —(CH$_2$)$_p$O(CH$_2$)$_q$—, where p and q independently represent an integer of from 1 to 3, and p+q equals 4 or less;
(iii) a C2-C4 alkenylene linking group such as ethenylene;
(iv) an ester linking group such as —(CH$_2$)$_p$C(=O)O(CH$_2$)$_q$—, or —(CH$_2$)$_p$OC(=O)(CH$_2$)$_q$—, where p and q each independently represent an integer of from 0 to 3, and p+q equals 4 or less, or an amido linking group, such as —(CH$_2$)$_p$NRzC(=O)(CH$_2$)$_q$—, or —(CH$_2$)$_p$C(=O)NRz(CH$_2$)$_q$—, where p and q independently represent an integer of from 0 to 3, and p+q equals 4 or less, and Rz is H or C1-C3 alkyl;
(v) an amine linker of formula —RxN(Rz)Ry-, for example wherein Rx and Ry are C1-C4 alkylene, e.g. C1 or C2 alkylene, and Rz is H or C1-C4 alkyl, e.g. C1 or C2 alkyl;
(vi) a thioether linker such as —(CH$_2$)$_p$S(CH$_2$)$_q$—, where p and q independently represent an integer of from 1 to 3, and p+q equals 4 or less.

In Formula I and Formula Ia it is preferred that L2 is a linking group that is a C1-C12 alkylene linking group or a C1-C12 ester linking group, or a C1-12 amido linking group, more preferably a C1-C8 alkylene linking group or a C1-C8 ester linking group or a C1-8 amido linking group. In one embodiment, the alkylene linking groups are straight chain.

In another embodiment, the linking groups are branched alkylene groups. For example, L2 may represent a linking group that is a C1-C12 straight chain alkylene linking group (such as a C1-C8 or C1-C6 straight chain alkylene linking group) or a C2-C12 branched chain alkylene linking group (such as a C2-C8, or C2-C6, or C3-C6 branched chain alkylene linking group) or a C1-C12 (such as a C1-C8 or C1-C6) ester group or a C1-C12 (such as a C1-C8 or C1-C6) amido group.

In Formula I and Formula Ia, preferably, L2 represents a linking group that is a C1-C6 alkylene linking group or C1-C6 ester group or C1-C6 amido group, more preferably a C1-C5 alkylene linking group or C1-C5 ester group or C1-C5 amido group, such as a C1-C4 alkylene linking group or C1-C4 ester group or C1-C4 amido group. It may therefore be methylene, ethylene, propylene, butylene or pentylene, or an ester linking group —$(CH_2)_pC(=O)O(CH_2)_q$— or —$(CH_2)_pOC(=O)(CH_2)_q$—, where p and q each independently represent an integer of from 0 to 3, especially 0, 1 or 2, and p+q equals 4 or less, especially 3 or less, or an amido group —$(CH_2)_pNRzC(=O)(CH_2)_q$-, or —$(CH_2)_pC(=O)NRz(CH_2)_q$—, where p and q independently represent an integer of from 0 to 3, especially 0, 1 or 2, and p+q equals 4 or less, especially 3 or less, and Rz is H or C1-C3 alkyl, especially H or C1 alkyl.

In one embodiment, in Formula I and Formula Ia, L2 represents a linking group that is a C1-C4 alkylene linking group, such as methylene, ethylene or propylene, or an ester linking group —$(CH_2)_pC(=O)O(CH_2)_q$— or —$(CH_2)_pOC(=O)(CH_2)_q$—, where p and q each independently represent an integer of from 0 to 3, especially 0, 1 or 2, and p+q equals 3 or less, especially 2 or less, or an amido group —$(CH_2)_pNRzC(=O)(CH_2)_q$—, or —$(CH_2)_pC(=O)NRz(CH_2)_q$—, where p and q independently represent an integer of from 0 to 3, especially 0, 1 or 2, and p+q equals 3 or less, especially 2 or less, and Rz is H or C1-C2 alkyl, especially H.

It may be that the L2 linking group is an O-ester linking group, C-ester linking group, ether linking group, carbonyl linking group, amine linking group, N-amido linking group, C-amido linking group, thioether linking group or alkylene linking group.

In Formula I and Formula Ia, in one embodiment L2 is —$CH_2$—, —$CH_2CH_2$—, —$CH_2CH_2CH_2$—, —O—C(=O)—, —NH—, —C(=O)—, —C(=O)—$CH_2$—, —O—$CH_2$—C(=O)—, —C(=O)—O—, —NHC(=O)—, —C(=O)NH—, —O—, —$CH_2$—NH—, —$CH_2$—NH—$CH_2$—, —S—, —S—$CH_2$—, —$CH_2$—S—$CH_2$—, or —$CH_2$—O—.

In Formula I and Formula Ia, in one embodiment L2 is —O—C(=O)—, —NH—, —C(=O)—, —C(=O)—$CH_2$-, —O—$CH_2$—C(=O)—, —C(=O)—O—, —NHC(=O)—, —C(=O)NH—, —O—, —$CH_2$—NH—, —$CH_2$—NH—$CH_2$—, —S—, —S—$CH_2$—, —$CH_2$—S—$CH_2$—, or —$CH_2$—O—.

In Formula I, R3 is selected from hydrogen, a C1-C24 alkyl or a C1-C24 derivative of an alkyl group, a C2-C24 alkenyl or a C2-C24 derivative of an alkenyl group, and a C2-C24 alkynyl group or a C2-C24 derivative of an alkynyl group.

In Formula Ia, R3 is selected from hydrogen, a C1-C24 alkyl or a derivative thereof, a C2-C24 alkenyl or a derivative thereof and a C2-C24 alkynyl group or a derivative thereof.

Preferably the R3 group includes one or more C=C double bond, for example it may contain two or more C=C double bonds or three or more C=C double bonds. In one embodiment there are from one to eight C=C double bonds in the R3 group, such as from one to six C=C double bonds.

R3 may be selected from hydrogen, a C2-C24 alkyl or a derivative thereof, a C2-C24 alkenyl or a derivative thereof and a C2-C24 alkynyl group or a derivative thereof, or it may be selected from hydrogen, a C6-C24 alkyl or a derivative thereof, a C6-C24 alkenyl or a derivative thereof and a C6-C24 alkynyl group or a derivative thereof.

R3 is preferably a C10-C24 alkyl, alkenyl or alkynyl group, or a derivative thereof. Preferably, R3 is a C10-C20 alkyl, alkenyl or alkynyl group, or derivative thereof, such as a C10-C18 or a C12-C18 alkyl, alkenyl or alkynyl group, or derivative thereof. It may, for example, be a C12-C24 group, a C12-C20 group or a C13-C20 group or a C14-C20 group.

In one embodiment R3 may be a C10-C24 derivative of an alkyl, alkenyl or alkynyl group. Preferably, R3 is a C10-C20 derivative of an alkyl, alkenyl or alkynyl group, such as a C10-C18 or a C12-C18 derivative of an alkyl, alkenyl or alkynyl group. It may, for example, be a C12-C24 group, a C12-C20 group or a C13-C20 group. In such embodiments the alkyl, alkenyl or alkynyl group need not be the sole provider of the carbon atoms to meet the stated range; carbon atoms may also be contributed by the modification of these groups to form the derivative. This applies in the embodiment described below where the derivative of an alkyl, alkenyl or alkynyl group that is encompassed by the present invention is one where one or more (e.g. two or more) of the hydrogen atoms in the hydrocarbon chain are replaced with substituent groups and where these substituent groups include one or more carbon atoms.

In all embodiments where a derivative of an alkyl, alkenyl or alkynyl group is contemplated, one derivative of an alkyl, alkenyl or alkynyl group that is encompassed by the present invention is one where one or more (e.g. two or more) of the carbon atoms in the hydrocarbon chain are replaced with heteroatoms. The heteroatoms may, for example, be selected from O, N, S, $SO_2$, P, B, Si, and combinations thereof. For example, the heteroatoms may be selected from O, N, S, and combinations thereof. In one embodiment from 1 to 5 carbon atoms in the group are replaced with heteroatoms, e.g. 1, 2 or 3 carbon atoms in the group might be replaced with heteroatoms. When more than one carbon atom in the group is replaced, the heteroatoms used may be the same or may be different.

Therefore, for example, the R3 group may include an ether, amine, thioether, sulfone, and/or sulphonamide group in the chain.

Clearly, the number of carbon atoms in the alkyl, alkenyl or alkynyl group of R3 will be reduced in the embodiment where it is a derivative in which one or more of the carbon atoms in the hydrocarbon chain are replaced with heteroatoms. However, the skilled person would readily be able to see how many carbon atoms would have been in the hydrocarbon chain had one or more of these not been replaced with heteroatoms.

In addition, in all embodiments where a derivative of an alkyl, alkenyl or alkynyl group is contemplated, another derivative of an alkyl, alkenyl or alkynyl group that is encompassed by the present invention is one where one or more (e.g. two or more) of the hydrogen atoms in the hydrocarbon chain are replaced with substituent groups. In one embodiment from 1 to 10 hydrogen atoms in the group are substituted, such as from 1 to 6, e.g. 1, 2, 3 or 4 of the hydrogen atoms in the hydrocarbon chain might be replaced with substituent groups. When more than one hydrogen atom in the group is replaced, the substituent groups used may be the same or may be different.

For example, the alkyl, alkenyl or alkynyl group may optionally be substituted with one or more substituent groups independently selected from hydroxyl and amino and carboxyl groups, and aryl or heteroaryl groups (especially unsaturated cyclic and heterocyclic groups with 5 to 10 atoms (e.g. 6 to 10 atoms) in their ring, such as imidazolyl, thiazolyl, thienyl, phenyl, tolyl, xylyl, pyridinyl, pyrimidinyl, pyrazinyl, indolyl or naphthyl groups).

It may be that the alkyl, alkenyl or alkynyl group is optionally substituted with one or more substituent groups independently selected from hydroxyl and amino and carboxyl groups.

It may be that the alkyl, alkenyl or alkynyl group is optionally substituted with one or more substituent groups independently selected from aryl or heteroaryl groups, especially unsaturated cyclic and heterocyclic groups with 5 to 10 atoms (e.g. 6 to 10 atoms) in their ring, such as imidazolyl, thiazolyl, thienyl, phenyl, tolyl, xylyl, pyridinyl, pyrimidinyl, pyrazinyl, indolyl or naphthyl groups. The ring itself may be substituted, e.g. with one or more C1-6 alkyl groups, such as one or two (or more) methyl or ethyl groups, as is the case in tolyl and xylyl. Preferably the total number of carbon atoms in each of the substituent groups is from 5 to 12.

In one embodiment the R3 group is a substituted alkenyl; for example it may be an (alkyl)-CHOH-(alkenyl), (alkyl)-CHNH$_2$-(alkenyl), (alkenyl)-CHOH-(alkenyl), or (alkenyl)-CHNH$_2$-(alkenyl) group.

It may be that the total number of carbon atoms in said substituted alkenyl is from 10-24, such as from 10-20 or 10-18 or 12-18.

In one embodiment the R3 group is a substituted alkyl; for example it may be an alkyl group that is substituted with one or more substituent groups that are independently selected from unsaturated cyclic and heterocyclic groups with 5 to 10 atoms (e.g. 6 to 10 atoms) in their ring. Preferably it is an alkyl group that is substituted with two or more substituent groups that are independently selected from unsaturated cyclic and heterocyclic groups with 5 to 10 atoms (e.g. 6 to 10 atoms) in their ring. In one embodiment the substituent groups are unsaturated cyclic groups with 5 to 10 atoms (e.g. 6 to 10 atoms) in their ring and with a total number of carbon atoms of from 5 to 12, such as phenyl or naphthyl or tolyl or xylyl groups.

In one embodiment there are two substituent groups on the same carbon atom in the alkyl group, and preferably these two substituent groups are the same.

In one embodiment R3 is a C10-C24 derivative of an alkyl group, where the alkyl group is a C1-12 group and this is substituted with one or more C5-12 substituent groups independently selected from aryl or heteroaryl groups, especially unsaturated cyclic and heterocyclic groups with 5 to 10 atoms (e.g. 6 to 10 atoms) in their ring. Thus the total number of carbon atoms in the R3 group is C10-C24, and this is made up of carbon atoms from the alkyl group and carbon atoms from the aryl or heteroaryl substituent groups.

In one embodiment, R3 is a C10-C20 derivative of an alkyl group, such as a C10-C18 or a C12-C18 derivative of an alkyl group. It may, for example, be a C12-C24 group, a C12-C20 group or a C13-C20 group.

It may be that the alkyl group is a C1-8 group and this is substituted with one or more C5-12 substituent groups independently selected from aryl or heteroaryl groups, especially unsaturated cyclic and heterocyclic groups with 5 to 10 atoms (e.g. 6 to 10 atoms) in their ring. Preferably, the alkyl group is a C1-6 group (e.g. C1, C2, C3 or C4) and this is substituted with one or more C5-12 substituent groups independently selected from aryl or heteroaryl groups, especially unsaturated cyclic and heterocyclic groups with 5 to 10 atoms (e.g. 6 to 10 atoms) in their ring.

In one embodiment the substituent groups in the derivative of an alkyl group are selected from unsaturated cyclic groups with 5 to 10 atoms (e.g. 6 to 10 atoms) in their ring, such as phenyl or naphthyl or tolyl or xylyl groups, especially unsaturated cyclic groups with 6 atoms in their ring, such as phenyl or tolyl or xylyl groups.

In Formula I and Formula Ia, in one embodiment the R3 group is unsubstituted.

In Formula I and Formula Ia, it may be that in R3 one or more (e.g. two or more) of the carbon atoms in the hydrocarbon chain are replaced with heteroatoms and one or more (e.g. two or more) of the hydrogen atoms in the hydrocarbon chain are replaced with substituent groups. Thus, for example, the R3 group may include an amide or anhydride group in the chain.

The alkyl, alkenyl or alkynyl group may be straight chain or branched; in one embodiment it is straight chain.

In Formula I and Formula Ia, in one embodiment the R3 group is a C10-C24 alkenyl group or a C12-C24 alkenyl group, such as a C12-C20 alkenyl group or a C14-C20 alkenyl group.

In Formula I and Formula Ia, when the R3 group is an alkenyl group (or derivative thereof) it may be that the C═C double bond(s) are Z-configured (cis) or E-configured (trans). Where there is more than one double bond these may be all are Z-configured, or they may be all E-configured, or there may be combinations of Z-configured and E-configured double bonds. In one embodiment all the C═C double bonds are Z-configured.

Preferably, R3 is a C10-C24 alkenyl and may, e.g., be a straight-chain alkenyl having from 10 to 20 carbon atoms. Preferably, R3 is a C12-C18 alkenyl.

In Formula I and Formula Ia, preferably the R3 alkenyl group has from one to five C═C double bonds, such as from one to four C═C double bonds, e.g. from one to three C═C double bonds, such as two or three C═C double bonds.

In Formula I and Formula Ia preferably the R3 group is an alkenyl group and the (or each) double bond is located at carbon position 5 in the chain or higher, such as position 6 or higher, or position 7 or higher, preferably the (or each) C═C double bond is located at position 8 or higher.

More preferably, R3 is a C14-C18 alkenyl (e.g. a C16 or C17 alkenyl) having one to three C═C double bonds, such as two or three C═C double bonds, for example R3 may be a C17 alkenyl having three C═C double bonds.

In one embodiment of Formula I and Formula Ia the alkenyl R3 is a 8,11,14-heptadecatrienyl. In one embodiment all the double bonds are Z-configured.

In Formula I and Formula Ia, in general, L3 may be any linking group provided that this linking group is divalent. Preferably the L3 linking group has from 1-18 carbon atoms, especially from 1-12 carbon atoms, such as from 1-6 carbon atoms, e.g. 1, 2, 3 or 4 carbon atoms.

Examples of divalent linking groups include alkylene groups, cycloalkyene groups, alkenylene groups, ether groups, imino groups, carbonyl groups (including ester groups and amido groups and phosphate groups), (hetero)arylene groups, amino groups, thioether groups, and divalent residues containing any of these divalent groups bonded to each other in series. The linking group may optionally be substituted, e.g. with one or more hydroxyl, amino and/or carboxyl groups.

In Formula I and Formula Ia, in one embodiment the linker group contains at least one heteroatom selected from O, P, N and S. In one such embodiment at least one such heteroatom is located in the main chain of the linker, rather than as a branch or substituent group. For example, the linker group may be an ester or an ether or a thioether or an amido or an amino or a phosphate-containing linker group.

Specific examples of linking groups that contain one or more heteroatom, with one or more of the heteroatoms being located in the main chain of the linker, include: —OC(=O)—, —OC(=O)CH$_2$—, —NHC(=O)—, —NHC(=O)CH$_2$—, —N(CH$_2$)C(=O)—, —N(CH$_2$)C(=O)CH$_2$—, —OCH$_2$—, —O(CH$_2$)$_2$—, —O(CH$_2$)$_3$—, —O(CHOH)—, —O(CHOH)CH$_2$—, —O(CHNH$_2$)—, —O(CHNH$_2$)CH$_2$—, —(CH$_2$)COO(CH$_2$)—, —S(CH$_2$)—, —(CH$_2$)S(CH$_2$)—, —O(PO$_2$)O(CH$_2$)—, and —O(PO$_2$)O(CH$_2$)$_2$—.

In Formula I and Formula Ia, in one embodiment, L3 is a linking group that is selected from:
(i) a C1-C12 alkylene linking group, e.g. a C1-C8 alkylene linking group, such as methylene or ethylene or propylene or butylene or pentylene;
(ii) an ether linking group, such as —(CH$_2$)$_p$O(CH$_2$)$_q$—, where p and q independently represent an integer of from 0 to 3, e.g. from 1 to 3;
(iii) a C2-C6 alkenylene linking group, such as ethenylene;
(iv) a carbonyl-containing linker group; especially an ester linking group, such as —(CH$_2$)$_p$C(=O)O(CH$_2$)$_q$-, or —(CH$_2$)$_p$OC(=O)(CH$_2$)$_q$—, where p and q independently represent an integer of from 0 to 3, e.g. from 1 to 3, or an amido linking group, such as —(CH$_2$)$_p$NRzC(=O)(CH$_2$)$_q$—, or —(CH$_2$)$_p$C(=O)NRz(CH$_2$)$_q$—, where p and q independently represent an integer of from 0 to 3, e.g. from 1 to 3 and Rz is H or C1-C4 alkyl;
(v) a (hetero)arylene linker, such as —(CH$_2$)$_p$(Ar)(CH$_2$)$_q$—, where p and q independently represent an integer of from 0 to 3, e.g. from 1 to 3, and Ar is a C6-C8 arylene substituent group, such as phenylene, or a 5 to 8 membered ring hetero arylene substituent group, such as furylene, thiophenylene or pyridylene;
(vi) an amine linker of formula —RxN(Rz)Ry-, for example wherein Rx and Ry are independently C1-C4 alkylene and Rz is H or C1-C4 alkyl, such as —CH$_2$N(CH$_3$)CH$_2$—;
(vii) a thioether linker, such as —(CH$_2$)$_p$S(CH$_2$)$_q$—, where p and q independently represent an integer of from 0 to 3, e.g. from 1 to 3;
(viii) a glycoside linker, such as X—R4 group, wherein R4 is a C1-C12 alkyl, cycloalkyl, alkenyl or alkynyl group and X is —O—, —PR$^a$—, —NR$^a$—, —S— or —CR$^a$R$^b$—, wherein R$^a$ and R$^b$ are independently selected from the group consisting of hydrogen and C1-C4 alkyl.

In Formula I and Formula Ia, in one embodiment, L3 is a linking group that is selected from:
(i) a C1-C6 alkylene linking group, e.g. a C1-C5 alkylene linking group, such as methylene or ethylene;
(ii) an ether linking group, such as —(CH$_2$)$_p$O(CH$_2$)$_q$—, where p and q independently represent an integer of from 1 to 3, and p+q equals 4 or less;
(iii) a C2-C4 alkenylene linking group such as ethenylene;
(iv) an ester linking group such as —(CH$_2$)$_p$C(=O)O(CH$_2$)$_q$—, or —(CH$_2$)$_p$OC(=O)(CH$_2$)$_q$—, where p and q each independently represent an integer of from 0 to 3, and p+q equals 4 or less, or an amido linking group, such as —(CH$_2$)$_p$NRzC(=O)(CH$_2$)$_q$—, or —(CH$_2$)$_p$C(=O)NRz(CH$_2$)$_q$—, where p and q independently represent an integer of from 0 to 3, and p+q equals 4 or less, and Rz is H or C1-C4 alkyl;
(v) an amine linker of formula —RxN(Rz)Ry-, for example wherein Rx and Ry are C1-C4 alkylene, e.g. C1 or C2 alkylene, and Rz is H or C1-C4 alkyl, e.g. C1 or C2 alkyl;
(vi) a thioether linker such as —(CH$_2$)$_p$S(CH$_2$)$_q$—, where p and q independently represent an integer of from 1 to 3, and p+q equals 4 or less.

In Formula I and Formula Ia, in one embodiment, L3 is a linking group that is selected from:
(i) a C1-C4 alkylene linking group such as methylene or ethylene;
(ii) an ether linking group, such as —(CH$_2$)$_p$O(CH$_2$)$_q$—, where p and q independently represent an integer of from 1 to 3, and p+q equals 4 or less;
(iii) a C2-C4 alkenylene linking group such as ethenylene;
(iv) an ester linking group such as —(CH$_2$)$_p$C(=O)O(CH$_2$)$_q$—, or —(CH$_2$)$_p$OC(=O)(CH$_2$)$_q$—, where p and q each independently represent an integer of from 0 to 3, and p+q equals 4 or less, or an amido linking group, such as —(CH$_2$)$_p$NRzC(=O)(CH$_2$)$_q$—, or —(CH$_2$)$_p$C(=O)NRz(CH$_2$)$_q$—, where p and q independently represent an integer of from 0 to 3, and p+q equals 4 or less, and Rz is H or C1-C3 alkyl;
(v) an amine linker of formula —RxN(Rz)Ry-, for example wherein Rx and Ry are C1-C4 alkylene, e.g. C1 or C2 alkylene, and Rz is H or C1-C4 alkyl, e.g. C1 or C2 alkyl;
(vi) a thioether linker such as —(CH$_2$)$_p$S(CH$_2$)$_q$—, where p and q independently represent an integer of from 1 to 3, and p+q equals 4 or less.

In Formula I and Formula Ia, it is preferred that L3 is a linking group that is a C1-C12 alkylene linking group or a C1-C12 ester linking group, or C1-12 amido linking group, more preferably a C1-C8 alkylene linking group or a C1-C8 ester linking group or C1-8 amido linking group. In one embodiment, the alkylene linking groups are straight chain. In another embodiment, the linking groups are branched alkylene groups. For example, L3 may represent a linking group that is a C1-C12 straight chain alkylene linking group (such as a C1-C8 or C1-C6 straight chain alkylene linking group) or a C2-C12 branched chain alkylene linking group (such as a C2-C8, or C2-C6, or C3-C6 branched chain alkylene linking group) or a C1-C12 (such as a C1-C8 or C1-C6) ester group or a C1-C12 (such as a C1-C8 or C1-C6) amido group.

In Formula I and Formula Ia, it maybe that L3 represents a linking group that is a C1-C6 alkylene linking group or C1-C6 ester group or C1-C6 amido group, more preferably a C1-C5 alkylene linking group or C1-C5 ester group or C1-C5 amido group, such as a C1-C4 alkylene linking group or C1-C4 ester group or C1-C4 amido group. It may therefore be methylene, ethylene, propylene, butylene or pentylene, or an ester linking group —(CH$_2$)$_p$C(=O)O(CH$_2$)$_q$— or —(CH$_2$)$_p$OC(=O)(CH$_2$)$_q$—, where p and q each independently represent an integer of from 0 to 3, especially 0, 1 or 2, and p+q equals 4 or less, especially 3 or less, or an amido group —(CH$_2$)$_p$NRzC(=O)(CH$_2$)$_q$-, or —(CH$_2$)$_p$C(=O)NRz(CH$_2$)$_q$—, where p and q independently represent an integer of from 0 to 3, especially 0, 1 or 2, and p+q equals 4 or less, especially 3 or less, and Rz is H or C1-C3 alkyl, especially H or C1 alkyl.

In one embodiment, of Formula I and Formula Ia, L3 represents a linking group that is a C1-C4 alkylene linking group, such as methylene, ethylene or propylene, or an ester linking group —$(CH_2)_pC(=O)O(CH_2)_q$— or —$(CH_2)_pOC(=O)(CH_2)_q$—, where p and q each independently represent an integer of from 0 to 3, especially 0, 1 or 2, and p+q equals 3 or less, especially 2 or less, or an amido group —$(CH_2)_pNRzC(=O)(CH_2)_q$—, or —$(CH_2)_pC(=O)NRz(CH_2)_q$—, where p and q independently represent an integer of from 0 to 3, especially 0, 1 or 2, and p+q equals 3 or less, especially 2 or less, and Rz is H or C1-C2 alkyl, especially H.

In one embodiment, in Formula I and Formula Ia, L3 is equivalent to $CH_2$-L2.

It may be that the L3 linking group is an O-ester linking group, C-ester linking group, ether linking group, carbonyl linking group, amine linking group, N-amido linking group, C-amido linking group, thioether linking group or alkyl linking group.

In Formula I and Formula Ia, in one embodiment L3 is —$CH_2$—, —$CH_2CH_2$—, —$CH_2CH_2CH_2$—, —$CH_2$O—C(=O)—, —O—C(=O)—, —NH—, —C(=O)—, —C(=O)—$CH_2$—, —O—$CH_2$—C(=O)—, —C(=O)—O—, —NHC(=O)—, —C(=O)NH—, —O—, —$CH_2$—NH—, —$CH_2$—NH—$CH_2$—, —S—, —S—$CH_2$—, —$CH_2$—S—$CH_2$—, or —$CH_2$O.

In Formula I and Formula Ia, in one embodiment L3 is —$CH_2$—, —$CH_2CH_2$—, —$CH_2CH_2CH_2$—, —$CH_2$O—C(=O)—, —$CH_2$—NH—, —$CH_2$—NH—$CH_2$—, —$CH_2$—S—$CH_2$—, or —$CH_2$O.

In one embodiment L3 is —O—C(=O)—, —NH—, —C(=O)—, —C(=O)—$CH_2$—, —O—$CH_2$—C(=O)—, —C(=O)—O—, —NHC(=O)—, —C(=O)NH—, —O—, —$CH_2$—NH—, —$CH_2$—NH—$CH_2$—, —S—, —S—$CH_2$—, —$CH_2$—S—$CH_2$—, or —$CH_2$—O.

In Formula I and Formula Ia, in one embodiment R2 and R3, which may be the same or different, are each a C10-C24 alkyl, alkenyl or alkynyl group, or a derivative thereof. Preferably, R2 and R3, which may be the same or different, are each a C10-C20 alkyl, alkenyl or alkynyl group, or derivative thereof, such as a C10-C18 or a C12-C18 alkyl, alkenyl or alkynyl group, or derivative thereof. It may, for example, be that R2 and R3, which may be the same or different, are each a C12-C24 group, a C12-C20 group or a C14-C20 group.

In Formula I and Formula Ia, in one embodiment R2 and R3, which may be the same or different, are each a C10-C24 alkenyl (or derivative thereof). For example both R2 and R3 may preferably be a straight-chain alkenyl having from 10 to 20 carbon atoms, e.g. a C12-C18 straight chain alkenyl or a C14-18 straight chain alkenyl. In one embodiment all the double bonds are Z-configured. In one embodiment both R2 and R3 are C10-C24 alkenyl groups that have one to five C=C double bonds, e.g. they may each independently be a C12-C18 straight chain alkenyl that has from one to four C=C double bonds, such as a C16, C17 or C18 straight chain alkenyl having from one to three C=C double bonds, e.g. two or three C=C double bonds.

In Formula I and Formula Ia, preferably R2 and R3 are both a C17 alkenyl having three C=C double bonds. More preferably, R2 and R3 are both 8,11,14-heptadecatrienyl.

In Formula I and Formula Ia, in one embodiment L2 and L3, which may be the same or different, are each an O-ester linking group. For example both L2 and L3 may preferably both be a —OC(=O)— linking group.

In a preferred embodiment, in Formula I and Formula Ia, L2 is an O-ester linking group and L3 is $CH_2$-L2. For example L2 may preferably be a —OC(=O)— linking group and L3 is $CH_2$-L2.

As used herein, the term "carbohydrate" refers to a compound comprising carbon atoms, hydrogen atoms and oxygen atoms. A carbohydrate group can comprise atoms in addition to carbon, hydrogen and oxygen, but will contain at least these types of atoms. The term "carbohydrate" encompasses both cyclized and open chain forms of a compound comprising carbon, hydrogen and oxygen. Thus compounds comprising open chains, such as sorbitol and mannitol, are also encompassed by the term "carbohydrate". However, cyclic carbohydrates are preferred. The term "carbohydrate" is intended to be used in its broadest sense to cover sugars and saccharides, such as, but not limited to, monosaccharides, disaccharides, oligosaccharides and polysaccharides. Examples of carbohydrate groups include, but are not limited to, D-arabinose, L-arabinose, D-ribose, L-ribose, D-xylose, L-xylose, D-glucose, L-glucose, D-fructose, L-fructose, D-galactose, L-galactose, D-mannose, L-mannose, D-altrose, L-altrose, D-allose, L-allose, D-gulose L-gulose, D-idose, L-idose, D-talose, L-talose, D-sucrose, L-sucrose and D-lactose.

As used herein, the term "alkyl" refers to a saturated straight-chain or branched-chain alkyl group. Examples of alkyl groups include, but are not limited to, methyl, ethyl, n-propyl, isopropyl, n-butyl, isobutyl, sec-butyl, tert-butyl, pentyl, isopentyl, neo-pentyl, iso-amyl, hexyl, heptyl. octyl, or nonyl.

As used herein, the term "alkenyl" refers to an unsaturated straight-chain or branched-chain hydrocarbon group having one or more carbon-carbon double bonds. Examples of alkenyl groups include, but are not limited to, decenyl, dodecenyl, undecenyl, tridecenyl, tetradecenyl, pentadecenyl, hexadecenyl, heptadecenyl, octadecenyl and nonadecenyl.

As used herein, the term "alkynyl" refers to an unsaturated straight-chain or branched-chain hydrocarbon group having one or more carbon-carbon triple bonds.

As used herein, the term "hydroxyl" refers to —OH.

As used herein, the term "amino" refers to —NRR', wherein R and R' are independently selected from the group consisting of hydrogen, alkyl, heteroalkyl, aryl, carbocyclyl, and heterocyclyl, or where R and R' may be combined to form a heterocyclyl group. Preferably the R and R' have from 0 to 6 carbon atoms, such as from 0 to 4 carbon atoms, e.g. 0 or 1 or 2 carbon atoms.

As used herein, the term "amido" refers to —N(COR)R', wherein R and R' are independently selected from the group consisting of hydrogen, alkyl, heteroalkyl, aryl, carbocyclyl, and heterocyclyl. Preferably the R and R' have from 0 to 6 carbon atoms, such as from 0 to 4 carbon atoms, e.g. 0 or 1 or 2 carbon atoms.

As used herein, the term "carbonyl linking group" refers to a —C(=O)— or —C(=O)—R"— group, wherein R" is selected from the group consisting of alkyl, heteroalkyl, aryl, carbocyclyl, and heterocyclyl. Preferably R" has from 1 to 6 carbon atoms, such as from 1 to 4 carbon atoms, e.g. 1 or 2 carbon atoms.

As used herein, the term "C-ester linking group" refers to a —C(=O)O— or —C(=O)O—R"— group, wherein R" is selected from the group consisting of alkyl, alkenyl, heteroalkyl, aryl, carbocyclyl, and heterocyclyl. Preferably R" has from 1 to 6 carbon atoms, such as from 1 to 4 carbon atoms, e.g. 1 or 2 carbon atoms.

As used herein, the term "O-ester linking group" refers to an —OC(=O)— or an —OC(=O)R"— group, wherein R" is selected from the group consisting of alkyl, alkenyl, heteroalkyl, aryl, carbocyclyl, and heterocyclyl. Preferably R" has from 1 to 6 carbon atoms, such as from 1 to 4 carbon atoms, e.g. 1 or 2 carbon atoms.

As used herein, the term "C-amido linking group" refers to a —C(=O)NH— or —C(=O)NR"— group, wherein R" is selected from the group consisting of alkyl, alkenyl, heteroalkyl, aryl, carbocyclyl, and heterocyclyl. Preferably R" has from 1 to 6 carbon atoms, such as from 1 to 4 carbon atoms, e.g. 1 or 2 carbon atoms.

As used herein, the term "N-amido linking group" refers to an —NHC(=O)— or an —NR"C(=O) group, wherein R" is selected from the group consisting of alkyl, alkenyl, heteroalkyl, aryl, carbocyclyl, and heterocyclyl. Preferably R" has from 1 to 6 carbon atoms, such as from 1 to 4 carbon atoms, e.g. 1 or 2 carbon atoms.

As used herein, the term "ether linking group" refers to a —O—, —O—R"—, —R"—O— or —R"—O—R"— group, wherein R" is selected from the group consisting of alkyl, alkenyl, heteroalkyl, aryl, carbocyclyl, and heterocyclyl. Preferably R" has from 1 to 6 carbon atoms, such as from 1 to 4 carbon atoms, e.g. 1 or 2 carbon atoms.

As used herein, the term "thioether linking group" refers to a —S—, —S—R"—, —R"—S— or —R"—S—R"— group, wherein R" is selected from the group consisting of alkyl, alkenyl, heteroalkyl, aryl, carbocyclyl, and heterocyclyl. Preferably R" has from 1 to 6 carbon atoms, such as from 1 to 4 carbon atoms, e.g. 1 or 2 carbon atoms.

The pharmaceutically acceptable salt may, for example, be one of those set out in P. H. Stahl and C. G. Wermuth, editors, Handbook of Pharmaceutical Salts: Properties, Selection and Use, Weinheim/Zürich:Wiley-VCH/VHCA, 2002.

The compounds of Formula I and Ia may contain one or more asymmetric carbon atoms (chiral centres) and can therefore exist in racemic and optically active forms. The present invention encompasses all stereoisomeric forms of the compounds of Formula I. Thus, optical isomers or enantiomers, racemates, diastereomers, and mixtures of diastereomers, are also encompassed in the compounds of Formula I and Ia.

The present invention therefore relates to a compound of Formula I or Ia, which may be in the form of an enantiomer, a diastereomer, a racemate, or a mixture of diastereomers, and which may be provided in the form of a pharmaceutically acceptable salt or solvate of the stated Formula.

In one embodiment, the product is provided in the form of a mixture of diastereomers; this mixture may have improved solubility properties which in turn can make the compound easier to work with and easier to formulate as a pharmaceutical or neutraceutical composition.

In one embodiment, the compound of Formula I or Ia is of the following formula:

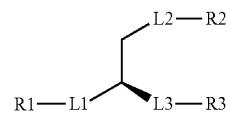
(Ib)

where the groups R1, R2, R3, L1, L2 and L3 may take any of the definitions above.

In one preferred embodiment, the compound of Formula I or Ia is of the following formula:

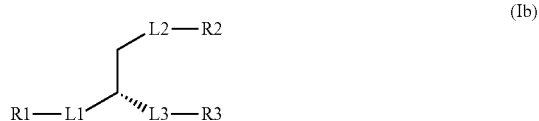
(Ic)

where the groups R1, R2, R3, L1, L2 and L3 may take any of the definitions above.

In one embodiment, the compound of Formula I or Ia is of the following formula:

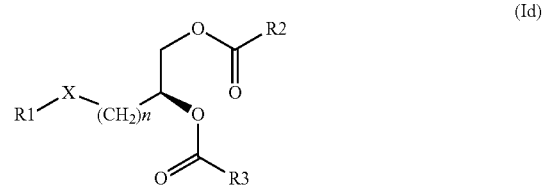
(Id)

wherein the groups R1, R2, R3, may take any of the definitions above, and X is either absent or is —O—, —NR$^a$—, —S— or —CR$^a$R$^b$—, wherein R$^a$ and R$^b$ are independently selected from the group consisting of hydrogen and C1-C4 alkyl, and n is an integer of from 1 to 6, e.g. 1, 2 or 3.

In one embodiment:
R1 is a carbohydrate group or derivative thereof;
X is either absent or is —O—, —NR$^a$—, —S— or —CR$^a$R$^b$—, wherein R$^a$ and R$^b$ are independently selected from the group consisting of hydrogen and C1-C4 alkyl;
n is an integer of from 1 to 6, e.g. 1, 2 or 3;
R2 is a C10-C24 alkyl, alkenyl or alkynyl group or a derivative thereof; and
R3 is a C10-C24 alkyl, alkenyl or alkynyl group or a derivative thereof; In one embodiment, the compound of Formula I or Ia is of the following formula:

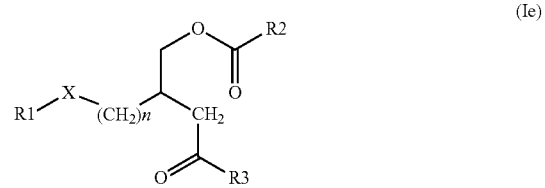
(Ie)

wherein the groups R1, R2, R3, may take any of the definitions above, and X is either absent or is —O—, —NR$^a$—, —S— or —CR$^a$R$^b$—, wherein R$^a$ and R$^b$ are independently selected from the group consisting of hydrogen and C1-C4 alkyl, and n is an integer of from 1 to 6, e.g. 1, 2 or 3.

In one embodiment:
R1 is a carbohydrate group or derivative thereof;
X is either absent or is —O—, —NR$^a$—, —S— or —CR$^a$R$^b$—, wherein R$^a$ and R$^b$ are independently selected from the group consisting of hydrogen and C1-C4 alkyl;
n is an integer of from 1 to 6, e.g. 1, 2 or 3;
R2 is a C10-C24 alkyl, alkenyl or alkynyl group or a derivative thereof; and
R3 is a C10-C24 alkyl, alkenyl or alkynyl group or a derivative thereof;

In one embodiment, the compound of Formula I or Ia is of the following formula:

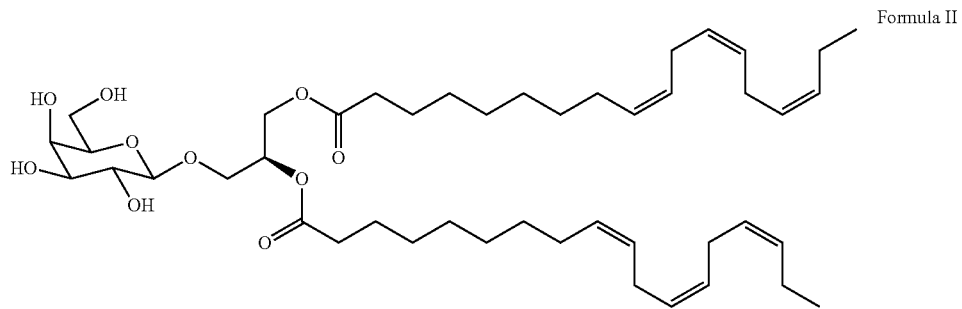 [SMILES: CC/C=C\C/C=C\C/C=C\CCCCCCCC(=O)OC[C@H](COC1OC(CO)C(O)C(O)C1O)OC(=O)CCCCCCC/C=C\C/C=C\C/C=C\CC]
Formula II

In one embodiment, the compound of Formula I or Ia is 1,2-dioctadecatienyl-3-O-β-D-galactosyl-sn-glycerol.

In one embodiment, the compound of Formula I or Ia is $C_{45}H_{74}O_{10}$.

In one embodiment, the compound of Formula I or Ia is of the following formula:

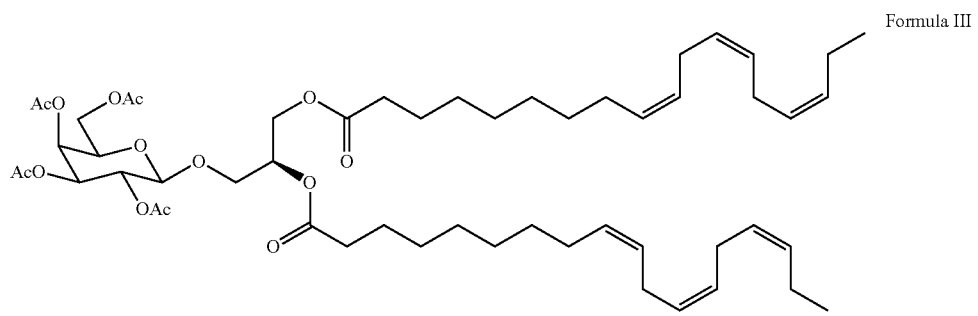 [SMILES: CC/C=C\C/C=C\C/C=C\CCCCCCCC(=O)OC[C@H](COC1OC(COC(C)=O)C(OC(C)=O)C(OC(C)=O)C1OC(C)=O)OC(=O)CCCCCCC/C=C\C/C=C\C/C=C\CC]
Formula III

In one embodiment, the compound of Formula I or Ia is $C_{53}H_{82}O_{14}$

In one embodiment, the compound of Formula I or Ia is of the following formula:

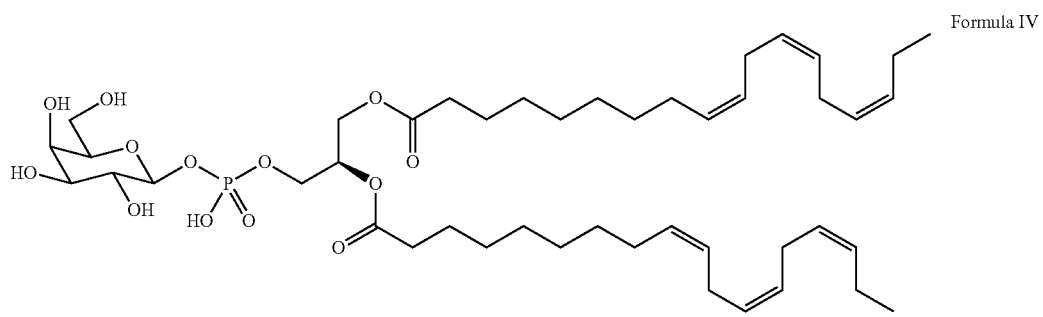 [SMILES: CC/C=C\C/C=C\C/C=C\CCCCCCCC(=O)OC[C@H](COP(=O)(O)OC1OC(CO)C(O)C(O)C1O)OC(=O)CCCCCCC/C=C\C/C=C\C/C=C\CC]
Formula IV

In one embodiment, the compound of Formula I or Ia is $C_{45}H_{75}O_{13}P$.

In one embodiment, the compound of Formula I or Ia is of the following formula:

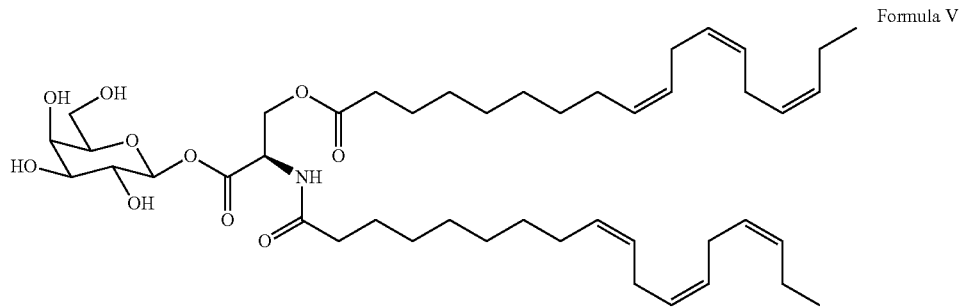 [SMILES: CC/C=C\C/C=C\C/C=C\CCCCCCCC(=O)N[C@H](COC(=O)CCCCCCC/C=C\C/C=C\C/C=C\CC)C(=O)OC1OC(CO)C(O)C(O)C1O]

Formula V

In one embodiment, the compound of Formula I or Ia is $C_{45}H_{73}O_{10}N$.

In one embodiment, the compound of Formula I or Ia is of the following formula:

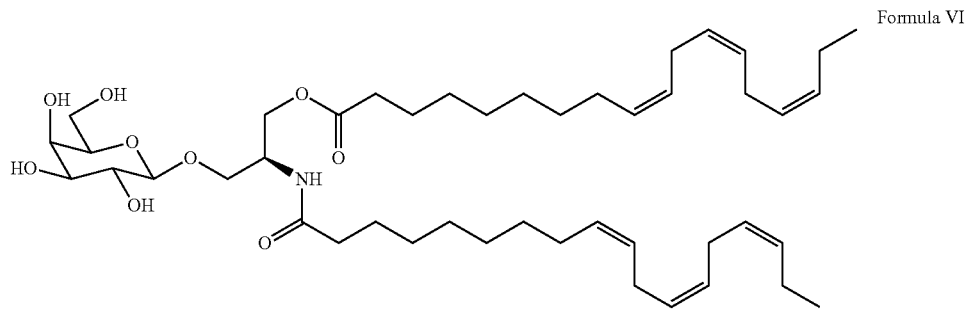 [SMILES: CC/C=C\C/C=C\C/C=C\CCCCCCCC(=O)N[C@H](COC(=O)CCCCCCC/C=C\C/C=C\C/C=C\CC)COC1OC(CO)C(O)C(O)C1O]

Formula VI

In one embodiment, the compound of Formula I or Ia is $C_{45}H_{75}O_9N$.

In one embodiment, the compound of Formula I or Ia is a galactolipid, preferably a glyco-glycerolipid.

In one embodiment, the compound of Formula I or Ia is 1,2-dioctadecatienyl-3-O-β-D-galactosyl-sn-glycerol.

In one embodiment, the compound of Formula I or Ia is $C_{45}H_{74}O_{10}$. In another embodiment, the compound of Formula I or Ia is $C_{53}H_{82}O_{14}$.

In one embodiment, the compound of Formula I or Ia is of the following formula:

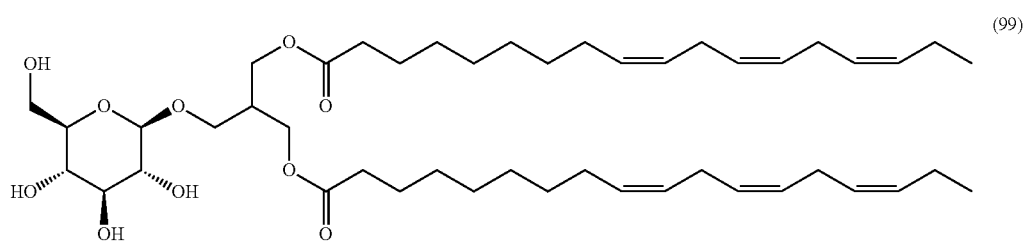 [SMILES: CC/C=C\C/C=C\C/C=C\CCCCCCCC(=O)OCC(COC(=O)CCCCCCC/C=C\C/C=C\C/C=C\CC)CO[C@@H]1O[C@H](CO)[C@@H](O)[C@H](O)[C@H]1O]

(99)

In one embodiment, the compound of Formula I or Ia is of the following formula:
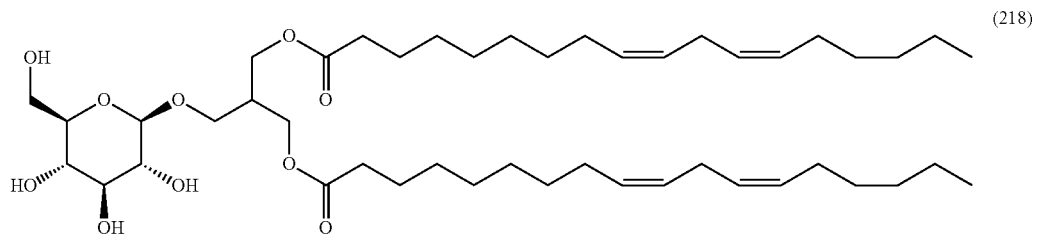 [SMILES: CCCCC/C=C\C/C=C\CCCCCCCC(=O)OCC(COC(=O)CCCCCCC/C=C\C/C=C\CCCCC)CO[C@@H]1O[C@H](CO)[C@@H](O)[C@H](O)[C@H]1O]
(218)
In one embodiment, the compound of Formula I or Ia is of the following formula:
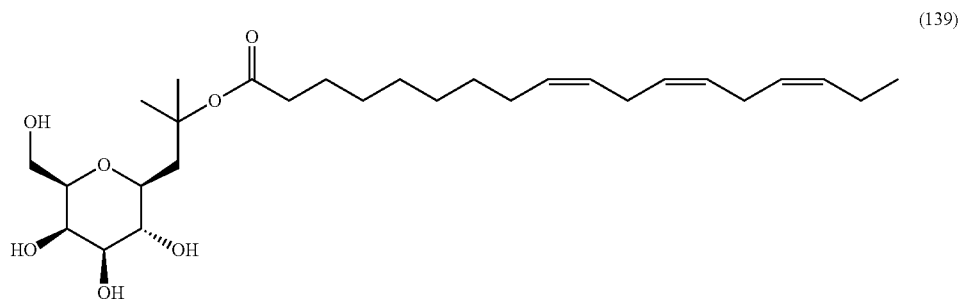 [SMILES: CC/C=C\C/C=C\C/C=C\CCCCCCCC(=O)OC(C)(C)C[C@@H]1O[C@H](CO)[C@H](O)[C@H](O)[C@H]1O]
(139)
In one embodiment, the compound of Formula I or Ia is of the following formula:
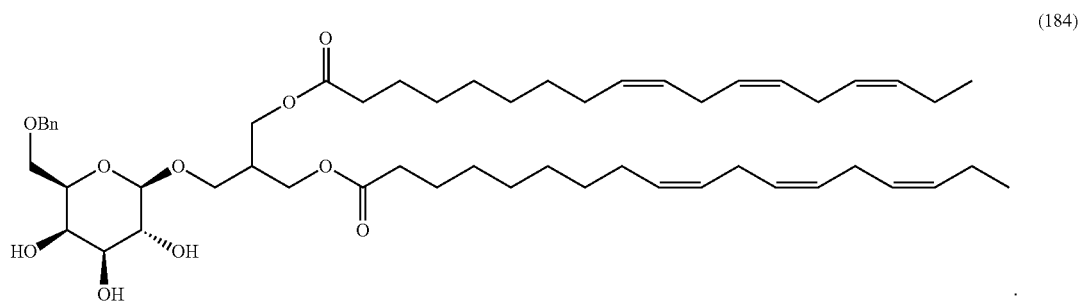 [SMILES: CC/C=C\C/C=C\C/C=C\CCCCCCCC(=O)OCC(COC(=O)CCCCCCC/C=C\C/C=C\C/C=C\CC)CO[C@@H]1O[C@H](COCc2ccccc2)[C@H](O)[C@H](O)[C@H]1O]
(184)
In one embodiment, the compound of Formula I or Ia is of the following formula:
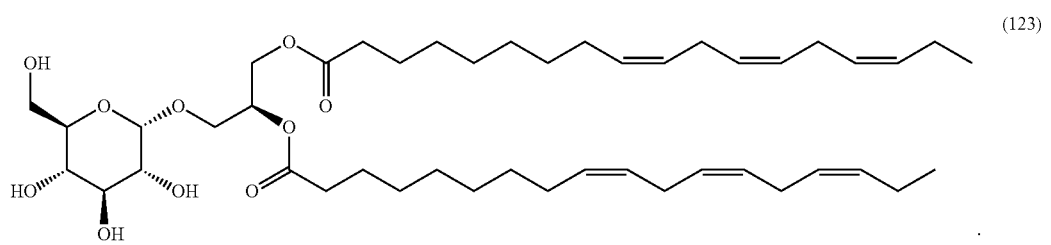 [SMILES: CC/C=C\C/C=C\C/C=C\CCCCCCCC(=O)OC[C@H](CO[C@H]1O[C@H](CO)[C@@H](O)[C@H](O)[C@H]1O)OC(=O)CCCCCCC/C=C\C/C=C\C/C=C\CC]
(123)

In one embodiment, the compound of Formula I or Ia is of the following formula:
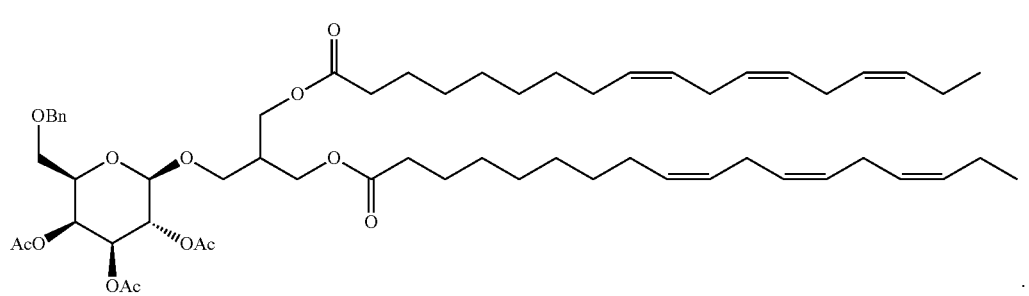
(180)
In one embodiment, the compound of Formula I or Ia is of the following formula:
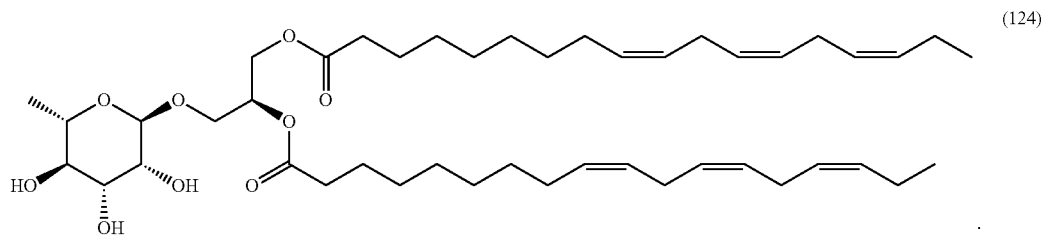 [SMILES: CC/C=C\C/C=C\C/C=C\CCCCCCCC(=O)OC[C@H](CO[C@@H]1O[C@@H](C)[C@H](O)[C@@H](O)[C@H]1O)OC(=O)CCCCCCC/C=C\C/C=C\C/C=C\CC]
(124)
In one embodiment, the compound of Formula I or Ia is of the following formula:
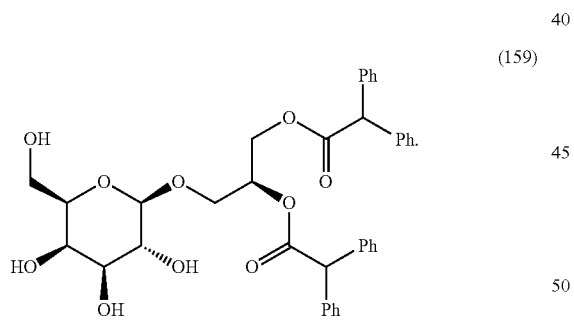
(159)
In one embodiment, the compound of Formula I or Ia is of the following formula:
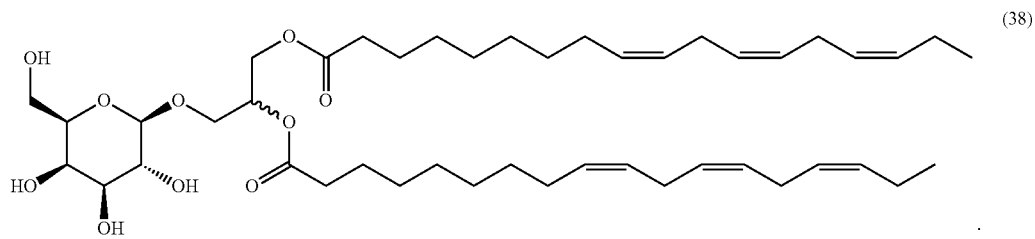 [SMILES: CC/C=C\C/C=C\C/C=C\CCCCCCCC(=O)OCC(CO[C@@H]1O[C@H](CO)[C@H](O)[C@H](O)[C@H]1O)OC(=O)CCCCCCC/C=C\C/C=C\C/C=C\CC]
(38)

In one embodiment, the compound of Formula I or Ia is of the following formula:
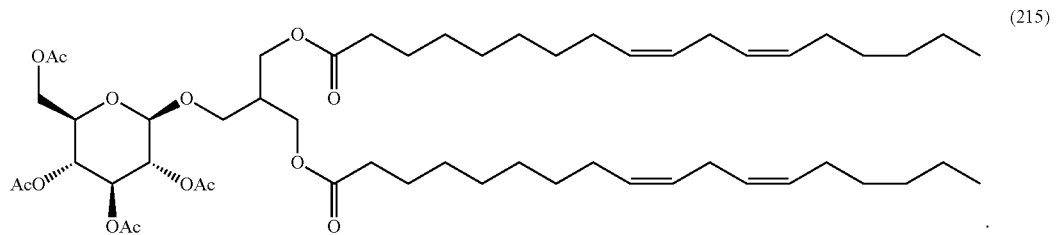 [SMILES: CCCCC/C=C\C/C=C\CCCCCCCC(=O)OCC(COC(=O)CCCCCCC/C=C\C/C=C\CCCCC)CO[C@@H]1O[C@H](COC(C)=O)[C@@H](OC(C)=O)[C@H](OC(C)=O)[C@H]1OC(C)=O]
(215)
In one embodiment, the compound of Formula I or Ia is of the following formula:
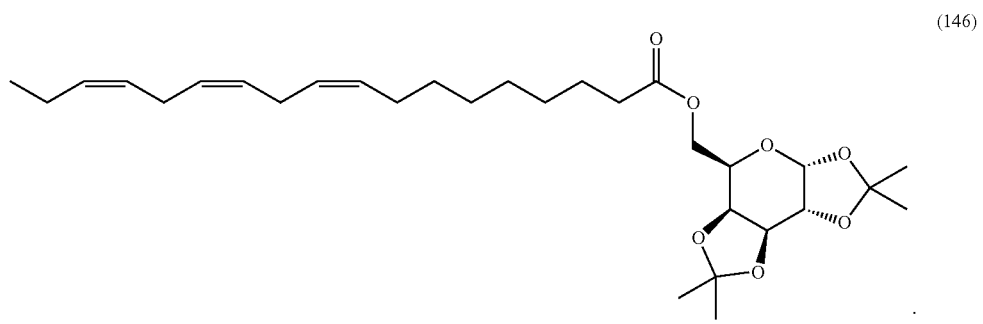 [SMILES: CC/C=C\C/C=C\C/C=C\CCCCCCCC(=O)OC[C@H]1O[C@@H]2OC(C)(C)O[C@@H]2[C@H]2OC(C)(C)O[C@H]21]
(146)
In one embodiment, the compound of Formula I or Ia is of the following formula:
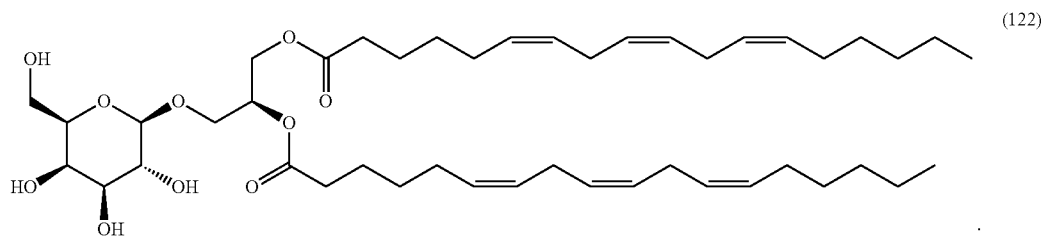 [SMILES: CCCCC/C=C\C/C=C\C/C=C\CCCCC(=O)OC[C@H](CO[C@@H]1O[C@H](CO)[C@H](O)[C@H](O)[C@H]1O)OC(=O)CCCC/C=C\C/C=C\C/C=C\CCCCC]
(122)
In one embodiment, the compound of Formula I or Ia is of the following formula:
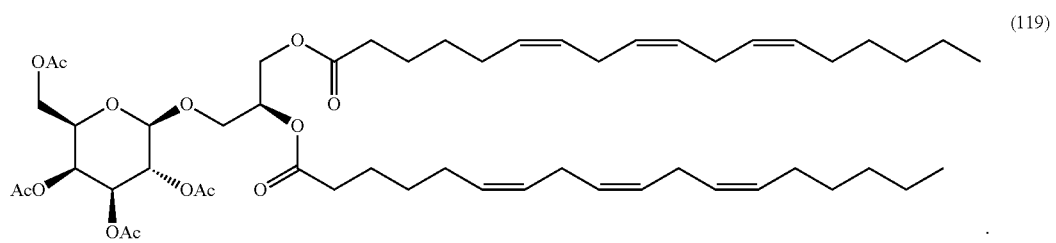 [SMILES: CCCCC/C=C\C/C=C\C/C=C\CCCCC(=O)OC[C@H](CO[C@@H]1O[C@H](COC(C)=O)[C@H](OC(C)=O)[C@H](OC(C)=O)[C@H]1OC(C)=O)OC(=O)CCCC/C=C\C/C=C\C/C=C\CCCCC]
(119)

In one embodiment, the compound of Formula I or Ia is of the following formula:
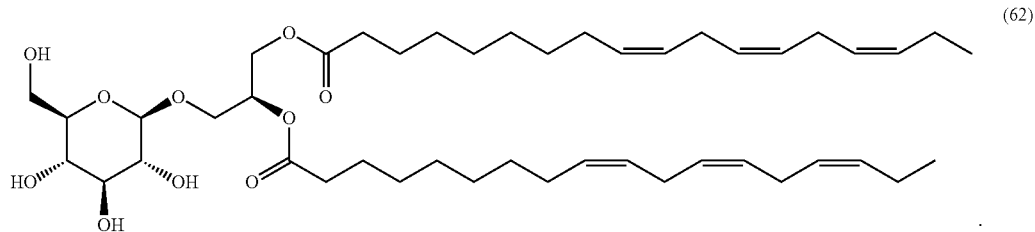 [SMILES: CC/C=C\C/C=C\C/C=C\CCCCCCCC(=O)OC[C@H](CO[C@@H]1O[C@H](CO)[C@@H](O)[C@H](O)[C@H]1O)OC(=O)CCCCCCC/C=C\C/C=C\C/C=C\CC]
(62)
In one embodiment, the compound of Formula I or Ia is of the following formula:
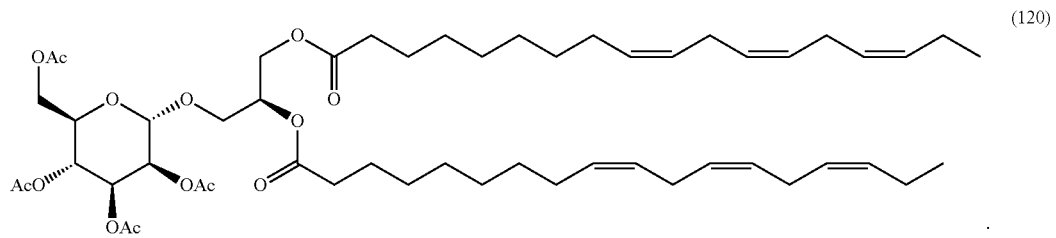 [SMILES: CC/C=C\C/C=C\C/C=C\CCCCCCCC(=O)OC[C@H](CO[C@H]1O[C@H](COC(C)=O)[C@@H](OC(C)=O)[C@H](OC(C)=O)[C@@H]1OC(C)=O)OC(=O)CCCCCCC/C=C\C/C=C\C/C=C\CC]
(120)
In one embodiment, the compound of Formula I or Ia is of the following formula:
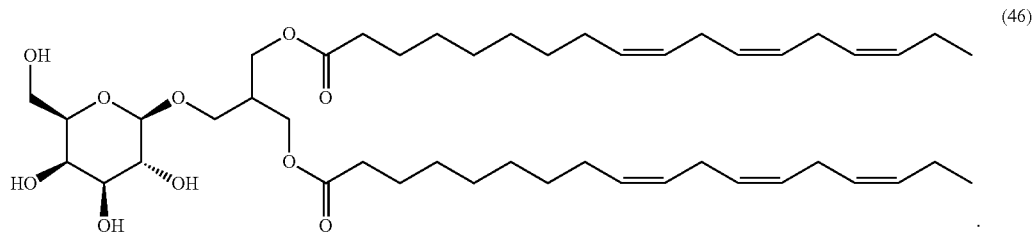 [SMILES: CC/C=C\C/C=C\C/C=C\CCCCCCCC(=O)OCC(COC(=O)CCCCCCC/C=C\C/C=C\C/C=C\CC)CO[C@@H]1O[C@H](CO)[C@H](O)[C@H](O)[C@H]1O]
(46)
In one embodiment, the compound of Formula I or Ia is of the following formula:
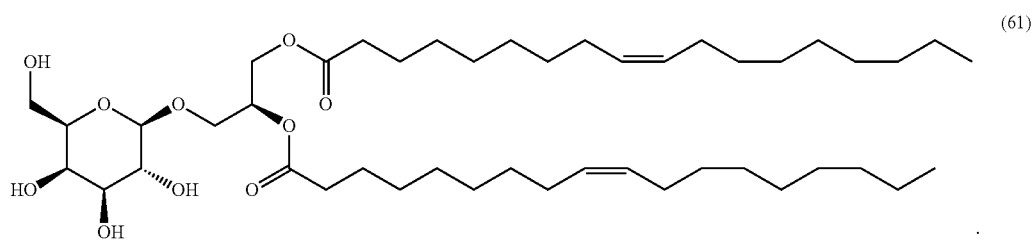 [SMILES: CCCCCCCC/C=C\CCCCCCCC(=O)OC[C@H](CO[C@@H]1O[C@H](CO)[C@H](O)[C@H](O)[C@H]1O)OC(=O)CCCCCCC/C=C\CCCCCCCC]
(61)

In one embodiment, the compound of Formula I or Ia is of the following formula:
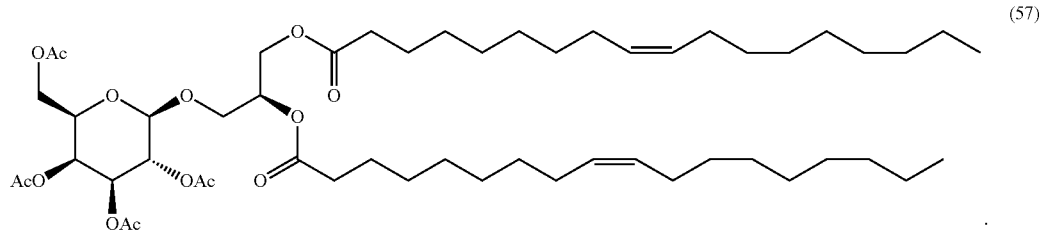 [SMILES: CCCCCCCC/C=C\CCCCCCCC(=O)OC[C@H](CO[C@@H]1O[C@H](COC(C)=O)[C@H](OC(C)=O)[C@H](OC(C)=O)[C@H]1OC(C)=O)OC(=O)CCCCCCC/C=C\CCCCCCCC]
(57)
In one embodiment, the compound of Formula I or Ia is of the following formula:
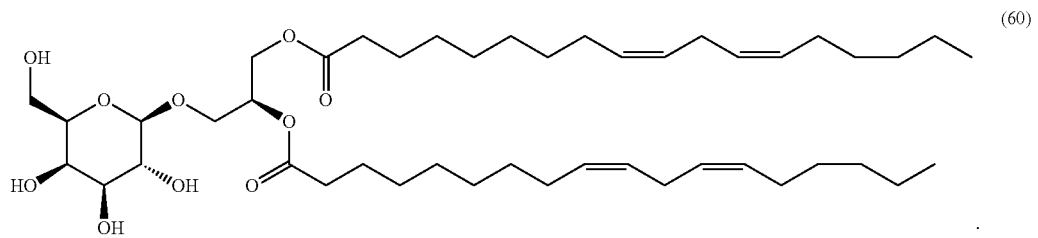 [SMILES: CCCCC/C=C\C/C=C\CCCCCCCC(=O)OC[C@H](CO[C@@H]1O[C@H](CO)[C@H](O)[C@H](O)[C@H]1O)OC(=O)CCCCCCC/C=C\C/C=C\CCCCC]
(60)
In one embodiment, the compound of Formula I or Ia is of the following formula:
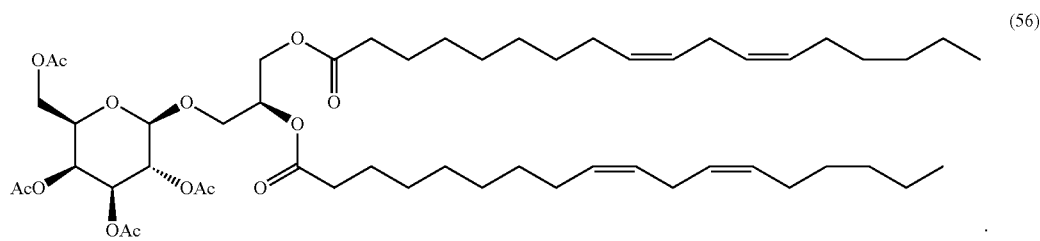 [SMILES: CCCCC/C=C\C/C=C\CCCCCCCC(=O)OC[C@H](CO[C@@H]1O[C@H](COC(C)=O)[C@H](OC(C)=O)[C@H](OC(C)=O)[C@H]1OC(C)=O)OC(=O)CCCCCCC/C=C\C/C=C\CCCCC]
(56)
In one embodiment, the compound of Formula I or Ia is of the following formula:
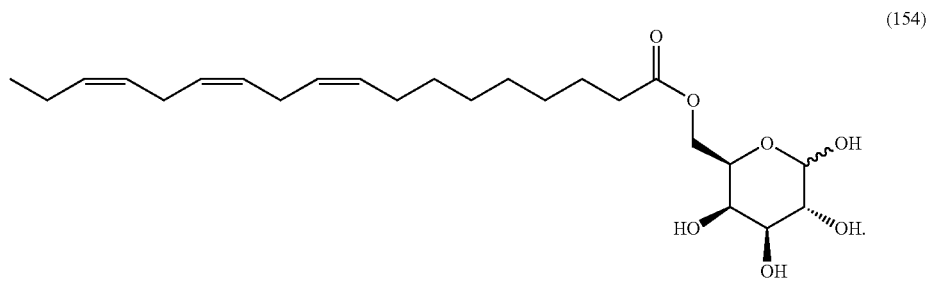 [SMILES: CC/C=C\C/C=C\C/C=C\CCCCCCCC(=O)OC[C@H]1OC(O)[C@H](O)[C@@H](O)[C@H]1O]
(154)

In one embodiment, the compound of Formula I or Ia is of the following formula:

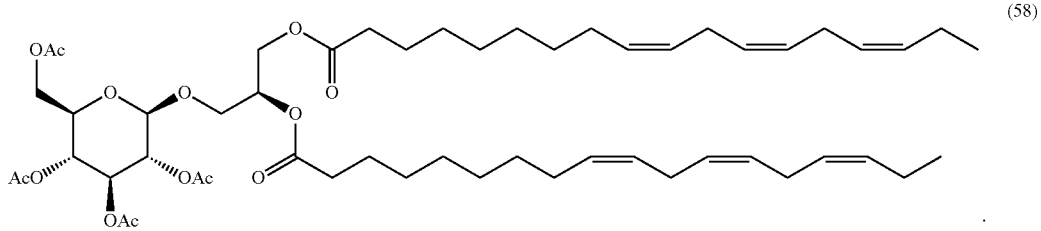 [SMILES: CC/C=C\C/C=C\C/C=C\CCCCCCCC(=O)OC[C@H](CO[C@@H]1O[C@H](COC(C)=O)[C@@H](OC(C)=O)[C@H](OC(C)=O)[C@H]1OC(C)=O)OC(=O)CCCCCCC/C=C\C/C=C\C/C=C\CC]

(58)

The compound of the invention may consist of any one of compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17).

The compound of the invention may consist of any one of compounds selected from the group comprising compounds 99, 218, 139, 184, 123, 180, 124, 159, 215, 146, 122, 119, 62, 120, 46, 61, 57, 60, 56, 154, and 58 (as shown in FIG. 16 or 17).

The compound of the invention may consist of any one of compounds selected from the group comprising compounds 99, 218, 139, 184, 123, 180, 124, 159, 215, 146, 122, 119, 62, 120, and 46 (as shown in FIG. 16).

The compound of the invention may consist of any one of compounds selected from the group comprising compounds 99, 218, 139, 184, 123, 180, 124, 122, 119, 62, 120, and 46 (as shown in FIG. 16).

The compound of the invention may consist of any one of compounds selected from the group comprising compounds 99, 218, 139, 184, 123, 180, and 124 (as shown in FIG. 16).

A compound of Formula I or Ia may be chemically synthesised or may be isolated from a natural source, for example a plant.

As discussed further in the examples, synthesis of glycoglycerol lipids and the like is well known and the skilled man could readily make the compounds of the invention by using and modifying known reaction mechanisms, such as that described in Manzo, E.; Letizia Ciavatta, M.; Pagano, D.; Fontana, A. *Tetrahedron Lett.* 2012, 53, 879. Alternatively, some glycoglycerol lipids and the like are naturally occurring and so may be isolated from plant materials, for example tomatoes.

The invention further provides a pharmaceutical composition comprising:
a compound of Formula I or Ia, or a pharmaceutically acceptable salt thereof; and
a pharmaceutically acceptable carrier, diluent or excipient.

The carrier may, for example, be water or an aqueous fluid such as saline. However, the skilled person will be well aware of carriers, diluents or excipients that are pharmaceutically acceptable.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

The pharmaceutical composition may also comprise, in addition to a compound of Formula I or Ia, or a pharmaceutically acceptable salt thereof, at one or more further anti-cancer agent, such as a chemotherapeutic agent.

The pharmaceutical composition may comprise (i) a compound selected from the group consisting of compounds 99, 218, 139, 184, 123, 180, 124, 38, 122, 119, 62, 120, 46, 61, 57, 60, 56, 154, and 58, and combinations thereof, and (ii) at least one further anti-cancer agent, such as a chemotherapeutic agent.

Alternatively, the pharmaceutical composition may comprise (i) a compound selected from the group consisting of compounds 99, 218, 139, 184, 123, 180, 124, 38, 122, 119, 62, 120, and 46, and combinations thereof, and (ii) at least one further anti-cancer agent, such as a chemotherapeutic agent.

Further alternatively, the pharmaceutical composition may comprise (i) a compound selected from the group consisting of compounds 61, 57, 60, 56, 154, and 58, and combinations thereof, and (ii) at least one further anti-cancer agent, such as a chemotherapeutic agent.

The anti-cancer agent, such as a chemotherapeutic agent, may comprise cis-diamminedichloroplatinum(II) (Cisplatin™) or (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione (Doxorubicin™), or any other chemotherapeutic agent.

The invention further provides a nutraceutical composition comprising a compound of Formula I or Ia. The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

The nutraceutical composition may comprise:
a compound of Formula I or Ia, or a pharmaceutically acceptable salt thereof; and
a nutraceutically acceptable carrier, diluent or excipient.

The carrier may, for example, be water or an aqueous fluid such as saline or a sugar solution. However, the skilled person will be well aware of carriers, diluents or excipients that are nutraceutically acceptable.

The invention may provide in another aspect a compound of Formula I or Ia or a pharmaceutically acceptable salt thereof, for use as an inhibitor of protein translation. More preferably a compound of the invention may inhibit protein translation by inhibiting eukaryotic ribosome activity, in particular, ribosome recruitment. The compound may selectively inhibit eIF4A dependent or independent translation.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

A compound of the invention may inhibit protein translation by selectively reducing translation of mRNAs with long structured UTRs.

According to a further aspect the invention provides an inhibitor of protein translation comprising the compound of Formula I or Ia, or a pharmaceutically acceptable salt thereof, for example, the compound of Formula II.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

According to a still further aspect the invention provides a compound of Formula I or Ia or a pharmaceutically acceptable salt thereof, for example, the compound of Formula II, for use as an inhibitor of protein translation.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

According to a yet further aspect the invention provides an adjuvant and/or a chemotherapeutic agent and/or an antiproliferative agent and/or an antiviral agent and/or a cell sensitising agent comprising a compound of Formula I or Ia, or a pharmaceutically acceptable salt thereof. The invention also provides a compound of Formula I or Ia or a pharmaceutically acceptable salt thereof, for example, the compound of Formula II, for use as one or more of an adjuvant, a chemotherapeutic agent, an antiproliferative agent, an antiviral agent and a cell sensitising agent.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

In embodiments or aspects of the invention directed to antiviral compounds, or methods of use in the prevention or treatment of viral infection, the virus may be selected from any of the group comprising Herpes Simplex Virus (HSV); HIV; influenza virus; Coronaviruses; Rhinovirus; and Human Cytomegalovirus (HCMV); or combinations thereof.

In a still further alternative aspect, the invention provides a compound of Formula I or Ia, or a pharmaceutically acceptable salt thereof, for use in the treatment of a disease or condition selected from the group comprising cancer, Alzheimer's disease, Parkinson's disease, Huntingdon's disease, muscle wasting and autistic spectrum disorders. Preferably a compound of Formula I or Ia, or a pharmaceutically acceptable salt thereof, is for use in the treatment of cancer.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

The cancer may be selected from carcinoma, lymphoma, blastoma, sarcoma, and leukemia. More particularly, examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, renal cancer, vulval cancer, thyroid cancer, hepatic carcinoma, gastric cancer, melanoma, and various types of head and neck cancer. The cancer may be selected from breast, lung or ovarian cancer.

In a further alternative aspect, the invention provides a compound of Formula I or Ia, or a pharmaceutically acceptable salt thereof, for use in the treatment of a disease or condition which is caused by dysregulation of protein translation.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

The disease or condition may be selected from the group comprising cancer, Alzheimer's disease, Parkinson's disease, Huntingdon's disease, muscle wasting and autistic spectrum disorders. The disease or condition may be selected from the group comprising cancer, Alzheimer's disease and autistic spectrum disorders. The disease or condition may be cancer.

A cell sensitising agent may act to sensitise cells to subsequent or simultaneous treatment with another active agent. For example, a cell sensitising cell may act to sensitise cell to an anti-cancer agent, such as a chemotherapeutic agent, such that the anti-cancer agent is more efficacious or is efficacious at lower doses.

The compound of Formula I or Ia or pharmaceutical salts thereof may have an additive therapeutic effect when administered in combination with an anti-cancer agent, such as a chemotherapeutic agent.

The compound selected from any one of the group comprising compounds 99, 218, 139, 184, 123, 180, 124, 38, 122, 119, 62, 120, 46, 61, 57, 60, 56, 154, and 58, or combinations thereof, or pharmaceutical salts thereof, may be used in combination with at least one further anti-cancer agent such as a chemotherapeutic agent.

The compound selected from any one of the group comprising compounds 99, 218, 139, 184, 123, 180, 124, 159, 38, 122, 119, 62, 120, and 46, or combinations thereof, or pharmaceutical salts thereof, may be used in combination with at least one further anti-cancer agent such as a chemotherapeutic agent.

The compound selected from any one of the group comprising compounds 61, 57, 60, 56, 154, and 58, or combinations thereof, or pharmaceutical salts thereof, may be used in combination with at least one further anti-cancer agent such as a chemotherapeutic agent.

In another aspect the invention provides a compound of Formula I or Ia or a pharmaceutically acceptable salt thereof for use in the treatment of a disease or condition, wherein the compound of Formula I or Ia or a pharmaceutically acceptable salt thereof is administered as a first therapeutic agent, and a further therapeutic agent is administered as a second therapeutic agent wherein the dosage, preferably the daily dosage, of the second therapeutic agent is significantly reduced (e.g. by 10% or more, or 20% or more, or 30% or more) compared to the daily dosage of the second therapeutic agent when administered alone.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

The first therapeutic agent may comprise a compound selected from any one of the group comprising compounds 99, 218, 139, 184, 123, 180, 124, 38, 122, 119, 62, 120, 46, 61, 57, 60, 56, 154, and 58, or combinations thereof or pharmaceutical salts thereof.

Alternatively, the first therapeutic agent may comprise a compound selected from any one of the group comprising compounds 99, 218, 139, 184, 123, 180, 124, 159, 38, 122, 119, 62, 120, and 46, or combinations thereof or pharmaceutical salts thereof.

Alternatively, the first therapeutic agent may comprise a compound selected from any one of the group comprising compounds 61, 57, 60, 56, 154, and 58, or combinations thereof or pharmaceutical salts thereof.

Preferably the first and second therapeutic agents are for the treatment of cancer; the first therapeutic agent may be a cell sensitising agent which sensitises cells to the action of the second therapeutic agent. Preferably the second therapeutic agent is an anti-cancer agent, preferably a chemotherapeutic agent. The first and second therapeutic agents may be administered simultaneously, sequentially or separately. The amount of anti-cancer drug, in particular chemotherapeutic agent, needed to be efficacious against a particular cancer may be reduced between about 5 and about 100 fold by administering a compound of Formula I or Ia. The daily dose of the chemotherapeutic agent may be reduced by about 5 to about 100 fold, preferably at least about 5 fold, more preferably about 5 to about 50 fold, or about 5 to about 40 fold, or about 20 to about 50 fold, or about 20 to about 40 fold, or about 40 fold.

In another aspect the invention provides a method of reducing the dosage required of an anti-cancer agent, the method comprising administering to a subject with cancer or to cancer cells an amount of a compound of Formula I or Ia, or a pharmaceutically acceptable salt thereof, effective to sensitise the cancer cells to the anticancer agent. The anti-cancer agent may be a chemotherapeutic agent.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

In a yet further aspect the invention provides a method of enhancing the therapeutic activity of an anti-cancer agent which comprises administering to a patient an amount of a compound of Formula I or Ia, or a pharmaceutically acceptable salt thereof, effective to sensitise cancer cells in the patient to the anti-cancer agent. The compound of Formula I or Ia may be administered simultaneously, sequentially or separately to the anti-cancer agent.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

The compound of Formula I or Ia may be used to sensitise cells, such as cancer cells, to known chemotherapeutic agents, for example to cis-diamminedichloroplatinum(II) (Cisplatin™) or (7S,9S)-7-[(2R,4S,5 S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione (Doxorubicin™), or to any other chemotherapeutic agent.

A chemotherapeutic agent is a chemical compound useful in the treatment of cancer. Examples of chemotherapeutic agents include chemical compounds useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBl-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammall and calicheamicin omegall (see, e.g., Agnew, Chem Intl. Ed. Engl, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAM YCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY1 17018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

In one embodiment, the second therapeutic agent is cis-diamminedichloroplatinum(II) (Cisplatin™) or (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione (Doxorubicin™), or any other chemotherapeutic agent.

Depending on the type and severity of the disease or condition to be treated the therapeutic dose of a compound of Formula I or Ia or salt thereof may vary.

For example, for the treatment of cancer, wherein the compound of Formula I or Ia or salt thereof is being used as a chemotherapeutic agent the dose used may be between about 30 mg and about 1200 mg per day. The compound of Formula I or Ia or salt thereof may be administered in a single dose, or in multiple doses. The multiple doses may be administered over the course of one day or over several days, for example over 2 or 3 days, or over 4 or 5 days or more. The dose per day may be between about 60 and 300 mg per 70 kg of subject weight per day.

For example, for the treatment of Alzheimer's disease, Parkinson's disease, Huntingdon's disease, muscle wasting, viral infection or autistic spectrum disorders the dose of a compound of Formula I or Ia or salt thereof used may be between about 3 mg and about 120 mg per day. The compound of Formula I or Ia or salt thereof may be administered in a single dose, or in multiple doses. The multiple doses may be administered over the course of one day or over several days, for example over 2 or 3 days, or over 4 or 5 days or more. The dose per day may be between about 6 and 30 mg per 70 kg of subject weight per day.

For example, for the treatment of cancer, wherein the compound of Formula I or Ia or salt thereof is being used to sensitise cancer cells to a different chemotherapeutic agent the dose used may be between about 3 mg and about 1200 mg per day. The compound of Formula I or Ia or salt thereof may be administered in a single dose, or in multiple doses. The multiple doses may be administered over the course of one day or over several days, for example over 2 or 3 days, or over 4 or 5 days or more. The dose per day may be between about 60 and 300 mg per 70 kg of subject weight per day. The dose per day may be between about 10 and 70 mg per 70 kg of subject weight per day. This may allow the dose of chemotherapeutic agent to be reduced by at least about 5 fold compared the dose of chemotherapeutic agent recommended in the absence of a compound of Formula I or Ia or salt thereof. The daily dose of a chemotherapeutic agent may be reduced by about 5 to about 100 fold, preferably at least about 5 fold, more preferably about 5 to about 50 fold, or about 5 to about 40 fold, or about 20 to about 50 fold, or about 20 to about 40 fold, or about 40 fold.

According to a further aspect the invention provides a method of inhibiting protein translation comprising administering a composition or compound of Formula I or Ia or a pharmaceutically acceptable salt thereof according to the invention to a cell or a subject.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

According to another aspect the invention provides a method of treating a disease or disorder, such as cancer, Alzheimer's disease, Parkinson's disease, Huntingdon's disease, muscle wasting, viral infection or autistic spectrum disorders, in a subject in need thereof, comprising administering to the subject a therapeutically effective amount of a compound of Formula I or Ia or a pharmaceutically acceptable salt thereof.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

The compound of Formula I or Ia or salt thereof may be administered alone or in combination with another active agent. For example, to treat cancer, the compound of Formula I or Ia or salt thereof may be administered in combination with a chemotherapeutic agent. Administration of the compound of Formula I or Ia or salt thereof may mean that the chemotherapeutic agent is more effective or is effective at a lower dose.

In one embodiment, compound 99, 218, 139, 184, 123, 180, 124, 159, 38, 215, 146, 122, 119, 62, 120, or 46 is administered alone.

In one embodiment, compound 61, 57, 60, 56, 154, or 58 is administered in combination with another active agent. In another embodiment, compound 99, 218, 139, 184, 123, 180, 124, 38, 122, 119, 62, 120, 46, 61, 57, 60, 56, 154, or 58 is administered in combination with another active agent.

The compound or composition according to the invention may act as an antiproliferative agent slowing the proliferation of cells, in particular cancer cells.

According to another aspect, the invention provides the use of a compound of Formula I or Ia, or a pharmaceutically acceptable salt thereof, in the manufacture of a medicament for the treatment of a disease or condition which is caused by dysregulation of protein translation.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

In a still further aspect, the invention provides the use of a compound of Formula I or Ia, or a pharmaceutically acceptable salt thereof, in the manufacture of a medicament for use in the treatment of a disease or condition selected from the group comprising cancer, Alzheimer's disease, Parkinson's disease, Huntingdon's disease, muscle wasting, viral infection and autistic spectrum disorders. Preferably the medicament is for use in the treatment of cancer.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

The invention may further provide a product containing at least a compound of Formula I or Ia or a pharmaceutically acceptable salt thereof and a chemotherapeutic agent as a combined preparation for simultaneous, separate or sequential use in an anticancer therapy. The compound of Formula I or Ia or salt thereof and the chemotherapeutic agent may be provided in the same or different preparations.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

In another aspect the invention provides a kit comprising as a first therapeutic agent a compound of Formula I or Ia, or a pharmaceutically acceptable salt thereof, and as a second therapeutic agent an anti-cancer agent, wherein the anti-cancer agent is provided in a form suitable for, and/or with instructions for, administration in a daily dosage which is significantly reduced (e.g. by 10% or more, or 20% or more, or 30% or more) compared to the dosage of the anti-cancer agent if administered alone. The first and second therapeutic agents may be intended to be administered simultaneously, sequentially or separately. The anti-cancer agent may be an chemotherapeutic agent.

The compound of Formula I or Ia, or the pharmaceutically acceptable salt thereof, may be according to any of the definitions given above.

The compound may optionally be according to any of Formulae (Ib), (Ic), (Id), (Ie), II, III, IV, V, or VI. The compound may consist of any one of the compounds selected from the group comprising compounds 99, 218, 139, 184, 123, 180, 124, 159, 38, 215, 146, 122, 119, 62, 120, 46, 61, 57, 60, 56, 154, and 58 (as shown in FIG. 16 or 17), or mixtures thereof, or pharmaceutically acceptable salts thereof. For example, the compound may consist of any one of the compounds selected from the group comprising compounds 99, 218, 139, 184, 123, 180, 124, 122, 119, 62, 120, and 46 (as shown in FIG. 16) or mixtures thereof, or pharmaceutically acceptable salts thereof.

Preferably compounds of Formula I or Ia do not have any significant side effects when administered to a subject. Preferably at the doses required for efficacy the compounds are not toxic to a subject.

The compound of the invention of Formula I or Ia may be formulated as a prodrug or a protected formula. The compound may be a prodrug or a protected form of the compound which releases the compound after administration to a subject. For example, the compound may carry a protective group which is split off by hydrolysis in body fluids, e.g., in the bloodstream, thus releasing the active compound or is oxidized or reduced in body fluids to release the compound. Reference to a "prodrug" is intended to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" may include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in the compounds of the invention and the like.

A discussion of prodrugs may be found in "Smith and Williams' Introduction to the Principles of Drug Design," H. J. Smith, Wright, Second Edition, London (1988); which is incorporated in full by reference herein.

Compositions or compounds according to the invention, or for use according to the invention, can be provided alone or in combination with other compounds, for example they may be provided in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. For example, in the treatment of cancer compositions according to the invention may be administered in combination with one or more additional anti-cancer therapies. Examples of anti-cancer therapies include, without limitation, surgery, radiation therapy (radiotherapy), biotherapy, immunotherapy, chemotherapy, or a combination of these therapies. Chemotherapy may include the administration of one or more chemotherapeutic agents. The composition according to the invention and the one or more additional anti-cancer therapies, such as one or more chemotherapeutic agents, may be administered separately, sequentially or simultaneously.

The combined administration of a compound of Formula I or Ia or salt thereof and an additional anti-cancer therapy includes coadministration or concurrent administration, using separate formulations or a single pharmaceutical formulation, and consecutive administration in either order, wherein optionally there is a time period while both (or all) active agents simultaneously exert their biological activities "Pharmaceutically acceptable carrier, diluent or excipient" includes without limitation any adjuvant, carrier, excipient, glidant, sweetening agent, diluent, preservative, dye/colorant, flavour enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

The compounds of the present invention may be administered in the form of pharmaceutically acceptable salts. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula 1 used in the form of a salt thereof, particularly where the salt form confers on the active ingredient improved pharmacokinetic properties as compared to the free form of the active ingredient or other previously disclosed salt form.

The term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention may be used to modify solubility or hydrolysis characteristics, or to produce a sustained release formulation. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethylamine, diethylamine, piperazine, tris(hydroxymethyl)aminomethane, and tetramethylammonium hydroxide.

Pharmaceutical formulations will typically include one or more carriers acceptable for the mode of administration of the preparation, be it by injection, inhalation, topical administration, lavage, enteral or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in Remington: the Science & Practice of Pharmacy by Alfonso Gennaro, 20th ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The compounds or pharmaceutical compositions according to the present invention may be administered by oral or non-oral, e.g., intramuscular, intraperitoneal, intravenous, intracisternal injection or infusion, subcutaneous injection, transdermal or transmucosal routes. In some embodiments, compounds or pharmaceutical compositions in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. The compounds may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaries. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention may be used to treat animals, including mice, rats, horses, cattle, sheep, dogs, cats, and monkeys. The compounds of the invention may also be effective for use in humans. The term "subject" is intended to refer to an animal, preferably a mammal, most preferably a human, who has been the object of treatment, observation or experiment. However, the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, a prophylactic dose is used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1M, 0.1 nM-0.05M, 0.05 nM-15 µM or 0.01 nM-10M.

The term 'antiproliferative agents' is intended to mean a pharmacological agent that blocks cellular, parasitic or viral growth.

The term 'adjuvant' is intended to mean a pharmacological agent that would be added to, or administered with or alongside, a drug or therapeutic agent to enhance or aid the effect of the drug or therapeutic agent.

The skilled person will appreciate that all preferred or optional features of the invention may be applied to all aspects of the invention.

The references described herein are incorporated by reference.

BRIEF DESCRIPTION OF THE FIGURES

Embodiments of the present invention will now be described, purely by way of example, with reference to the accompanying drawings, in which:

FIG. 5—shows that a compound of Formula II (the active) selectively inhibits the translation of genes known to exacerbate the symptoms of autistic spectrum disorders. Experiments conducted using a published luciferase reporter system (Gkogkas et al Nature 2013, 493:371-7) demonstrate that treatment with Formula II selectively reduces the translation of the longer more structured 5' untranslated region (reporter 1) of the gene neuroligin 1 relative to neuroligin 2. Selective inhibition of neuroligin 1 protein levels has been demonstrated to restore the normal excitation/inhibition ratio and rectifies the social behaviour deficits observed in an autism mouse model (see Gkogkas et al, Nature 2013, 493:371-7). The mechanism of action and level of activity of Formula II are consistent with and comparative to a proven translational inhibitor extracted from a rare coral species (Hippuristanol—a proven inhibitor of eIf4A). In this experiment 1 µM of Hippuristanol and 1.3 µM of Formula I was used FIG. 6—shows that treatment with a compound of Formula II (active) inhibits the growth of the chemoresistant cancer cell line A549, lung carcinoma. Cells were treated with a range of doses of active for either 48 or 96 hrs. Each data point is representaive of at least 4 biological repetitions. Data is reproducable with different cultures of A549 cells, in two different laboratories at Nottingham (a) Biosciences and (b) Cancer Biology and efficacy has been demonstrated using standard techniques e.g. WST-1 (a) and MTT (b) and stably transfected luciferase cells (not shown).

FIG. 10—Compound 46, NLGN Translation reporter assay. FIG. 10 shows that a compound of Formula 46 selectively inhibits the translation of genes known to exacerbate the symptoms of autistic spectrum disorders. Experiments conducted using a published luciferase reporter system (Gkogkas et al 2013. Nature, 493:371-7) demonstrate that treatment with Formula II selectively reduces the translation of construct containing the 5' untranslated region (reporter 1) of the gene neuroligin 1 relative to neuroligin 2. Selective inhibition of neuroligin 1 protein levels has been demonstrated to restore the normal excitation/inhibition ratio and rectifies the social behaviour deficits observed in an autism mouse model (see Gkogkas et al, 2013. Nature, 493:371-7). FIG. 10B shows that inhibition of translation at this dose for this length of time is independent of the anti-proliferative activity of the molecule.

FIG. 11 shows that treatment of chemo-resistant A549 lung carcinoma cells with either a synthetic molecule of Formula II or the known inhibitor of eIF4A are both anti-proliferative. When used in combination, the sensitizing effects to very low level doses of Cisplatin (2 µM) of the synthetic molecule of Formula II is equivalent to hippuristanol. The ratio between anti-proliferative activity to chemo sensitizing activity is also equivalent.

FIG. 15—shows structures of compounds 46, 99 and 123.

FIG. 16—shows that treatment with a range of synthetic derivatives of the compound of Formula I and Ia has antiproliferative and chemosensitizing sensitizes effects which are linked to structure. Cells were treated with a range of different derivatives at three different doses (20 µM, 40 µM, 80 µM) of active. To determine sensitizing effects, additional experiments were also conducted in combination with 2 µM Cisplatin™ for 96 hrs. Each data point is representative of at least 4 biological repetitions and error=s.e.m).

FIG. 17—shows that treatment with a range of synthetic derivatives of the compound of Formula I and Ia has antiproliferative and chemosensitizing sensitizes effects which are linked to structure, and effects are additive or synergistic with Cisplatin™. Cells were treated with a range of different derivatives at three different doses (20 µM, 40 µM, 80 µM) of active. To determine sensitizing effects, additional experiments were also conducted in combination with 2 µM Cisplatin™ for 96 hrs. Each data point is representative of at least 4 biological repetitions and error=s.e.m).

EXAMPLES

A Compound of Formula I Inhibits Protein Synthesis
Polysome Profiling

Figure 1:
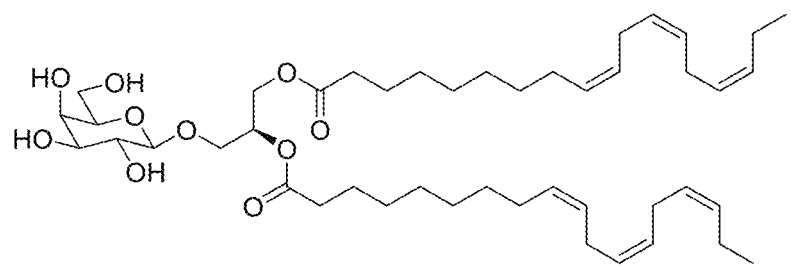
FIG. 1—illustrates the specific chemical structure of a compound of Formula II which is an example of compound of Formula I and Ia.
Figure 2:
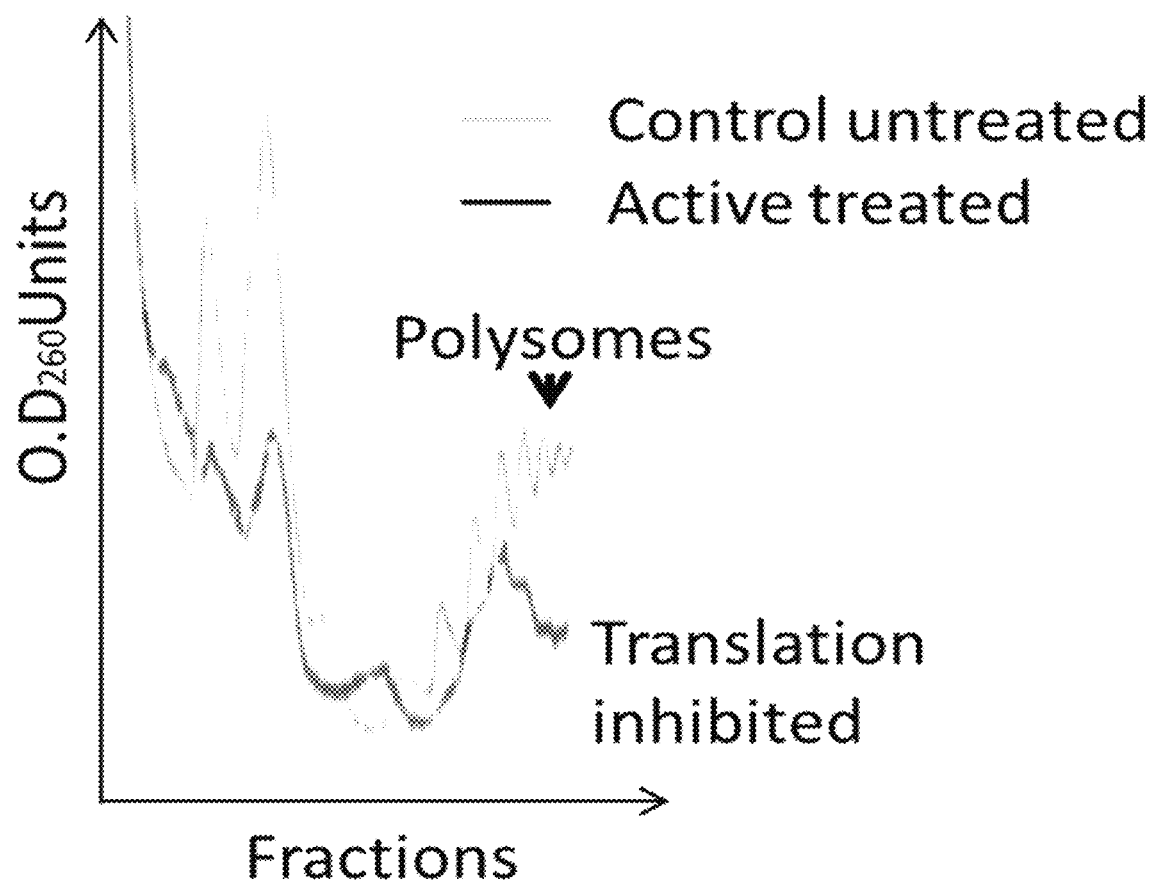
FIG. 2—demonstrates that a compound of Formula II inhibits translation and protein synthesis. Established techniques such as polysome profiling were used to show a reduction in the number of polyribosomes in neuroblastoma cells after treatment with a compound of Formula II. Polysome peaks from left to right show increasing number of ribosomes associated with mRNA. This peaks at 3 ribosomes after treatment with a compound of Formula II showing rapid and reproducible perturbation of translation. Cells were treated for 20 minutes with a compound of Formula II then harvested and prepared as described in materials and methods. The supernatants were loaded onto 10-50% sucrose gradients and spun for 2 hrs at 38,000 RPM. Gradients were visualised using a UV detector. A reduction in the amount of polyribosomes is observed after treatment with a compound of Formula II.

By using polysome ribosome profiling a compound of Formula I, as exemplified in these experiments by the compound of Formula II (FIG. 1), is demonstrated to be an inhibitor of protein synthesis as shown by profiling of the number of ribosomes associated with mRNA in the presence and absence of the compound (FIG. 2). Standard sucrose density polysome profiling techniques demonstrate that treatment with a compound of Formula II reduces the average numbers of ribosomes per message in cultured human cells. The number of ribosomes is indicative of the translation of an mRNA and synthesis of the protein encoded by the mRNA, and treatment with the compound of Formula II decreases the number of ribosomes per message thereby reducing global protein synthesis.

Use of the Compound(s) for the Inhibition of eIF4A

By using a well characterised luciferase based reporter assay it was further determined that this class of molecule functions as a protein synthesis inhibitor via targeting the helicase eIF4A. The cricket paralysis virus RNA contains a well-documented internal ribosomal entry site (CrPV IRES); this internal ribosomal entry site does not require eIF4A for active translation (Bordeleau et al, 2006 Nature Chemical Biology, 2: 213-220). Cap-dependent (eIF4A dependant) translation (firefly luciferase signal), but not CrPV IRES-dependent translation (Renilla luciferase signal), was inhibited after 3 hours treatment with the Synthetic version of the natural molecule. Since the lack of a requirement for eIF4A for CrPV translation is well documented (e.g. Bordeleau et al, 2006 Nature Chemical Biology, 2: 213-220) this data further demonstrates inhibition is selective and provides evidence that the target is the translation initiation factor eIF4A.

Reporter Assays

Figure 3A:
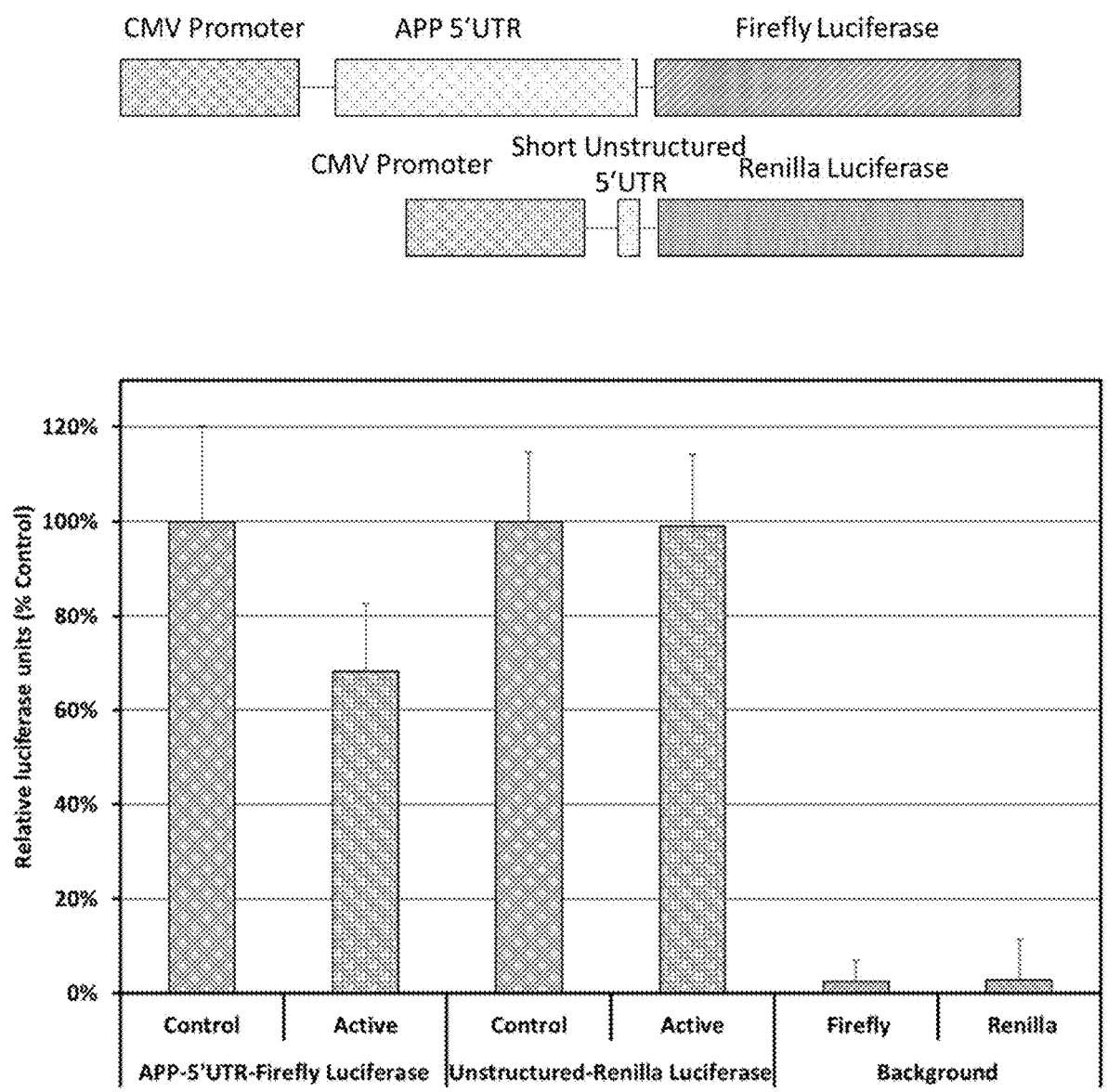
FIG. 3a—shows that treatment of SH-SY5Y cells with a compound of Formula II (referred to as "active") results in the selective inhibition of amyloid precursor protein APP 5'UTR luciferase reporter relative to a Renilla luciferase reporter construct containing a short unstructured 5'UTR. SH-SY5Y cells were simultaneously co-transfected with APP-5'UTR firefly luciferase construct and a Renilla control vector. Luciferase levels were assayed using a Glomax Luminometer and Stop-n-Glo luciferase reagents (standard procedure throughout). The data presented represents 8 biological repetitions and use as the active a semi refined compound of Formula II. Levels of compound were estimated based on amounts of purified compound obtained from fresh tomato tissue.

Reporter assays were used to demonstrate that the compound of Formula II is an inhibitor of protein synthesis. Firefly/renilla luciferase reporter experiments conducted using cultured human cell lines show that the compound of Formula II is a selective and facile inhibitor of protein synthesis (schematics of the reporter constructs are included in FIGS. 3a, 3d and 5). The compound of Formula II is shown to selectively decrease the levels of a reporter construct containing a long structured 5'UTR upstream of a firefly luciferase gene, but to have little effect on a co-transfected *renilla* luciferase reporter construct containing a short unstructured 5'UTR (FIGS. 3a and 5).

Figure 3B:
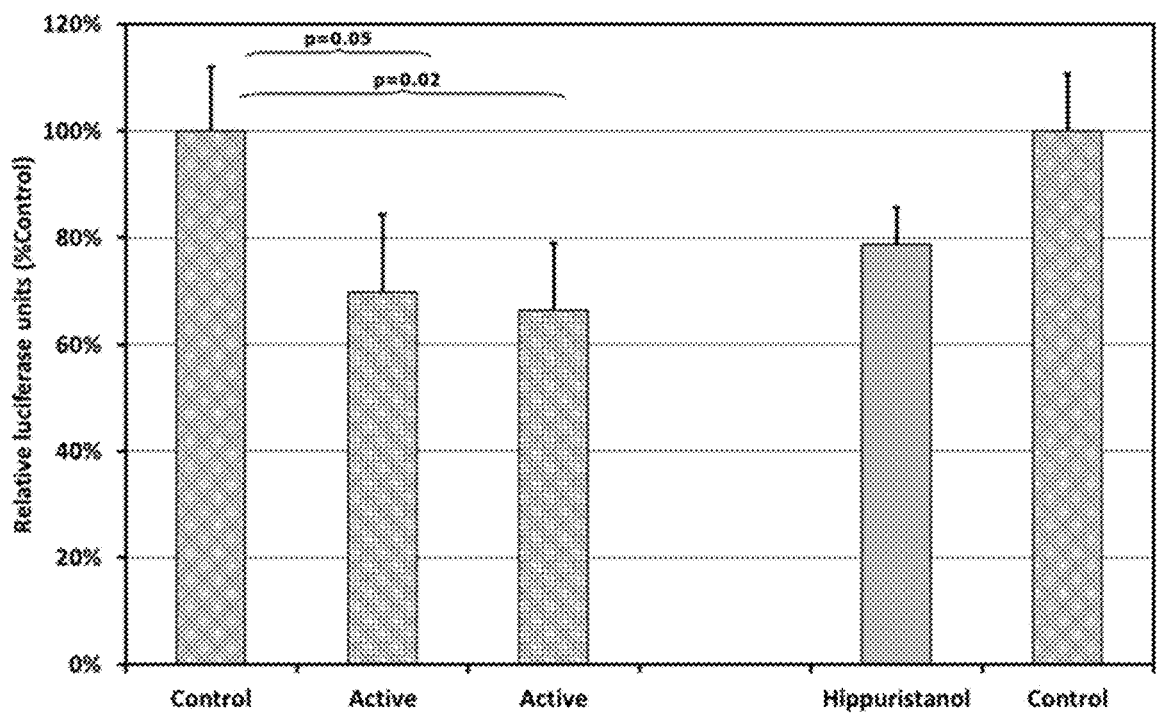
FIG. 3b—shows the result of experiments in which neuroblastoma cells were transfected with a firefly luciferase translation reporter 24 hours before treatment—cells were then treated for 4 hrs with either a compound of Formula II (active) or 1 µM Hippuristanol. Graphs represent 4 biological repetitions per treatment—2 independent treatments of a compound of Formula II. Inhibition of translation reporter activity by a compound of Formula II is equivalent to treatment with 1 µM Hippuristanol (proven inhibitor of eIf4A) alone for both experiments.
Figure 3C:
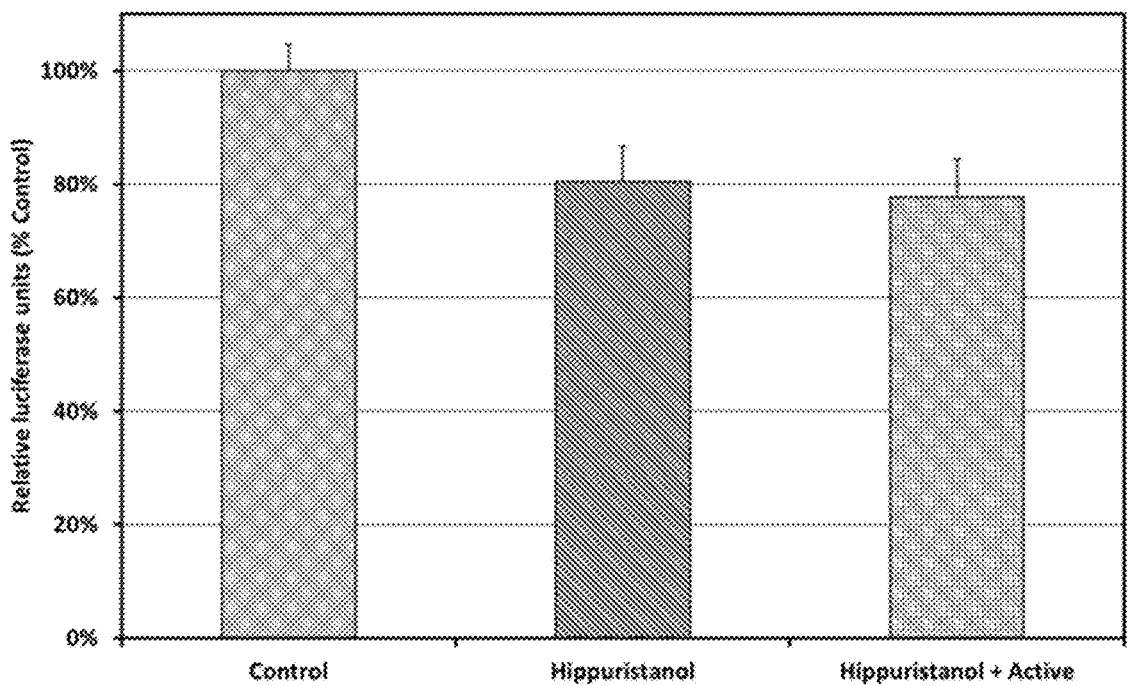
FIG. 3c—shows the results of experiments in which cells were transfected with a firefly luciferase translation reporter 24 hours before treatment—cells were then treated for 4 hrs with Hippuristanol (1 µM) or Hippuristanol plus a compound of Formula II (active). Graphs represent 4 biological repetitions per treatment. Hippuristanol and Hippuristanol plus a compound of Formula II result in significant inhibition (p=0.01 and 0.009 respectively). No difference is observed between Hippuristanol and Hippuristanol plus a compound of Formula II.

The degree of translation inhibition is shown to be equivalent to that of a known inhibitor of translation, hippuristanol (FIGS. 3b and 5). Comparative structured 5'UTR firefly luciferase reporter experiments conducted using either hippuristanol or a compound of Formula II show the inhibition of reporter levels is equivalent. Co-treatment with a compound of Formula II and hippuristanol (FIG. 3c) shows no additive inhibitor effects providing further evidence that both molecules are acting on the same target, this may be the translation complex helicase protein eIF4A.

Figure 3D:
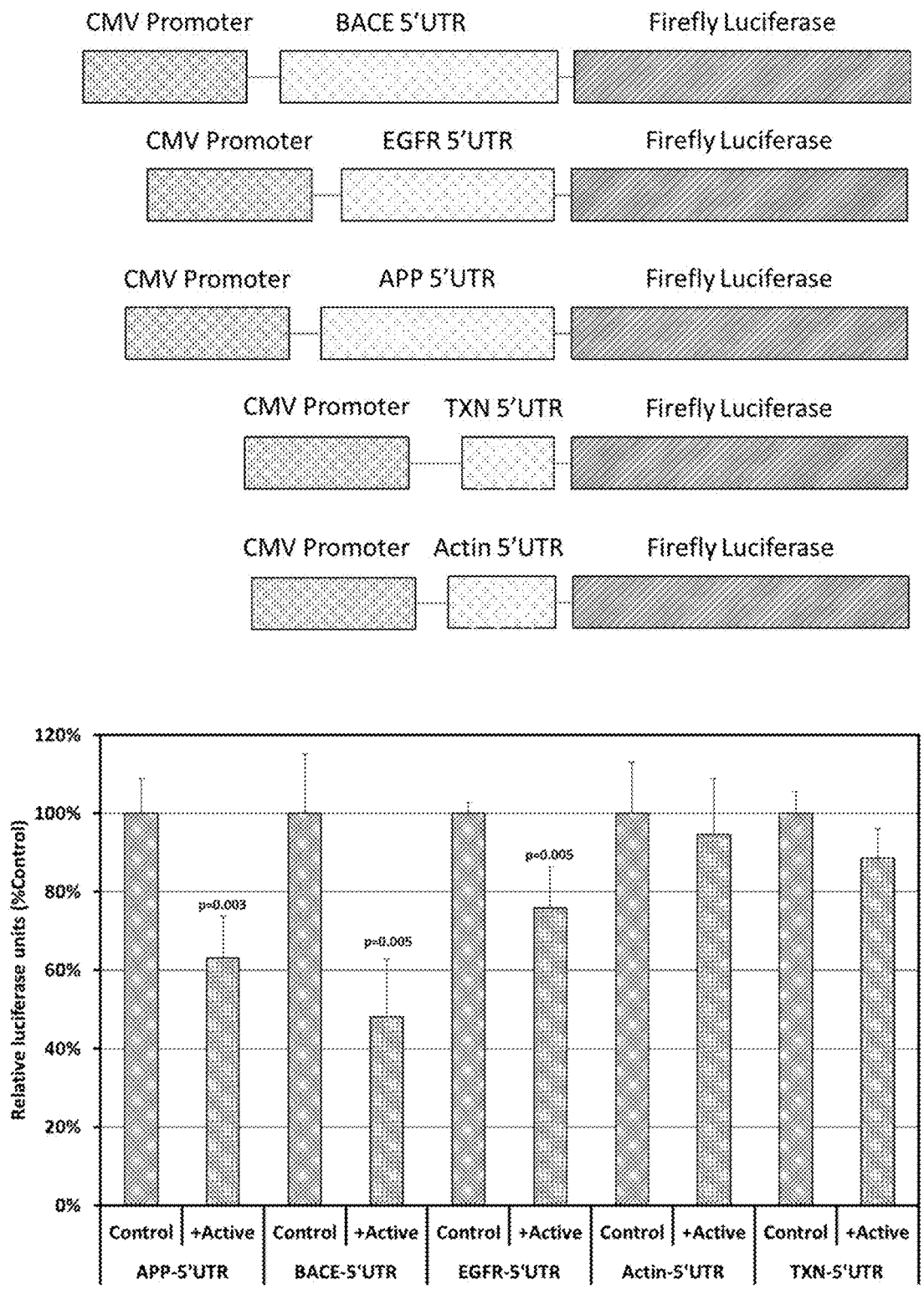
FIG. 3d—shows that treatment with a compound of Formula II (referred to as "active") selectively reduces the levels of firefly luciferase reporter activity dependant on 5'UTR sequence. The 5'UTRs of genes which negatively associate with the progression of Alzheimer's disease—amyloid precursor protein (APP) and beta secretases (BACE) are all inhibited by treatment with a compound of Formula II, whereas the equivalent reporter levels of housekeeping genes actin and thioredoxin (TXN) are not inhibited. The 5'UTR of cancer associated epidermal growth factor receptor (EGFR) is also selectively inhibited by treatment with a compound of Formula II. Neuroblastoma cells were transfected 24 hours prior to treatment with a compound of Formula II. After treatment, cells were prepared as described in the materials and methods. Each experiment represents between 6 and 8 biological repetitions.

Firefly luciferase reporter experiments conducted with the 5'UTRs of genes which negatively associate with disease demonstrate that inhibition is both selective and relevant to the treatment of disease such as Alzheimer's disease, cancer and autistic spectrum disorders by selectively altering the translation of select transcripts while the translation of housekeeping or cytoprotective genes remains unaffected (FIGS. 3d and 5). After treatment with the compound of Formula II the levels of translation of a reporter construct containing the 5'UTR of amyloid precursor protein, which is processed into toxic amyloid the major constituent of amyloid plaques in Alzheimer's disease, is inhibited relative to equivalent control treatments. Similar significant inhibition ($p=0.005$) of a construct containing the 5'UTR of the epidermal growth factor receptor gene (EGFR), a gene whose expression and levels of proteins negatively associate with cancer progression and survival is also observed after treatment. This data also supports the model of selective inhibition.

The data also supports the use of compounds of Formula I for the treatment of diseases such as Alzheimer's disease, cancer and autistic spectrum disorders.

Use of a Compound of Formula I in the Treatment of Cancer

Figure 4A:
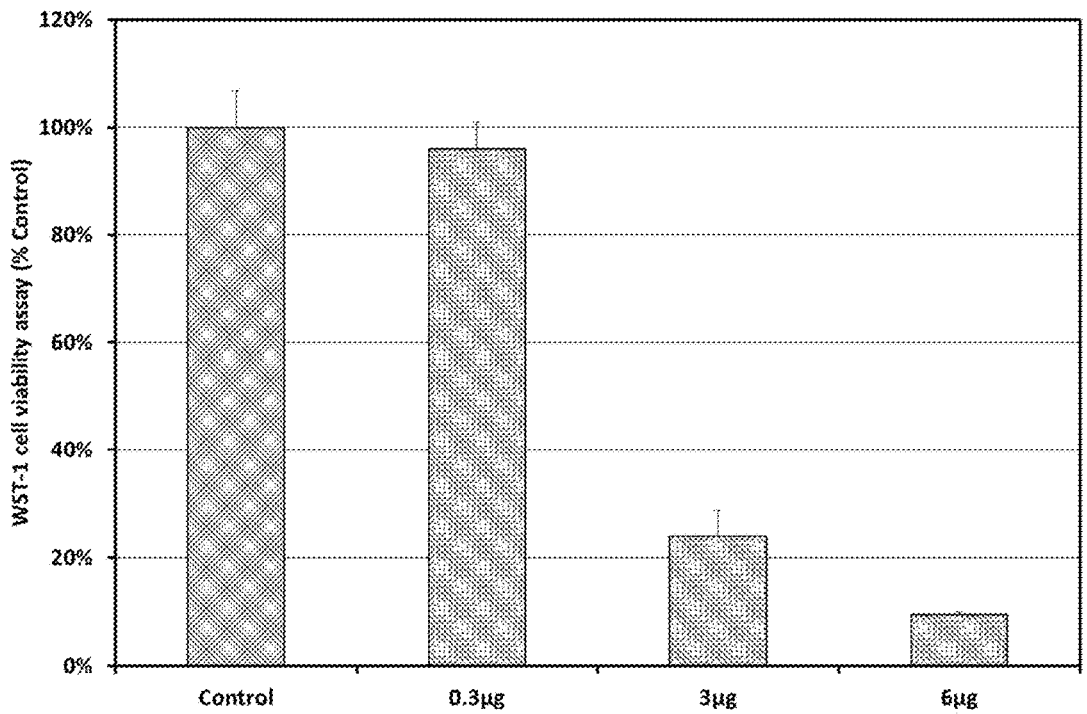
FIG. 4a—shows the results of experiments in which fast growing breast cancer cells MCF7 were treated for 96 hours with a compound of Formula II only. Growth of MCF7 cell lines were slowed by the treatment with a compound of Formula II. Experiment represents 6 biological repetitions, Error=S.E.M.
Figure 4B:
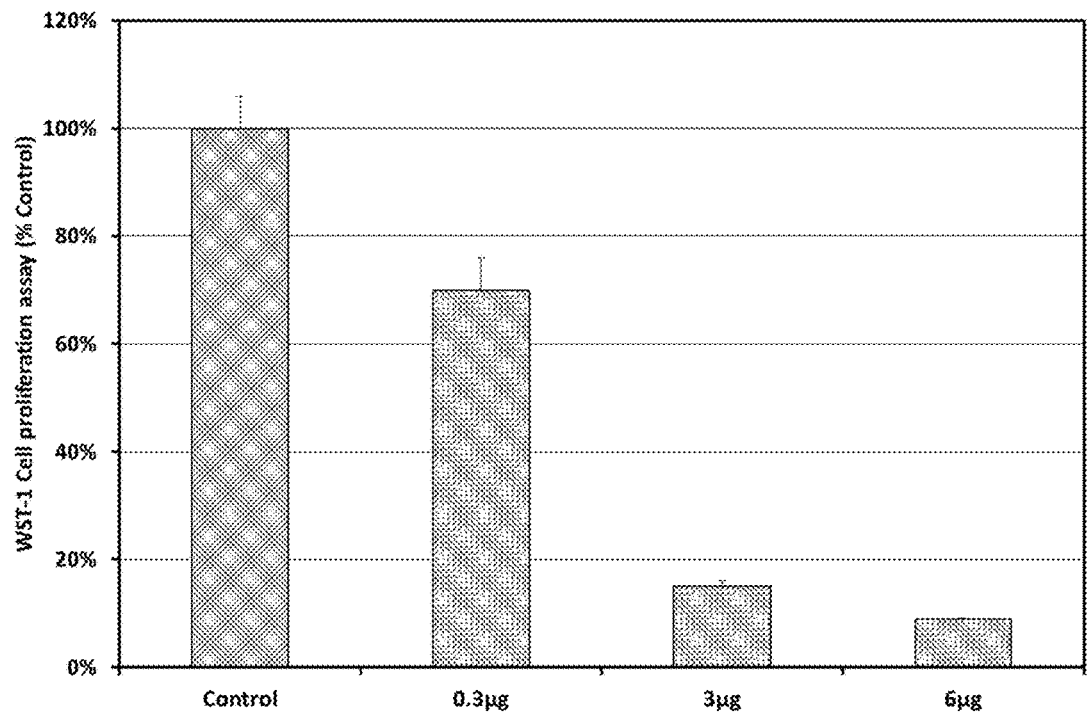
FIG. 4b—shows the results of experiments in which fast growing breast cancer cells MDA-MB-231 were treated for 96 hours with a compound of Formula II only. Growth of MDA-MB-231 cell lines were slowed by the treatment with a compound of Formula II. Experiment represents 6 biological repetitions, Error=S.E.M.
Figure 4C:
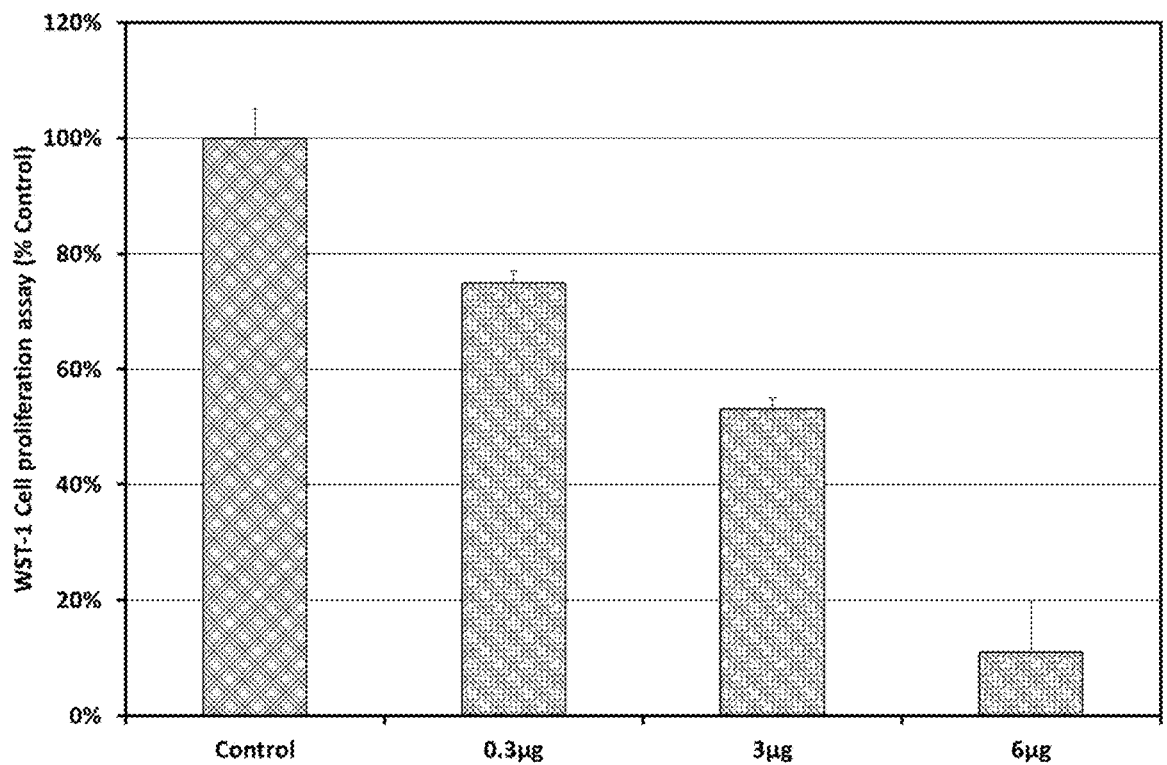
FIG. 4c—shows the results of experiments in which slow growing SKOV3 ovarian cancer cells were treated for 96 hours with a compound of Formula II only. Growth of SKOV3 cell lines were slowed by the treatment with a compound of Formula II at higher doses. Experiment represents 6 biological repetitions, Error=S.E.M.
Figure 4D:
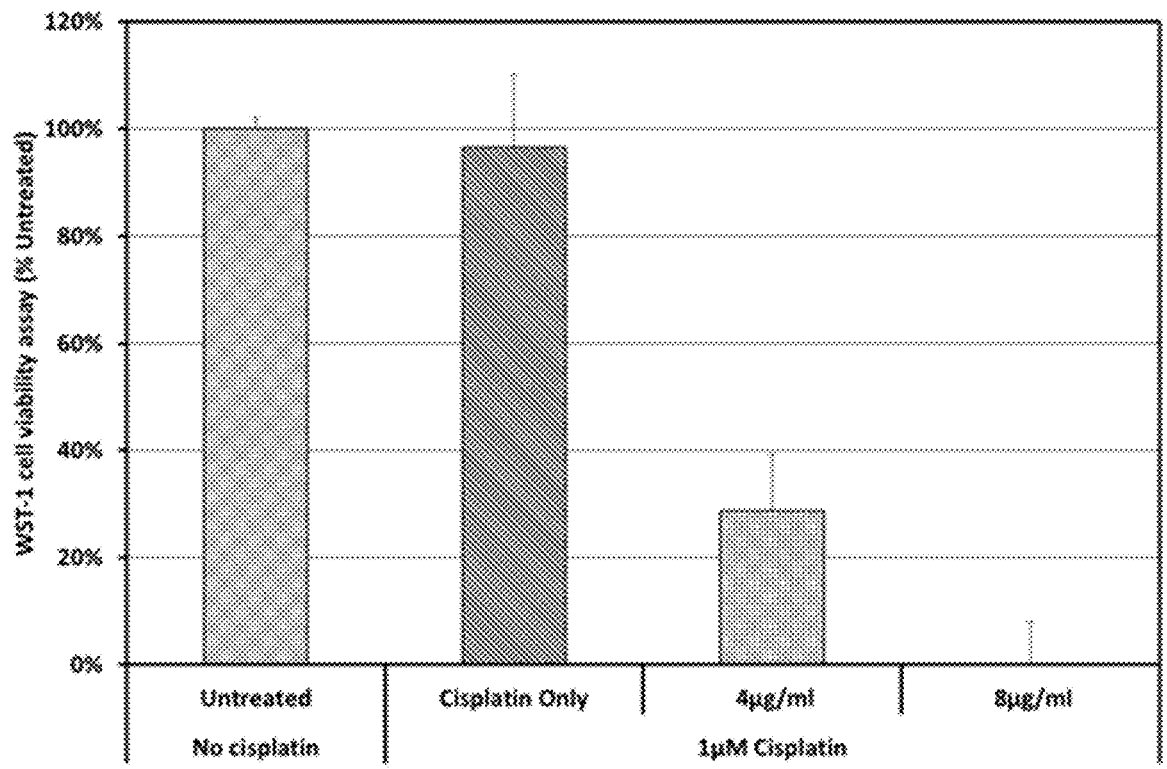
FIG. 4d—shows the results of experiments in which slow growing A549 lung carcinoma cancer cells were treated for 96 hours with a compound of Formula II plus a very low dose Cisplatin™ (1 µM). Cisplatin™ resistant A549 lung cancer cells were sensitised to treatment with a compound of Formula II in combination with 1 µM Cisplatin™—a complete kill is achieved at higher doses of a compound of Formula II.
Figure 4E:
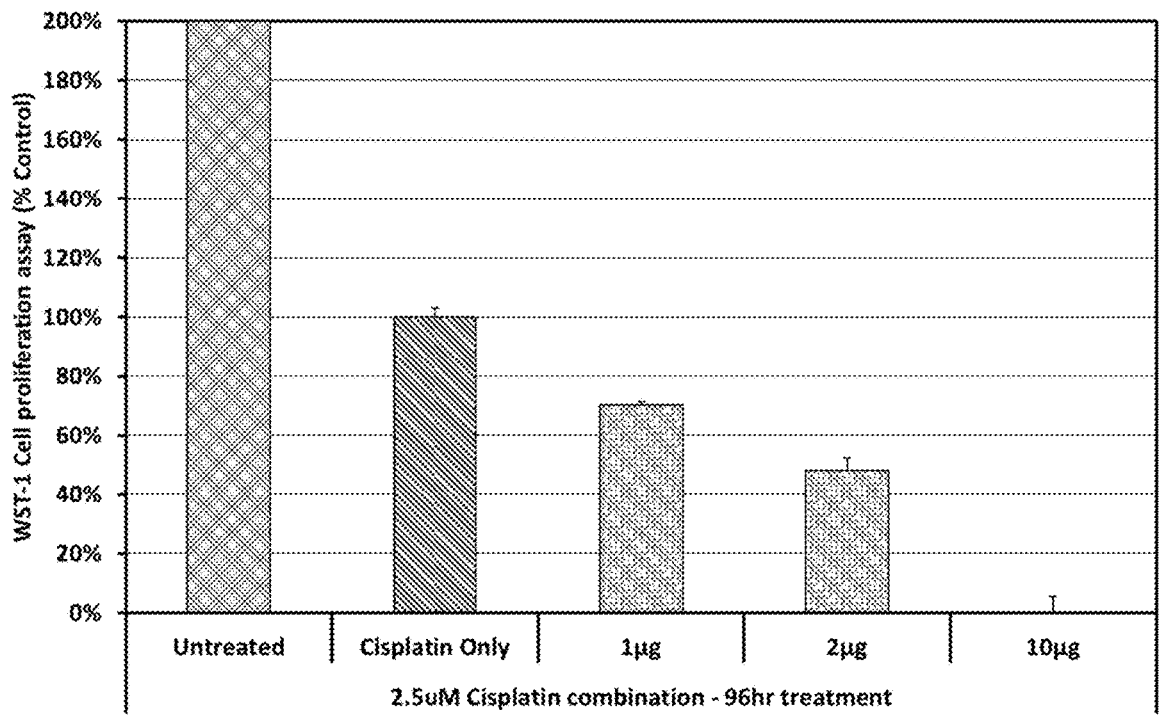
FIG. 4e—shows the results of experiments in which slow growing SH-SY5Y neuroblastoma cancer cells were treated for 96 hours with a compound of Formula II plus low dose Cisplatin™. Cisplatin™ resistant A549 lung cancer cells were sensitised to treatment with a compound of Formula II in combination with 2.5 µM Cisplatin™—a complete kill is achieved at higher doses (10 µg) of a compound of Formula II.
Figure 4F:
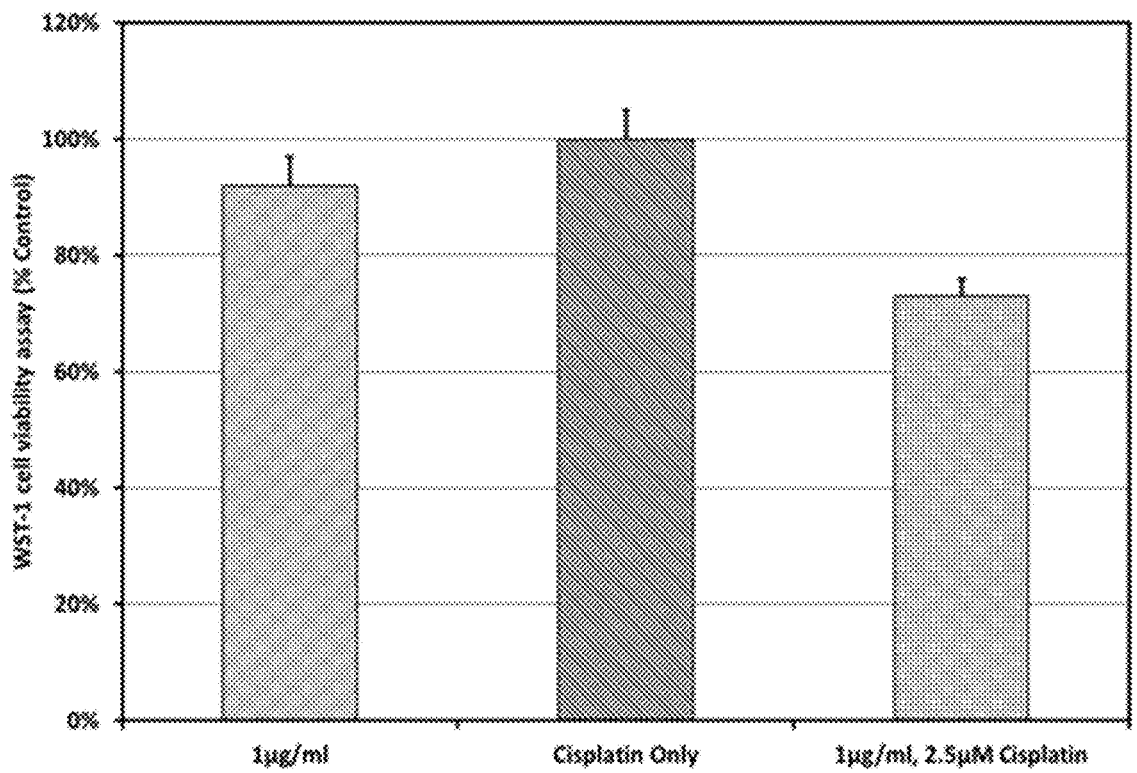
FIG. 4f—shows the results of experiments in which slow growing SKOV-3 ovarian cancer cells were treated for 96 hours with a compound of Formula II plus low dose Cisplatin™. Cisplatin™ resistant SKOV-3 ovarian cancer cells were sensitised to treatment with a compound of Formula II in combination with 2.5 µM Cisplatin™ (p=0.003) (right hand bar in the figure), no effect is observed from treatment with equivalent levels of a compound of Formula II alone (left hand bar in the figure) or Cisplatin™ alone.

A compound of Formula I or Ia, as exemplified by the compound of Formula II, may be used alone in the treatment of cancer as demonstrated by its ability to act as an anti-proliferative agent when used as a treatment in isolation (FIGS. 4a, b, c, 5 and 6). As cancer cells recruit the protein synthesis machinery to drive proliferation, this presents an attractive target for therapy. It is well established that rapidly growing tumour cell lines require relatively higher levels of protein synthesis than normal cells—treatment of rapidly proliferating breast cancer cell lines (MCF-7 and MDA-MD-231) with the compound of Formula II dramatically limits the proliferation of these cell types (FIG. 4a, 4b). Equivalent treatments of slow growing cell lines e.g. SKOV3 ovarian cancer cells using a compound of Formula II (FIG. 4c) shows some slowing of proliferation.

Figure 6:
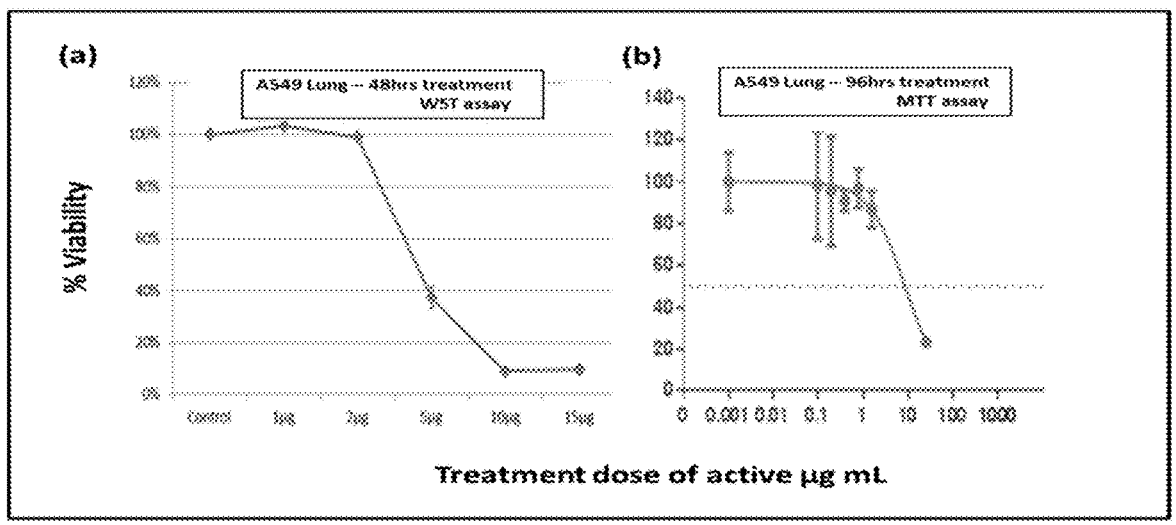
Figure 7:
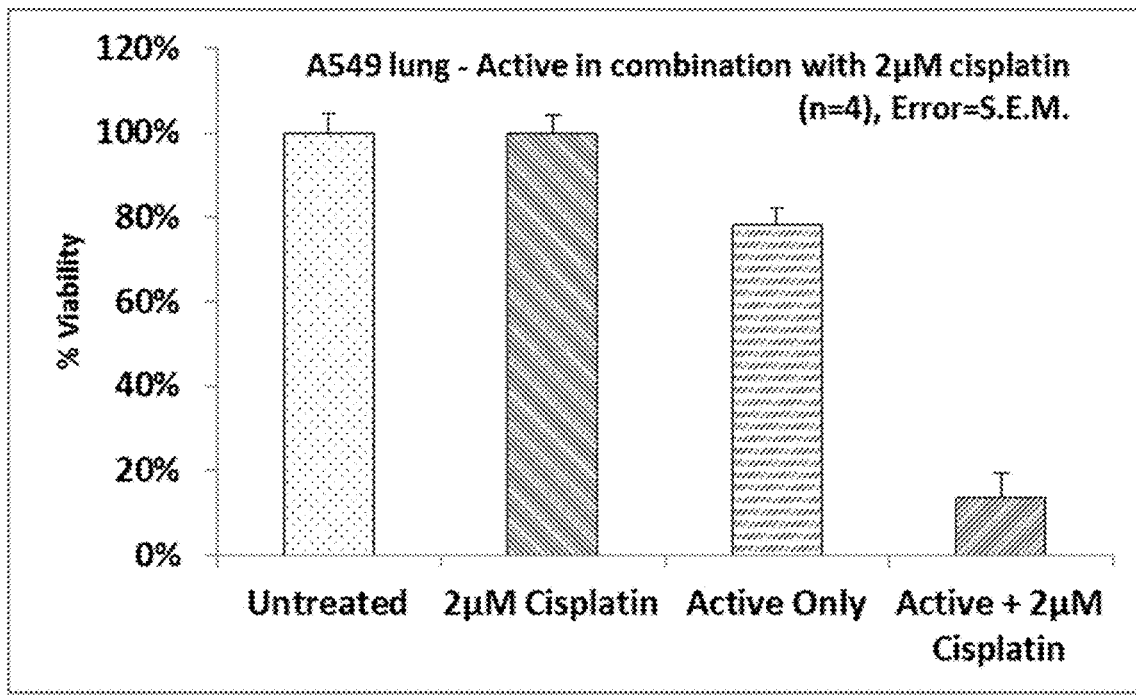
FIG. 7—shows that treatment with a low dose of a compound of Formula II (active) sensitises chemo-resistant A549 lung carcinoma cells to very low levels of Cisplatin (2 µM). Cells were treated with either 2 µM Cisplatin™ alone, c. 1 µg active alone or c. 1 µg active in combination with 2 µM Cisplatin™. A WST-1 cell proliferation assay was performed 96 hrs after treatment. Experiment represents 4 independent biological repetitions. A significant increase in the efficacy of Cisplatin™ is observed when treated in combination with the compound of Formula II.
Figure 9A:
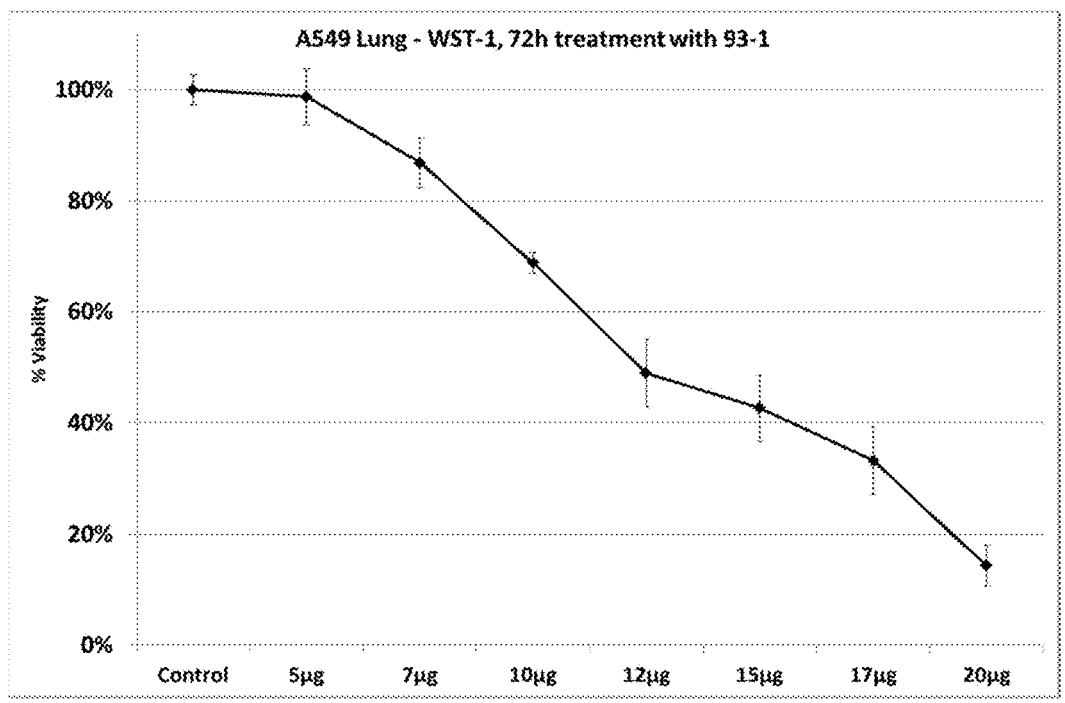
FIG. 9a—shows the effect of the treatment of A549 lung carcinoma cells with a synthetic molecule of Formula II. The data shown demonstrates that cell growth is inhibited by Formula II in a dose dependent manner. A WST-1 cell proliferation assay was performed 72 hrs after treatment. Experiment represents 4 independent biological repetitions.

Similar results are seen with A549 lung cancer cells (FIG. 6 and FIG. 9a). Similar results were seen with the compound of Formula II when purified from a natural source (FIG. 6) and with a chemically synthesised compound of Formula II (FIG. 9a).

A compound of Formula I or Ia, as exemplified by the compound of Formula II, may also be used in combination with other chemotherapeutic agents for the treatment of cancer. The compound of Formula I or Ia may sensitise cells to the chemotherapeutic agents thereby reducing the dose of chemotherapeutic agent needed. This is particularly advantageous as chemotherapeutic agents can be toxic and particularly difficult for patients to tolerate. The side effects of chemotherapeutic agents at the doses currently required are in some cases so severe that the use of potentially effective drugs is precluded.

Figure 8:
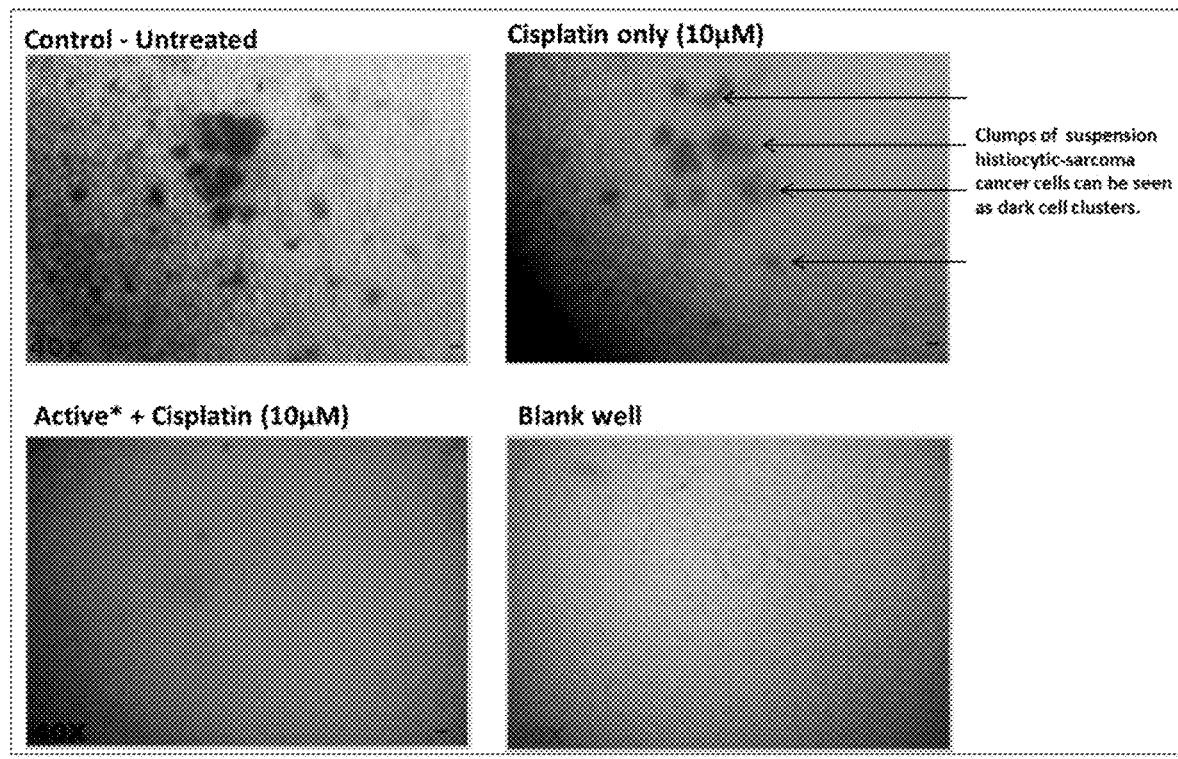
FIG. 8—shows the effect of a compound of Formula II (which is exemplary of Formula I and Ia) on chemo-resistant primary canine histocytic sarcoma tumour cells biopsied from a 7 yr old retriever. Cells were cultured for 6 days with a single dose treatment of Cisplatin™ (10 µM) or a combination of Cisplatin™ plus a compound of Formula II (active). Images were taken after 6 days treatment and are representative of three independently treated wells. Each image (40× magnification) represents the majority of the well area and is of an equivalent area in each photograph. Similar results were observed with the active in combination with carboplatin (2 µM dose).

Known inhibitors of protein synthesis such as hippuristanol have proven potent anti-cancer properties when used in combination with chemotherapeutic agents such as Cisplatin™ or Doxorubicin™. However hippuristanol is naturally found in coral to is scarce and expensive to obtain, furthermore it is very difficult and expensive to synthesise. The data presented here demonstrates that a compound of Formula I or Ia, exemplified by the compound of Formula II, can be used as an adjuvant in combination with chemotherapeutic agents to enhance cell death. In particular this combination has a potent effect at slowing proliferation or killing cancer cells. Slow growing and difficult to treat tumour cell types such as A549 lung cancer cells, SH-SY5Y neuroblastoma or SKOV-3 cancer cells are all sensitised by exposure to Formula II to very low doses of Cisplatin™ (FIGS. 4d, 4e, 4f and 7)—a complete kill can be achieved in both A549 and SH-SY5Y cells after a single dose treatment with g quantities of a compound of Formula II in combination with 1 μM or 2.5 μM treatments of Cisplatin™. A similar effect is observed when rapidly growing tumour cell lines or primary tumour cells (FIG. 8) are treated with a compound of Formula II and chemotherapeutics such as Cisplatin™. In this example primary tumour cells were isolated from a dog and then in vitro exposed to the compound of Formula II and Cisplatin™. The results show that when treated with only Cisplatin™ many cancer cells remain, however when treated with Cisplatin™ and the compound of Formula II substantially all tumour cells were killed. Not visible in the images reproduced here but visible under the microscope, it can be seen that white blood cells which were transferred with the tissue sample were still alive after the Cisplatin™ and Formula II treatment. This demonstrates the adjuvant properties of a compound of Formula I, more specifically that compounds of Formula I can sensitise cancer cells to the effects of chemotherapeutic agents.

Figure 9B:
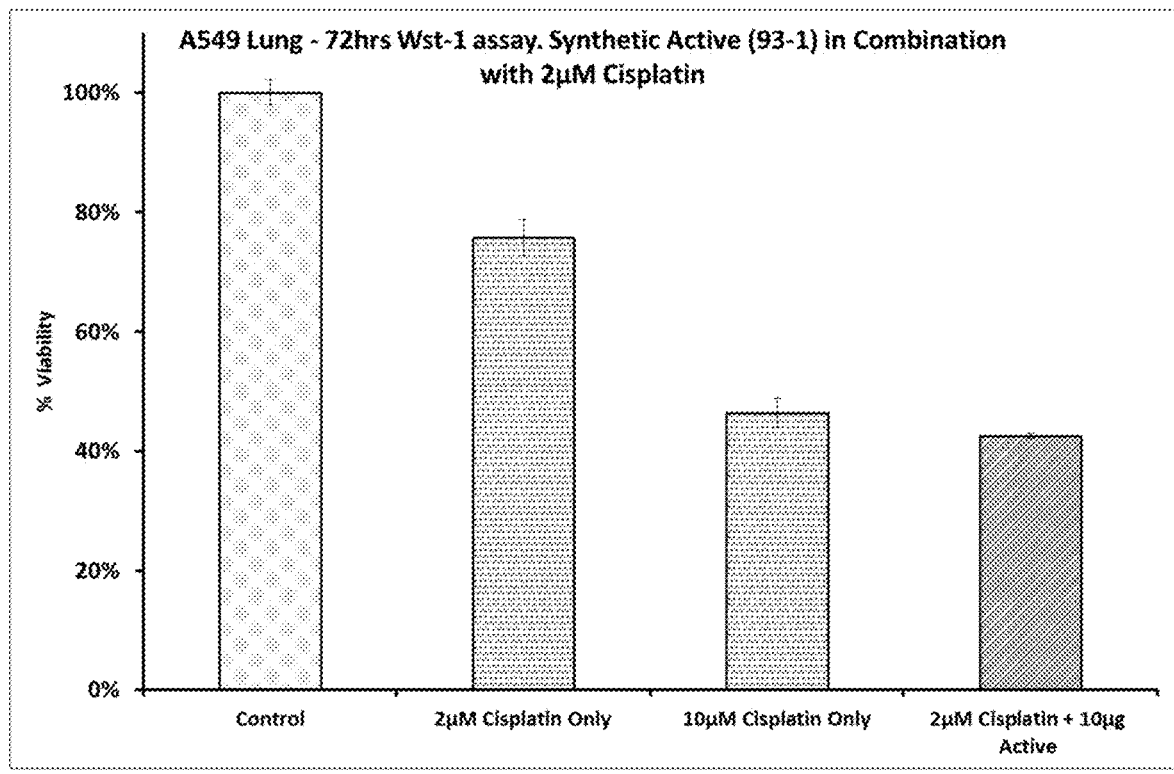
FIG. 9b—shows that treatment of chemo-resistant A549 lung carcinoma cells with a synthetic molecule of Formula II sensitises the cells to very low level doses of Cisplatin (2 µM). Cells were treated with either 2 µM or 10 µM Cisplatin™ alone, or 10 µg synthetic molecule Formula II in combination with 2 µM Cisplatin™. A WST-1 cell proliferation assay was performed 72 hrs after treatment. Experiment represents 4 independent biological repetitions. A 5-fold increase in the efficacy of Cisplatin™ is observed when treated in combination with the synthetic Formula II.

The results in FIG. 9b demonstrate that a chemically synthesised compound of Formula II is also effective as an anticancer agent alone, and as an agent to sensitise cancer cells to other chemotherapeutic agents. Previously discussed data was obtained used a compound of Formula II isolated from tomatoes.

Figure 11:
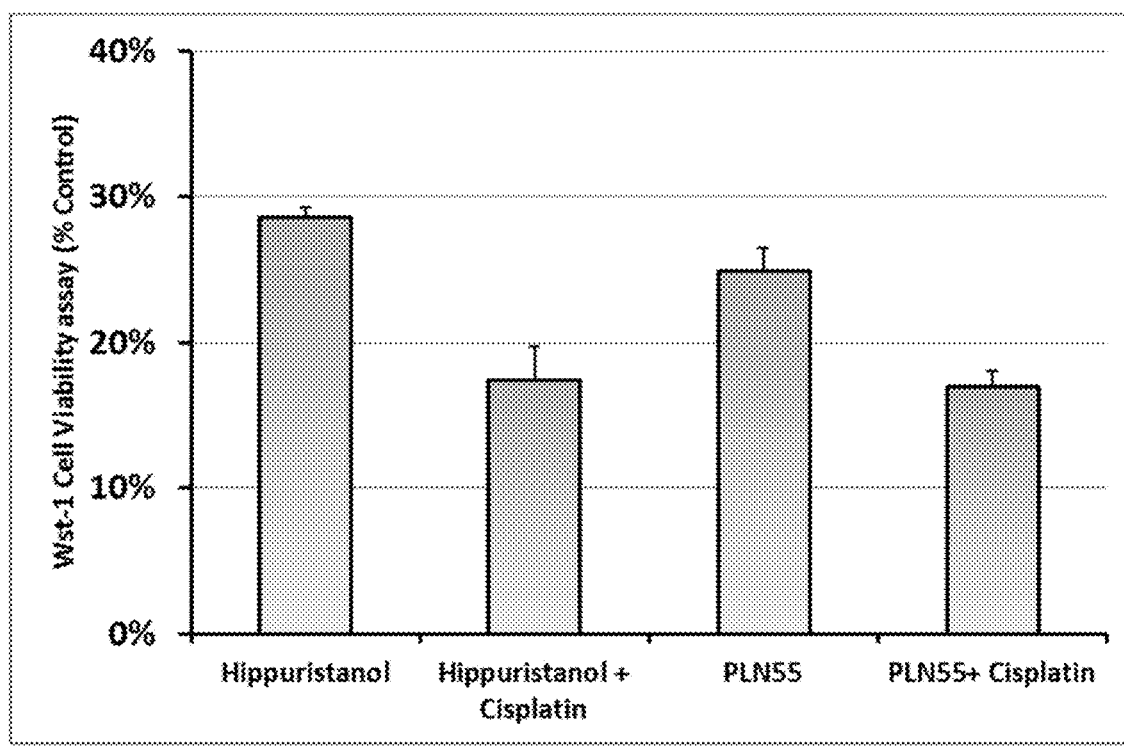
FIG. 11—Natural molecule plus cisplatin compared to Hippuristanol plus cisplatin.
Figure 12:
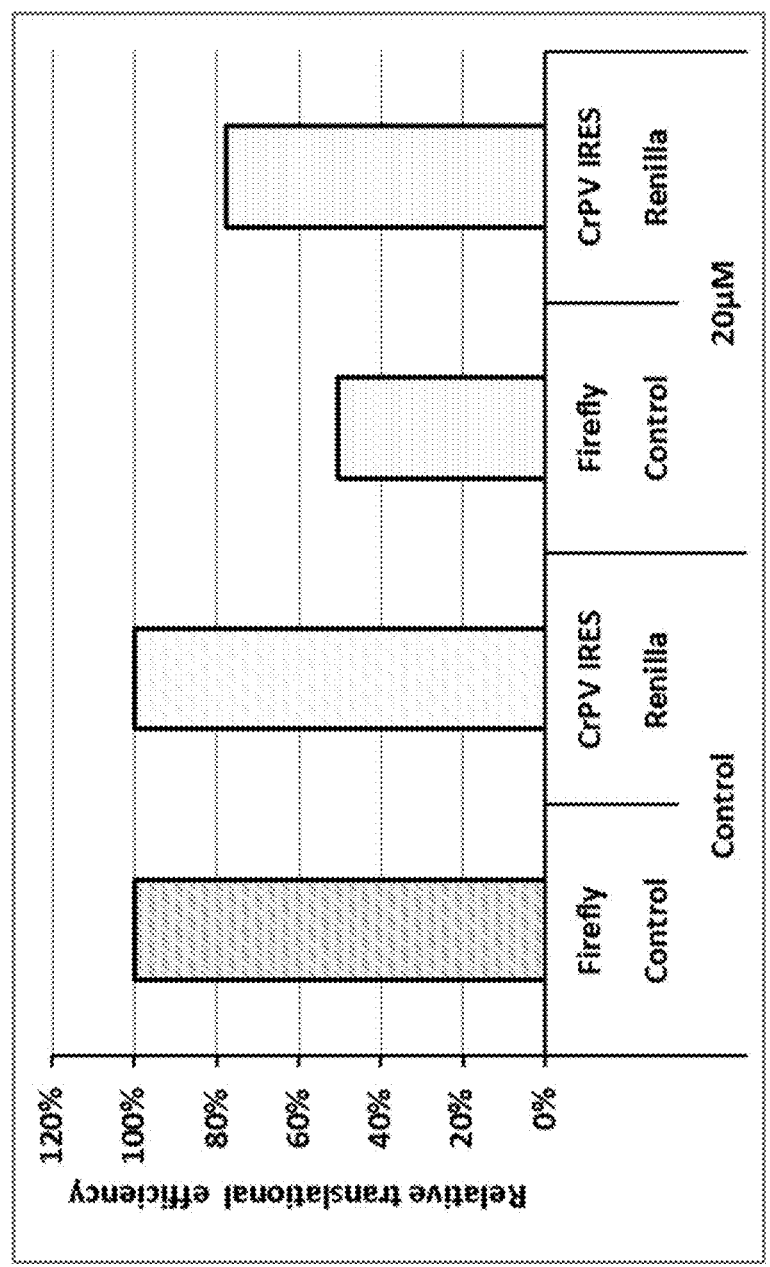
FIG. 12—CrPV assay—Natural molecule targets eIF4A. Treatment with 20 µM of the synthetic natural molecule selectively inhibits cap dependant translation. Treatment with Formula II selectively reduces the translation of the firefly luciferase gene relative to the renilla gene, which is downstream of the eIF4A independent CrPV IRES.

The results shown in FIG. 11 demonstrate that the relative anti-proliferative effects of treatment with a chemically synthesised compound of Formula II is comparable in efficacy to treatment with the known inhibitor hippuristanol. The relative activity as an agent to sensitise cells to cisplatin treatment is also equivalent at this dose.

Figure 9C:
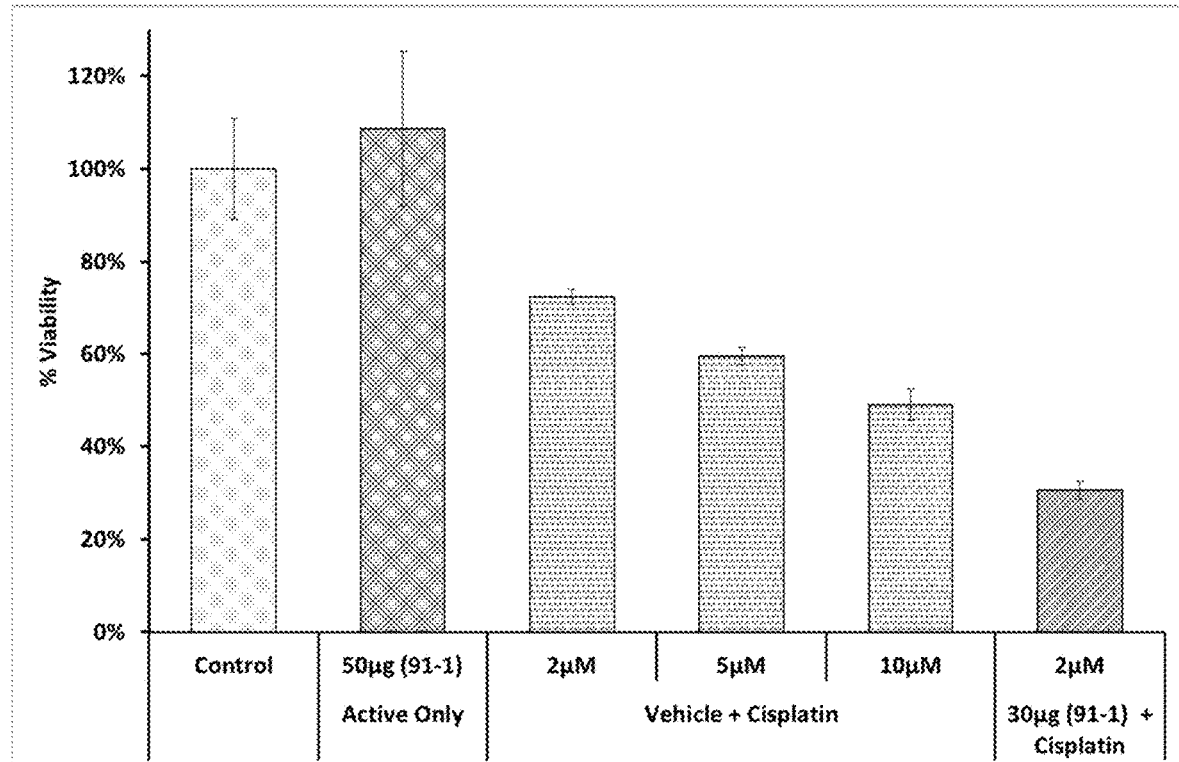
FIG. 9c—shows that treatment of chemo-resistant A549 lung carcinoma cells with a chemically synthesised acetyl derivative of Formula II sensitises the cells to very low level Cisplatin™ (2 µM). Cells were treated with either 2 µM, 5 µM or 10 µM Cisplatin™ alone, 50 µg synthetic acetyl derivative molecule or 30 µg in combination with 2 µM Cisplatin™. A WST-1 cell proliferation assay was performed 72 hrs after treatment. Experiment represents four independent biological repetitions. No effect was detected after treatment with 50 µg synthetic acetyl derivative, however an 8-fold increase in the efficacy of Cisplatin™ is observed when treated in combination with 30 µg synthetic acetyl derivative and 2 M Cisplatin™.

The results in FIG. 9c demonstrate that a chemically synthesised acetyl derivative of a compound of Formula II is also effective as an agent to sensitise cancer cells to other chemotherapeutic agents, in this particular example to Cisplatin™. The acetyl derivative of Formula II used in this study is illustrated below:

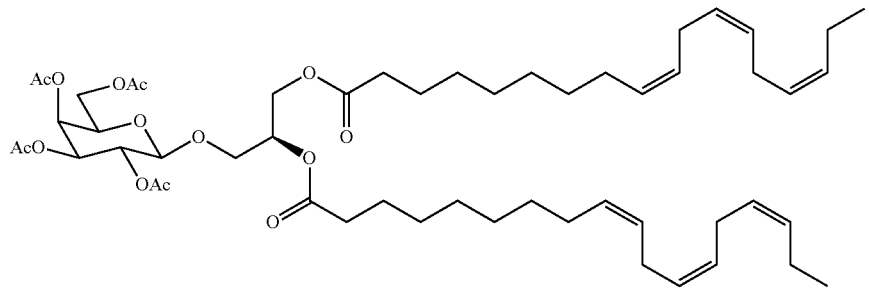

Chemical Formula: $C_{53}H_{82}O_{14}$ Molecular Weight: 943.23

Figure 13:
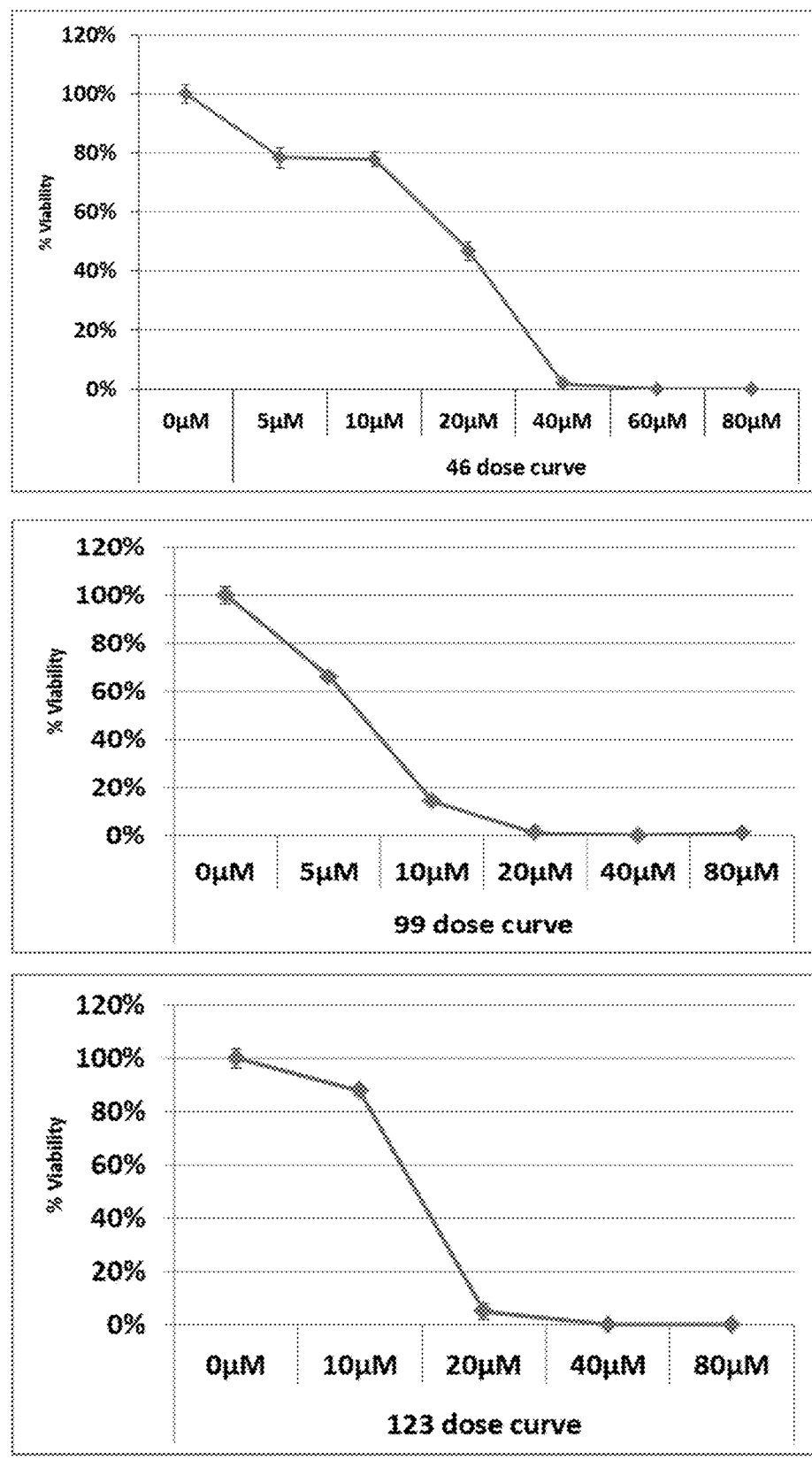
FIG. 13—Dose curves of compounds 46, 99 and 123. Shows that treatment with synthetic derivatives of the compound of Formula II (46, 99 and 123) inhibits the growth of the chemoresistant cancer cell line A549, lung carcinoma in a dose dependant manner. Cells were treated with a range of doses of active for 96 hrs. Each data point is representative of at least 4 biological repetitions and error=s.e.m).
Figure 14:
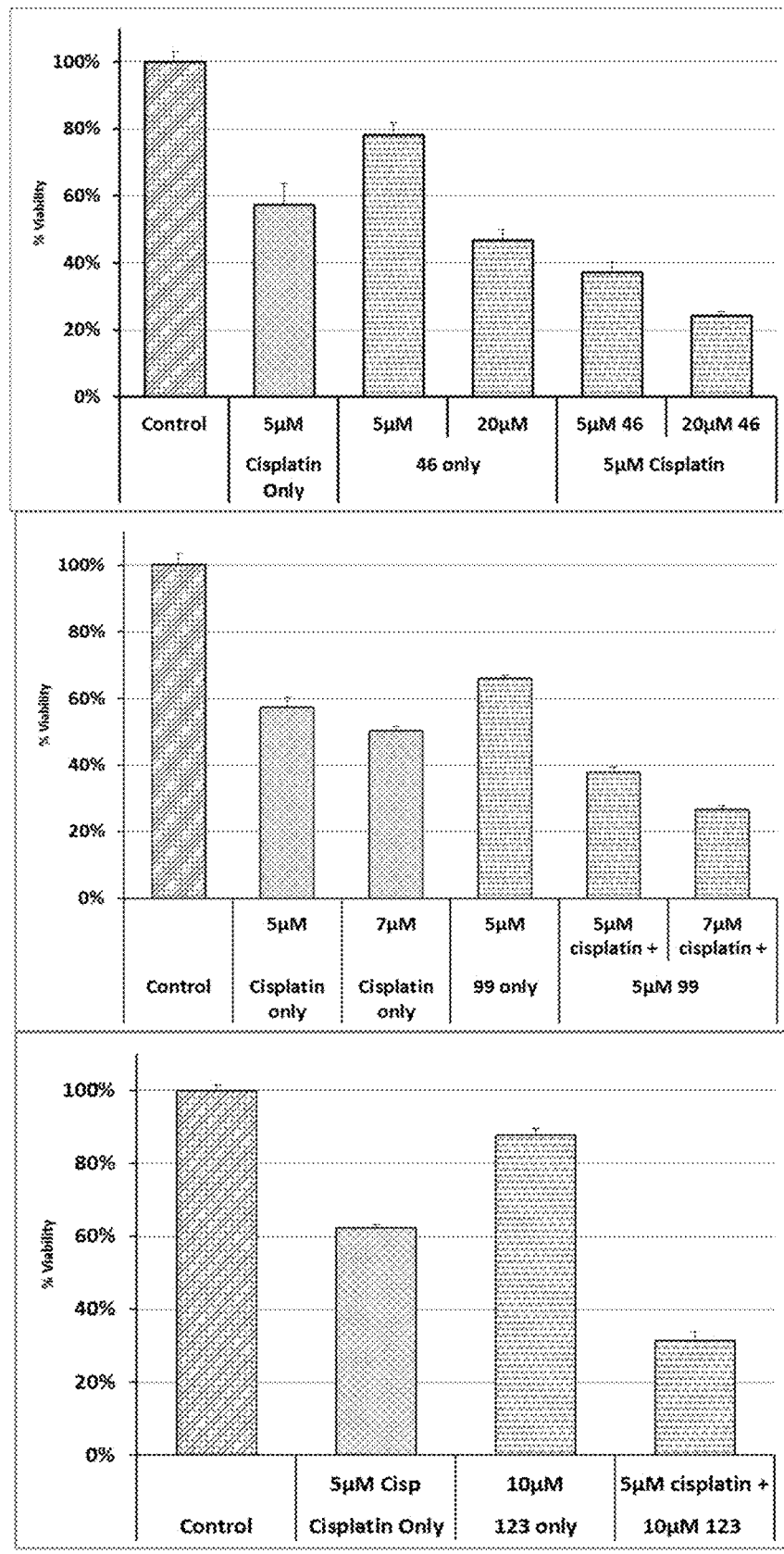
FIG. 14—Cisplatin™ combination experiments—Compounds 46, 99 and 123. Shows that treatment with synthetic derivatives of the compound of Formula II (either 46, 99 and 123) sensitizes chemoresistant cancer cell line A549, lung carcinoma to low dose cisplatin. Cells were treated with a range of doses of active in combination with a range of doses of Cisplatin™ for 96 hrs. Each data point is representative of at least 4 biological repetitions and error=s.e.m).

FIG. 13 demonstrates that chemically synthesised derivatives of Formula II (Compounds 46, 99 and 123) are also effective in a dose dependant manner as an anticancer agent alone, and can act as an agent to sensitise cancer cells to other chemotherapeutic agents (FIG. 14).

Use of the compound(s) for the treatment of autism.

Direct evidence is provided that inhibiting eIF4A represents a new route to treating ASD based on the data presented by Gkogkas et al. *Nature* 2013, 493:371-7. Firefly/*renilla* luciferase reporter experiments conducted using cultured human cell lines show that eIF4A is a viable therapeutic target for the treatment of ASD and that eIF4A1 inhibition using either hippuristanol or compound of the synthetic version of the natural molecule and synthetic derivatives (data also shown for 46) result in the selective inhibition of NLGN1 translation.

Treatment with the compound of Formula II (and compound 46) (FIG. 5 and FIG. 10) selectively decrease the firefly luciferase signal from a reporter construct containing the NLGN1 5'UTR upstream of a firefly luciferase gene. The translation of luciferase reporters downstream of the NLGN1 5'UTR has been proven to be dependent on the activity of the translation initiation complex eIF4F (Gkogkas et al Nature 2013, 493:371-7)—a complex containing the helicase eIF4A. Equivalent treatment had little effect on the signal generated from either a co-transfected *renilla* luciferase reporter control or cells transfected with an equivalent construct containing the NLGN2 5'UTR upstream of a firefly luciferase gene (FIG. 5 and FIG. 10).

The level of translation inhibition of NLGN1 is shown to be equivalent to that induced by a known inhibitor of eIF4A, hippuristanol. This data further demonstrates that the compound acts to target the translation initiation complex and also provides proof that the translation of NLGN1 is relatively more dependent on the activity of eIF4A in comparison with NLGN2. Data also shows that the inhibitory effects observed are not due to the anti-proliferative activity of the compound at this dose and treatment time.

Materials and Methods

Production of the Compound of Formula II The compound of Formula II is a glycoglycerol lipid, the synthesis of such compounds is well known. The skilled man could readily make the compound of Formula II, or the an acetyl derivative thereof, by following the reaction mechanism described in Manzo, E.; Letizia Ciavatta, M.; Pagano, D.; Fontana, A. *Tetrahedron Lett.* 2012, 53, 879.

Alternatively the compound of Formula II may be recovered from plant materials, for example tomatoes. Tomatoes were grown under standard glass house, harvested and snap frozen in liquid nitrogen. Tissue was ground under liquid nitrogen to form a powder, mixed with 2 volumes of MeOH (wt/vol) and heated at 50° C. for 10 minutes. This mixture was then centrifuged at 4000 RPM to pellet cellular debris and the supernatant transferred to a clean tube. The MeOH was then partitioned into a chloroform phase, and the chloroform layer then dried down to yield a pellet.

The crude extract was adsorbed onto chromatography grade silica gel and dry-loaded onto a silica gel flash chromatography column. The products were eluted with a gradient of 0-20% methanol in dichloromethane, and fractions were collected and tested for biological activity. The active fractions were evaporated in vacuo to give an oil (155 mg). Further purification was performed by batch-wise reverse phase HPLC (Varian Prostar; Polaris 5 micron C18-A column (250 mm×10 mm); gradient elution 80% H2O 20% MeCN to 0% H2O100% MeCN following the following method: 80% H2O 20% MeCN 2 min; 0% H2O 100% MeCN 20 min; 0% H2O 100% MeCN 48 min; 80% H2O 20% MeCN 50 min). The active fractions (eluting at 30 min) were collected and evaporated in vacuo to give the active molecule whose NMR (1H and 13C), HRMS and IR data confirmed it to be the structure shown in FIG. 1.

Cell Culture Conditions

Cells were cultured and maintained using standard conditions as described on the American Type Culture Collection Web page (see ATCC for details http://www.lgcstandards-atcc.org) in appropriate media e.g. Dulbecco's Modified Eagle's Medium (DMEM) or Roswell Park Memorial Institute medium (RPMI) (Sigma) supplemented with 10% FCS, and 1% Penicillin/Streptomycin (Life Technologies).

Polysome Profiling

Polysome profiles were obtained using sucrose density centrifugation. Briefly one 15 cm plate of cultured Neuroblastoma cells (SH-SY5Y) were grown per treatment to a confluency of 70%. Cells were then treated with either active or equivalent DMSO vehicle control for 20 min. Cells were harvested, lysed and loaded onto sucrose gradients then centrifuged at 38,000 RPM for 2 hours (as described in Bottley et al, 2010). Gradients were fractionated and polysome profiles determined through a continuous monitoring at absorbance 260 nm (described previously Johannes et al. 1999).

Transient Transfection Conditions and Luciferase Reporter Constructs

Experiments conducted using Firefly luciferase reporter plasmids containing the 5' untranslated regions (UTRs) of the genes amyloid precursor protein (APP), thioredoxin (TXN) were conducted with reagents and materials described by Bottley et al, 2010. Experiments conducted using Firefly luciferase reporter plasmids containing the 5' UTRs of the genes EGFR, BACE1 and Actin were conducted with reagents and materials described by Webb, 2012 (http://etheses.nottingham.ac.uk/2724/). Firefly luciferase reporter plasmids containing the 5' untranslated regions (UTRs) of the genes Neuroligin 1 and Neuroligin 2 were a kind gift from Professor Nahum Sonenberg (McGill) and used as described by Gkogkas et al, *Nature* 2013, 493:371-7.

Cells were transfected using FuGene 6 (Roche) following the manufacturer's instructions. The activities of firefly and renilla luciferase in lysates prepared from transfected cells were measured using a commercially available Luciferase reporter assay system (Promega) and light emission was measured over a 10 sec interval using a TECAN luminometer. For each experiment described, data was obtained from a minimum of at least 3 biological repetitions per treatment.

Cell Proliferation Experiments

Prior to treatment cells were cultured to an appropriate confluency in 96 well tissue culture plates (Fisher). Cells remained either supplemented with fresh media or treated with fresh media containing active or an equivalent volume of DMSO (vehicle control). Where used, Cisplatin™ was diluted to a stock concentration in Dimethylformamide (DMF), then handled as per the manufacturer's instructions. To determine relative cell viability, reagents WST-1 (Roche) or MTT (Sigma) were used as per the manufacturer's instructions and absorbance at 450 nm measured using a Victor plate reader (Perkin Elmer).

Primary Canine Tumour Cell Experiments.

Biopsy tissue was removed from knee, abdomen and skin of a 7 year old dog. Cells harvested from the canine source were confirmed through histological evaluation to be histiocytic sarcoma tumour cells. Samples were fragmented prior to collagenase treatment in controlled conditions at 37° C. for 3 hours. Cells were then sedimented by low speed centrifugation and resuspended in selective culture media using proprietary methods and materials developed by Petscreen Ltd. Experiments were performed in 96 well tissue culture plates with a minimum of three biological repetitions per treatment.

Production of the Compounds of Formula I and La in FIGS. 16 and 17

The compounds of Formula I and Ia in FIGS. 16 and 17 are synthetic variants of the compound of Formula II. For example, they may use glucose or mannose sugar units rather than galactose and they may use a central linker unit that has an additional $CH_2$ group.

The synthesis of glycoglycerol lipids and the like is well known and it is within the skilled person's ability to modify known reaction techniques for synthesising glycoglycerol lipids to produce the compounds of Formula I and Ia in FIGS. 16 and 17 (which are compounds 99, 218, 139, 184, 123, 180, 124, 159, 38, 215, 146, 122, 119, 62, 120, 46, 61, 57, 60, 56, 154, and 58, which are also shown in the description above).

Specifically, the compounds of Formula I and Ia in FIGS. 16 and 17 were each made by following the reaction mechanism described in Manzo, E.; Letizia Ciavatta, M.; Pagano, D.; Fontana, A. *Tetrahedron Lett.* 2012, 53, 879.

This synthesis is a versatile and simple procedure based on trichloro-acetimidate methodology and the use of peracetate sugar substrates. The chemical strategy allows stereoselective preparation of lipid derivatives, and other related derivatives, of sugars such as galactose and glucose and mannose. The synthetic approach is designed to obtain enantiomerically pure regio- and stereo-isomers including derivatives containing poly-unsaturated fatty acids.

In essence, the synthesis recognises that glycoglycerol lipids such as:

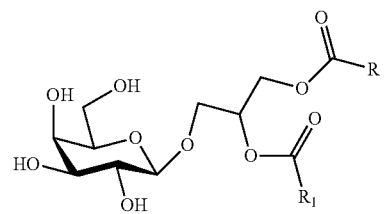

can be derived from the starting materials:

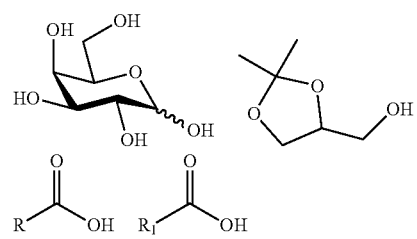

The required variations on these starting materials to achieve the compounds in FIGS. 16 and 17 can be readily seen by the skilled person; e.g. a different sugar unit, a linker unit with an additional $CH_2$ group, a choice of R and R1 groups.

The manufacture of each of the compounds in FIGS. 16 and 17 was therefore based on following steps from that known synthetic route (shown schematically below) and with selection of the appropriate starting materials/reagents to provide the appropriate sugar unit, R and R1 groups and linker unit therebetween.

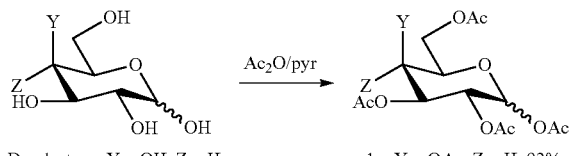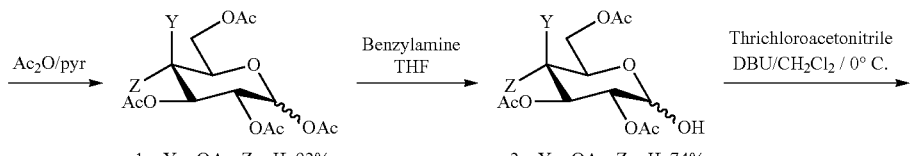

D-galactose: Y = OH, Z = H
D-glucose: Y = H, Z = OH

1: Y = OAc, Z = H, 92%
12: Y = H, Z = OAc, 95%

2: Y = OAc, Z = H, 74%
13: Y = H, Z = OAc, 71%

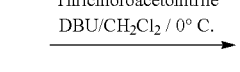
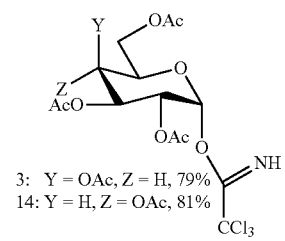

3: Y = OAc, Z = H, 79%
14: Y = H, Z = OAc, 81%

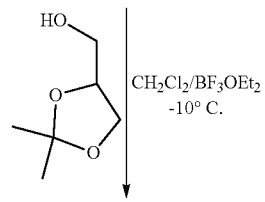

$CH_2Cl_2/BF_3OEt_2$
-10° C.

-continued

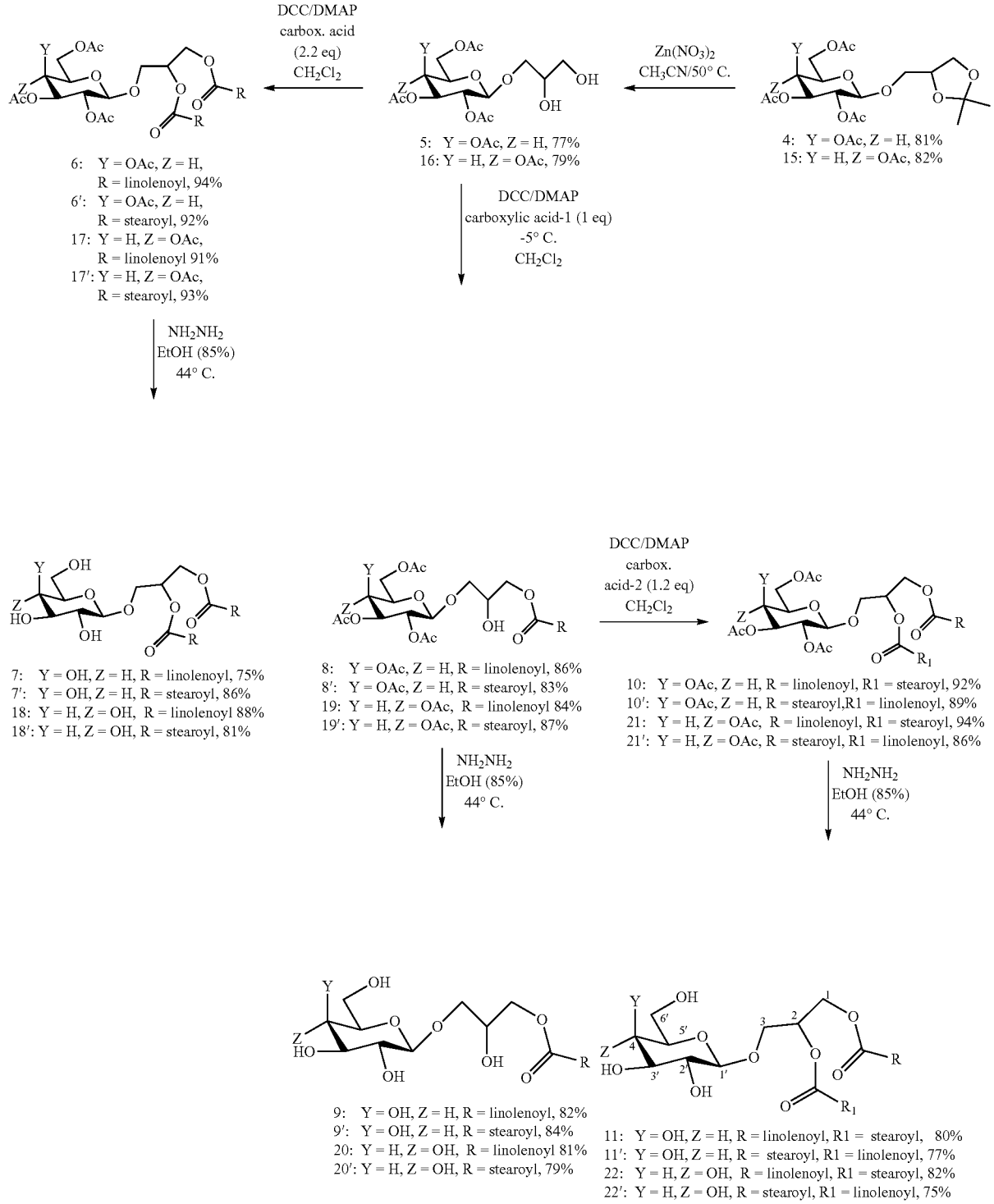

The majority of the compounds made and illustrated in FIGS. 16 and 17 are directly based on this synthesis, with the difference solely lying in the choice of sugar, and whether it is protected or not, and the choice of R and R' groups. For example, compounds 123, 180, 124, 38, 122, 119, 62, 120, 61, 57, 60, 56 and 58.

Synthetic Route to Compound 159

The synthetic route to 159 followed an identical route to that used for all other esters mentioned in the above *Tetrahedron Letters* paper by Manzo, E et al, with the only difference being that diphenyl acetic acid was used instead of a fatty acid to provide the R and R' groups.

Synthetic Route to Compound 139

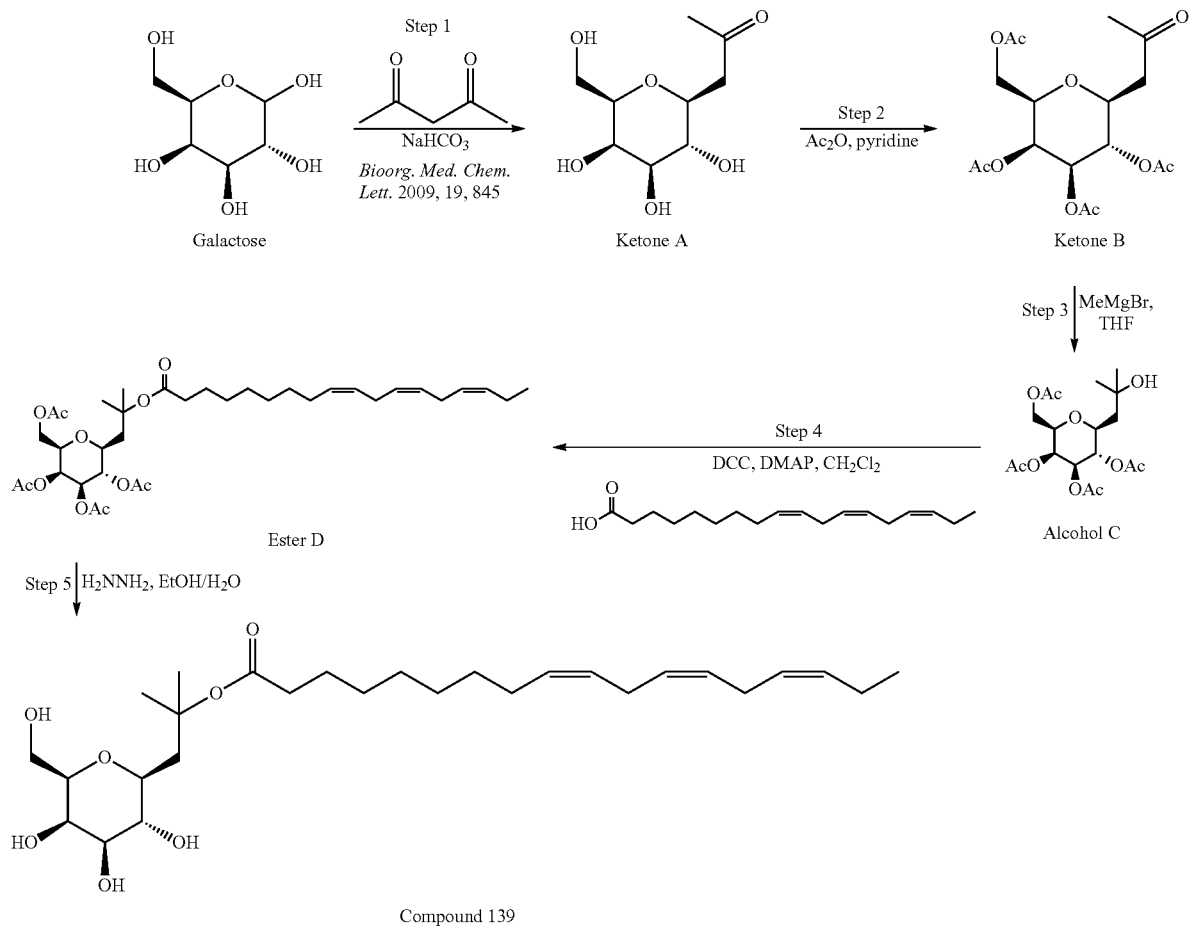

Preparation of Ketone A

The ketone A (step 1 above) was synthesised from galactose according to: A Cavezza, C. Boulle, A. Guéguiniat, P. Pichaud, S. Trouille, L. Ricard, M. Dalko-Csiba, *Bioorganic & Medicinal Chemistry Letters* 2009, 19, 845-849.

Preparation of Ketone B

To a stirred suspension of the known ketone A (1.81 g, 8.1 mmol) in dichloromethane (8 mL) and pyridine (4.90 mL, 60.0 mmol) at OC was added acetic anhydride (4.72 mL, 4.72 mmol) drop wise. The resulting reaction mixture was warmed to room temp and stirred overnight (ca 16 hours). The reaction was poured in to water and extracted with dichloromethane (3×50 mL), the combined organic phase were washed with 3M HCl (3×50 mL), sat NaHCO$_3$(50 mL), brine (50 mL), dried over MgSO4 and evaporated, to afford a gum which was purified by silica gel chromatography (1:1 to 0:1 Petrol:Et2O) to afford the tetra acetate ketone B (2.87 g, 7.43 mmol, 57%) as a pale yellow solid.

Preparation of Alcohol C

To a stirred solution of the ketone B (420 mg, 1.08 mmol) in THF (10 mL) at −78° C. was added MeMgBr (1.4M, 1.85 mL, 2.6 mmol) drop wise. The resulting solution was stirred at −78° C. for 4 hours. The reaction was quenched by the addition of sat. ammonium chloride solution (20 mL) and extracted with EtOAc (3×25 mL), the combined organic phase were washed with brine (25 mL), and dried over MgSO4 and evaporated, to afford a gum which was purified by silica gel chromatography (1:1 to 0:1 Petrol:EtOAc) to afford the alcohol C (133 mg, 0.328 mmol, 30.5%) as a colourless solid.

Preparation of Ester D

DCC coupling according to a slightly modified procedure reported in *Tetrahedron Lett.* 2012, 53, 879.

To a stirred solution of the alcohol C (126 mg, 0.31 mmol) in dichloromethane (6 mL) at room temp under argon was added linolenic acid (94.5 mg, 0.34 mmol), dicyclohexylcarbodiimide (70.6 mg, 0.34 mmol) and DMAP (8.4 mg, 0.068 mmol), the reaction mixture was stirred overnight (ca 16 hours) at room temp. The reaction was cooled to −20° C., and filtered, the filtrated was and evaporated under reduced pressure and the mixture was purified by silica gel chromatography (8:1 to 4:1 Petrol:EtOAc) to afford the ester D (115 mg, 0.173 mmol, 55.8%) as a colourless oil.

Preparation of Compound 139

Deprotection according to the procedure reported in *Tetrahedron Lett.* 2012, 53, 879.

To a stirred solution of the ester D (105 mg, 0.158 mmol) in aq. ethanol (85%) (5 mL) at 44° C. was added hydrazine mono-hydrate (63 µL, 1.26 mmol), the reaction mixture was stirred at 44° C. for 4 hours. The solvent was removed under a stream of nitrogen and the residue was purified by silica gel chromatography 10:1 dichloromethane:MeOH) to afford the compound 139 (38 mg, 0.077 mmol, 48%) as a colourless oil.

Synthetic Route to Compounds 99, 218, 184, 215 and 46

The modified linker unit as used in compounds 99, 218, 184, 215 and 46 (where there is an additional $CH_2$ within the linker unit) as compared to the linker unit illustrated in the *Tetrahedron Letters* reaction scheme above) is not commercially available; however it is a known compound, whose synthesis is reported in the following papers:

C. Iwata, N. Maezaki, K. Hattori, M. Fujita, Y. Moritani, Y. Takemoto, T. Tanaka, T. Imanishi, *Chemical and Pharmaceutical Bulletin*, 1993, 41, (2), 339-345

R. Schillera, L. Tichotováa, J. Pavlíka, V. Buchtab, B Melicharc, I. Votrubad, J. Kuneša, M. Špuláka, M. Poura, *Bioorganic & Medicinal Chemistry Letters*, 2010, 20, (24), 7358-7360 H. A. Bates, J. Farina, M. Tong, *J. Org. Chem.*, 1986, 51 (14), 2637-2641.

The linker unit was therefore synthesised according to the known methodology, before being used in the *Tetrahedron Letters* reaction scheme.

To illustrate this, the synthetic route to compound 46 is set out below:

This synthesis illustrates the straightforward nature of the modifications needed to the reaction scheme from the above *Tetrahedron Letters* paper by Manzo, E et al to synthesise compounds having an altered linker unit.

It will be noted that this route is almost identical to that described in the *Tetrahedron Letters* paper but it does differ in Step 4 where a modified alcohol is used to modify the linker unit. The preparation of this modified alcohol is given in *J. Org. Chem.* 1986, 51, 2637 (it is structure 14 in that paper).

The adaptations to the above synthetic route to compound 46 that would be required to reach the compounds 99, 218, 184 and 215 (which also include the modified linker unit) are easily apparent. The differences lie in the choice of sugar, and whether it is protected or not, and the choice of R and R' groups.

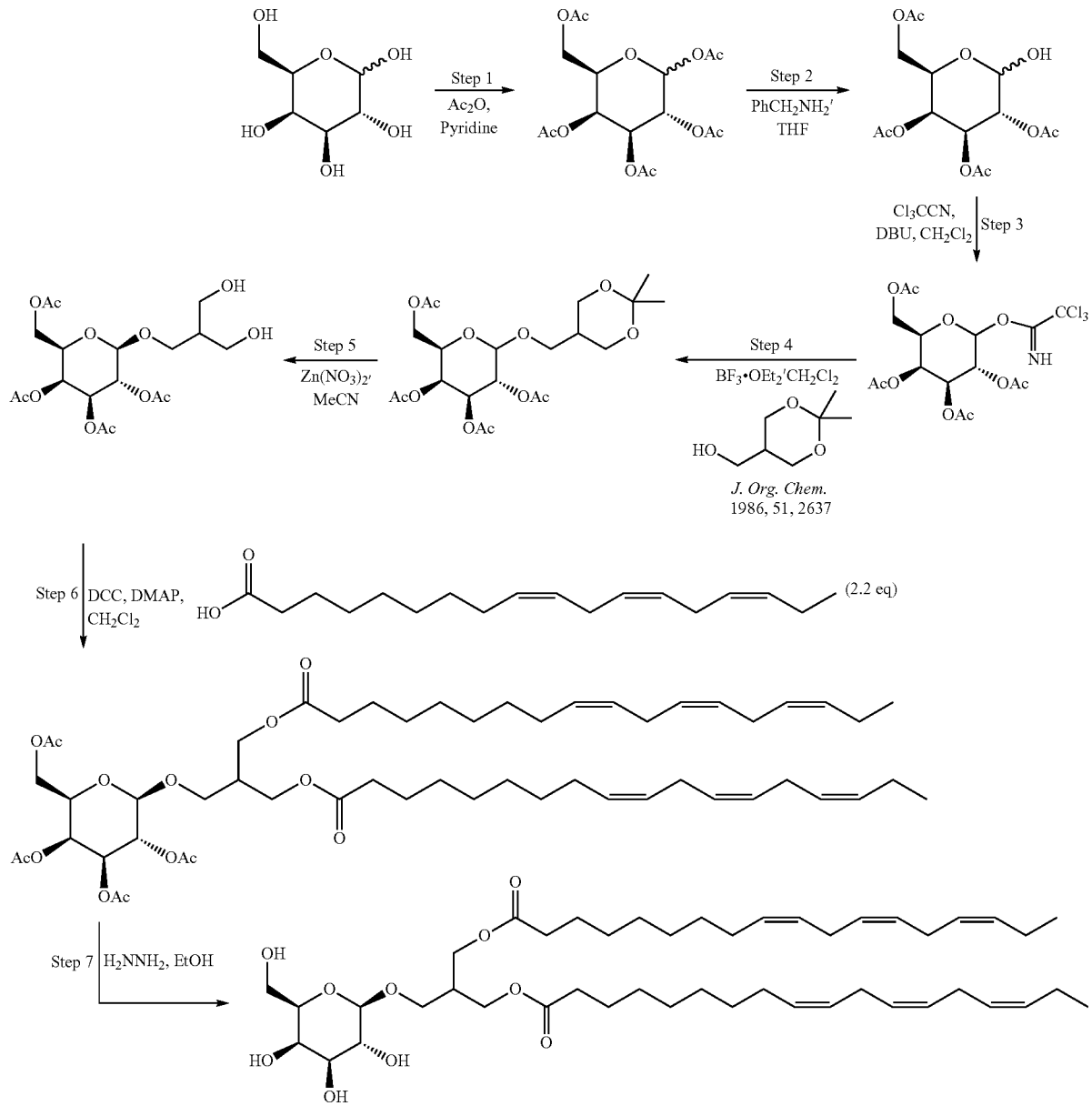

Synthetic Route to Compounds 146 and 154

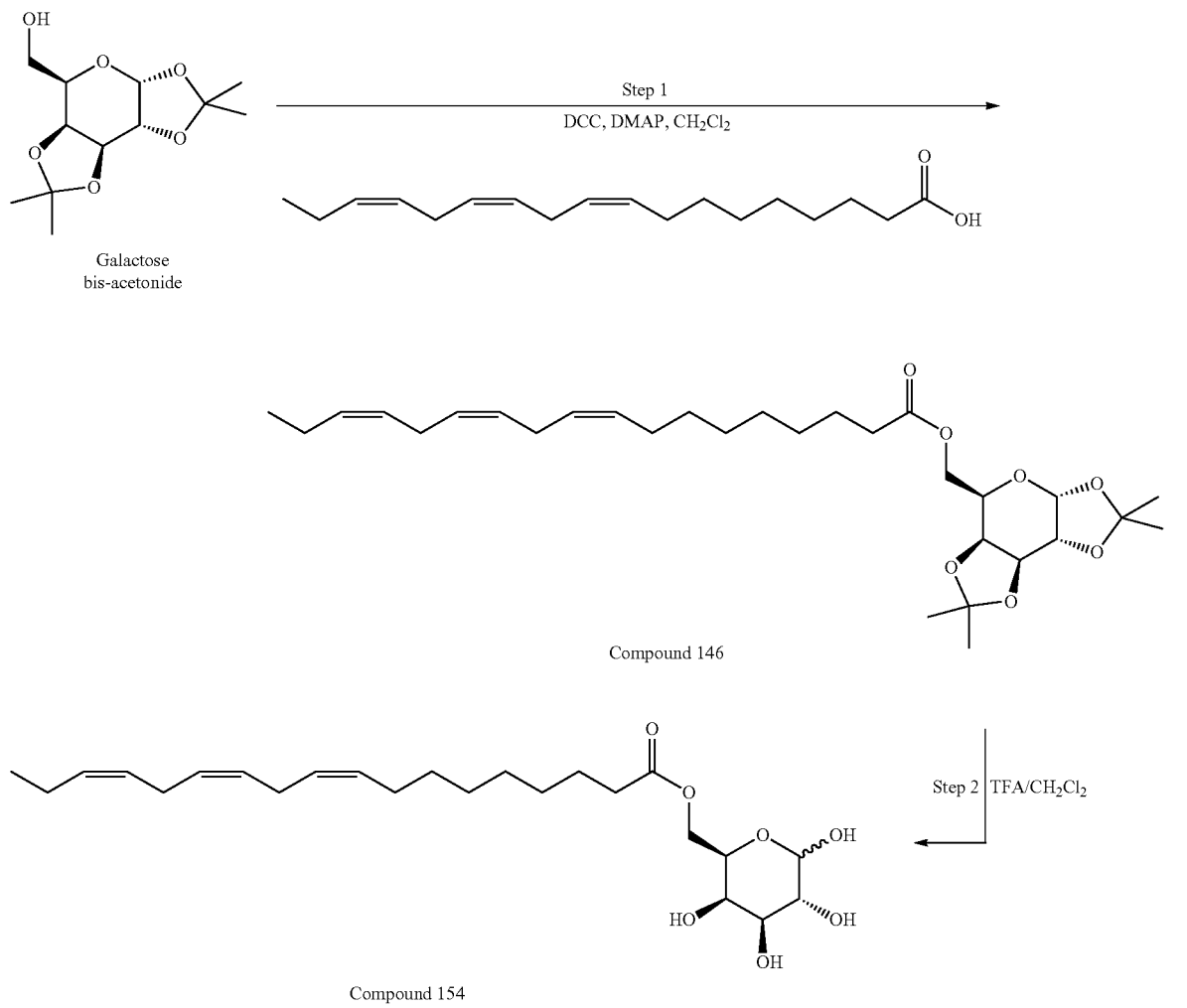

Preparation of Compound 146

To a stirred solution of the commercially available galactose bis-acetonide (260 mg, 1.00 mmol) in dichloromethane (10 mL) at room temp under argon was added linolenic acid (278 mg, 1.0 mmol), dicyclohexylcarbodiimide (206 mg, 1.0 mmol) and DMAP (24 mg, 0.2 mmol), the reaction mixture was stirred overnight (ca 16 hours) at room temp. The reaction was cooled to −20° C., and filtered, the filtrated was and evaporated under reduced pressure and the mixture was purified by silica gel chromatography (8:1 to 2:1 Petrol: Et2O) to afford the compound 146 (438 mg, 0.84 mmol, 84%) as a colourless oil.

Preparation of Compound 154

To a stirred solution of the compound 146 (106 mg, 0.20 mmol) in DCM (1 mL) at 0° C. was added trifluoroacetic acid (1 mL), and the reaction was stirred for 12 hours. The reaction was evaporated under reduced pressure and the residue was purified by silica gel chromatography (10:1 DCM:MeOH) to afford compound 154 as a mixture of a anomers (60 mg, 0.136 mmol, 68%) as a colourless oil.

The invention claimed is:

1. A compound having the structure (139)

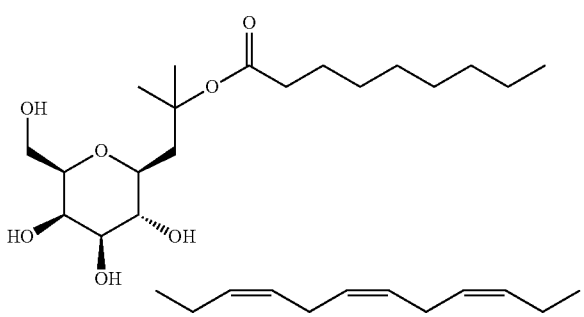

or a pharmaceutically acceptable salt thereof.

2. A pharmaceutical composition comprising the compound of claim 1, or a pharmaceutically acceptable salt thereof, together with a pharmaceutically acceptable carrier, diluent or excipient.

3. A nutraceutical composition comprising the compound of claim 1, or a pharmaceutically acceptable salt thereof together with a nutraceutically acceptable carrier, diluent or excipient.

4. A kit comprising the compound of claim 1, or a pharmaceutically acceptable salt thereof, and an anti-cancer agent, wherein the anti-cancer agent is provided in a form suitable for, and/or with instructions for, administration in a daily dosage which is significantly reduced compared to the dosage of the anti-cancer agent if administered alone.

5. A method for the treatment of a subject having a disease or condition selected from the group consisting of cancer, autistic spectrum disorders, Alzheimer's disease, Parkinson's disease, Huntington's disease, muscle wasting and viral infection, the method comprising administering a compound of claim 1 to the subject.

6. The method of claim 5, wherein the compound is selected from the group consisting of an inhibitor of protein translation, a chemotherapeutic agent, a cell sensitising agent, an antiproliferative agent, an antiviral agent and an adjuvant.

\* \* \* \* \*

UNITED STATES PATENT AND TRADEMARK OFFICE
CERTIFICATE OF CORRECTION

PATENT NO. : 11,248,016 B2
APPLICATION NO. : 16/522216
DATED : February 15, 2022
INVENTOR(S) : Andrew Bottley et al.

Page 1 of 1

It is certified that error appears in the above-identified patent and that said Letters Patent is hereby corrected as shown below:

In the Claims

Column 80, Lines 46-61 (Claim 1):
Please delete the following structure:

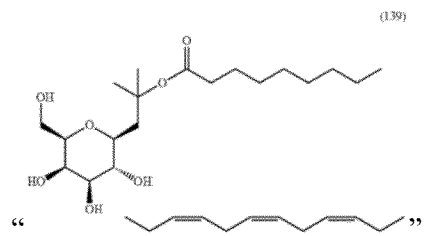

And insert the following structure:

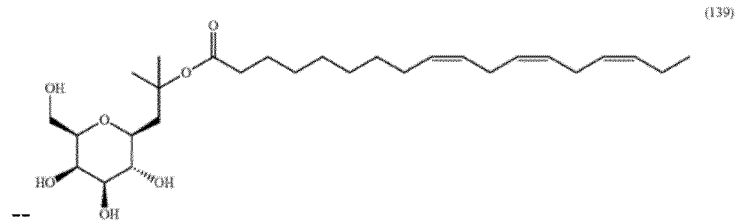

-- therefor.

Signed and Sealed this
Twenty-eighth Day of June, 2022

Katherine Kelly Vidal
*Director of the United States Patent and Trademark Office*